(12) United States Patent
Jenkins et al.

US011179355B2

(10) Patent No.: US 11,179,355 B2
(45) Date of Patent: Nov. 23, 2021

(54) COMPOSITIONS COMPRISING ENZYME-CLEAVABLE AMPHETAMINE PRODRUGS AND INHIBITORS THEREOF

(71) Applicant: Signature Therapeutics, Inc., Palo Alto, CA (US)

(72) Inventors: Thomas E. Jenkins, Half Moon Bay, CA (US); Craig O. Husfeld, San Mateo, CA (US); Julie D. Seroogy, San Carlos, CA (US); Jonathan W. Wray, San Francisco, CA (US)

(73) Assignee: Signature Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 15/042,906

(22) Filed: Feb. 12, 2016

(65) Prior Publication Data
US 2016/0235694 A1    Aug. 18, 2016

Related U.S. Application Data

(62) Division of application No. 13/634,524, filed as application No. PCT/US2011/031846 on Apr. 8, 2011, now abandoned.
(Continued)

(51) Int. Cl.
*A61K 31/165*     (2006.01)
*A61K 9/00*       (2006.01)
(Continued)

(52) U.S. Cl.
CPC .......... *A61K 31/165* (2013.01); *A61K 9/0019* (2013.01); *A61K 9/0053* (2013.01);
(Continued)

(58) Field of Classification Search
None
See application file for complete search history.

(56) References Cited

U.S. PATENT DOCUMENTS 3,842,064 A   10/1974  Greven
3,850,904 A   11/1974  Greven
(Continued)

FOREIGN PATENT DOCUMENTS

DE    1041052    10/1958
DE    1493824    5/1969
(Continued)

OTHER PUBLICATIONS

Simone, Oncology (Introduction), 1997, Textbook of Medicine, 20(1), pp. 1004-1010 (Year: 1997).*
(Continued)

*Primary Examiner* — Savitha M Rao
*Assistant Examiner* — Andrew P Lee
(74) *Attorney, Agent, or Firm* — Khin K. Chin; Bozicevic Field & Francis LLP

(57) ABSTRACT

Pharmaceutical compositions and their methods of use are provided, where the pharmaceutical compositions comprise an amphetamine prodrug that provides enzymatically-controlled release of amphetamine or an amphetamine analog. The composition can further comprise an enzyme inhibitor that interacts with the enzyme(s) that mediates the enzymatically-controlled release of amphetamine or the amphetamine analog from the amphetamine prodrug so as to attenuate enzymatic cleavage of the amphetamine prodrug.

17 Claims, 19 Drawing Sheets

Related U.S. Application Data

(60) Provisional application No. 61/326,609, filed on Apr. 21, 2010.

(51) Int. Cl.
    *A61K 31/24*         (2006.01)
    *C07C 279/14*       (2006.01)
    *A61K 31/16*         (2006.01)
    *C07C 237/22*       (2006.01)
    *A61K 45/06*         (2006.01)
    *A61K 47/54*         (2017.01)

(52) U.S. Cl.
    CPC ............. *A61K 31/16* (2013.01); *A61K 31/24* (2013.01); *A61K 45/06* (2013.01); *A61K 47/542* (2017.08); *A61K 47/543* (2017.08); *C07C 237/22* (2013.01); *C07C 279/14* (2013.01)

(56) References Cited

U.S. PATENT DOCUMENTS

| | | |
|---|---|---|
| 3,853,836 A | 12/1974 | Greven |
| 3,853,838 A | 12/1974 | Greven |
| 3,875,137 A | 4/1975 | Jones et al. |
| 4,104,371 A | 8/1978 | Greven et al. |
| 4,297,346 A | 10/1981 | Rips et al. |
| 4,454,338 A | 6/1984 | Fujii et al. |
| 4,532,255 A | 7/1985 | Fujii et al. |
| 5,109,118 A | 4/1992 | Mizushima et al. |
| 5,217,987 A | 6/1993 | Berger et al. |
| 5,352,704 A | 10/1994 | Okuyama et al. |
| 6,388,122 B1 | 5/2002 | Kido et al. |
| 6,586,196 B1 | 7/2003 | Bronstein et al. |
| 7,060,290 B1 | 6/2006 | Morimoto et al. |
| 7,105,486 B2 | 9/2006 | Mickle et al. |
| 7,189,414 B2 | 3/2007 | Rubinstein et al. |
| 7,223,735 B2 | 5/2007 | Mickle et al. |
| 7,655,630 B2 | 2/2010 | Mickle et al. |
| 7,893,105 B2 | 2/2011 | Xiang et al. |
| 8,163,701 B2 | 4/2012 | Jenkins et al. |
| 8,217,005 B2 | 7/2012 | Jenkins et al. |
| 8,497,237 B2 | 7/2013 | Jenkins et al. |
| 8,569,228 B2 | 10/2013 | Jenkins et al. |
| 8,685,916 B2 | 4/2014 | Jenkins et al. |
| 8,802,681 B2 | 8/2014 | Jenkins et al. |
| 8,921,418 B2 | 12/2014 | Jenkins et al. |
| 8,962,547 B2 | 2/2015 | Jenkins et al. |
| 9,023,860 B2 | 5/2015 | Jenkins et al. |
| 9,095,627 B2 | 8/2015 | Jenkins et al. |
| 9,139,612 B2 | 9/2015 | Jenkins et al. |
| 2003/0035831 A1 | 2/2003 | Modi |
| 2003/0180352 A1 | 9/2003 | Patel et al. |
| 2004/0063628 A1 | 4/2004 | Piccariello et al. |
| 2005/0054561 A1 | 3/2005 | Mickle et al. |
| 2005/0080012 A1 | 4/2005 | Mickle et al. |
| 2005/0176644 A1 | 8/2005 | Mickle et al. |
| 2005/0176645 A1 | 8/2005 | Mickle et al. |
| 2007/0042955 A1 | 2/2007 | Mickle et al. |
| 2007/0082929 A1 | 4/2007 | Gant et al. |
| 2007/0093420 A1 | 4/2007 | Yeomans et al. |
| 2007/0123468 A1 | 5/2007 | Jenkins et al. |
| 2007/0203055 A1 | 8/2007 | Mickle et al. |
| 2008/0139653 A1 | 6/2008 | Mickle et al. |
| 2009/0136980 A1 | 5/2009 | Bebbington et al. |
| 2009/0137618 A1 | 5/2009 | Jenkins et al. |
| 2009/0192093 A1 | 7/2009 | Mickle et al. |
| 2009/0209569 A1 | 8/2009 | Arnelle et al. |
| 2010/0022792 A1 | 1/2010 | Shen |
| 2010/0035826 A1 | 2/2010 | Jenkins et al. |
| 2010/0080797 A1 | 4/2010 | Yeomans et al. |
| 2010/0092562 A1 | 4/2010 | Hollenbeck et al. |
| 2010/0227921 A1 | 9/2010 | Franklin et al. |
| 2010/0267614 A1 | 10/2010 | Jenkins et al. |
| 2010/0286186 A1 | 11/2010 | Franklin et al. |
| 2011/0040072 A1 | 2/2011 | Mickle et al. |
| 2011/0262355 A1 | 10/2011 | Jenkins et al. |
| 2011/0262359 A1 | 10/2011 | Jenkins et al. |
| 2011/0262360 A1 | 10/2011 | Jenkins et al. |
| 2012/0230916 A1 | 9/2012 | Jenkins et al. |
| 2013/0059914 A1 | 3/2013 | Jenkins et al. |
| 2013/0210700 A1 | 8/2013 | Jenkins et al. |
| 2013/0210854 A1 | 8/2013 | Jenkins et al. |
| 2014/0121152 A1 | 5/2014 | Jenkins et al. |
| 2014/0206597 A1 | 7/2014 | Jenkins et al. |
| 2015/0031635 A1 | 1/2015 | Jenkins et al. |

FOREIGN PATENT DOCUMENTS

| | | |
|---|---|---|
| EP | 1782834 | 5/2007 |
| GB | 1425099 | 2/1976 |
| WO | WO 1997012903 | 4/1997 |
| WO | 2002043767 | 6/2002 |
| WO | 2005032474 | 4/2005 |
| WO | 2007022535 | 2/2007 |
| WO | 20070120864 | 10/2007 |
| WO | WO 2007140272 | 12/2007 |
| WO | 2008012046 | 1/2008 |
| WO | 2007120648 | 7/2008 |
| WO | WO 2008101187 | 8/2008 |
| WO | WO 2008101202 | 8/2008 |
| WO | 2009067703 | 5/2009 |
| WO | WO 2010045599 | 4/2010 |
| WO | WO 2010148305 | 12/2010 |
| WO | WO 2011133178 | 10/2011 |

OTHER PUBLICATIONS

Danziger, Automated site-directed drug design: a general algorithm for knowledge acquisition about hydrogen-bonding regioins at protein surfaces, 1989, Proc. R. Soc. Lond., 236, pp. 101-113 (Year: 1989).*

Bernkop-Schnurch (1998) "The use of inhibitory agents to overcome the enzymatic barrier to perorally administered therapeutic peptides and proteins" *J Control Release* 50(1-2):1-16.

Birk et al. (1976) "Trypsin and chymotrypsin inhibitors from soybeans" *Methods in Enzymology* 45:700-707.

Database Registry (2001) Abstract, Database accession No. 339089-42-8.

De Nardo et al. (1977) "Studies on chemical structure and sweet taste. Note XIII. L-Acylamidosuccinilic acid derivatives" Database Caplus, Abstract, Database accession No. 1977:119365.

Geratz et al. (1976) "Novel bis(benzamidine) compounds with an aromatic central link. Inhibitors of thrombin, pancreatic kallikrein, trypsin, and complement" *J. Med. Chem.* 19:634-639.

Göke et al. (1984) "Effect of a Specific Serine Protease Inhibitor on the Rat Pancreas: Systemic Administration of Camostate and Exocrine" *Digestion* 30:171-178.

Gomes et al. (2007) "Cyclization-activated prodrugs" *Molecules* 12:2484-2506.

Hijikata-Okunomiya et al. (2000) "Selective Inhibition of Trypsin by (2R,4R)-4-Phenyl-1-[$N^{\alpha}$-(7-methoxy-2-naphthalenesulfonyl)-L-arginyl]-2-piperidinecarboxylic Acid" *J. Biochem.* 275:18995-18999.

Iwanowicz et al. (2002) "Retro-Binding Thrombin Active Site Inhibitors: Identification of an Orally Active Inhibitor of Thrombin Catalytic Activity" *Bioorganic and Medicinal Chemistry Letters* 12:3183-3186.

Kunze et al. (1983) "Effects of the serine protease inhibitors FOY and FOY 305 on phospholipase A I (EC 3.1.1.32) activity in rat-liver lysosomes" *Pharm. Research Com.* 15: 451-459.

Lapidus and Sweeney (1973) "L-4'-Cyano-3-(2.2.2-trifluoroacetamideo)s uccinanilic Acid and Related Synthetic Sweetening Agents" *J. Med. Chem.* 16(2):163-166.

Lin et al. (1993) "The 0.25-nm X-ray structure of the Bowman-Birk type inhibitor from mung bean in ternary complex with porcine trypsin" *Eur. J. Biochem.* 212:549-555.

Markwardt et al. (1968) "Comparative studies on the inhibition of trypsin, plasmin, and thrombin by derivatives of benzylamine and benzylamidine" *Eur. J. Biochem*, 6:502-506.

(56) References Cited

OTHER PUBLICATIONS

Nechab et al. (2008) "N-Acylglycinates as acyl donors in serine protease-catalyzed kinetic resolution of amines. Improvement of selectivity and reaction rates." *Org. Biol. Chem.* 6:3917-3920.

Ozawa et al. (1966) "The reactive site of trypsin inhibitors" *J. Biol. Chem.* 241:3955-3961.

Plummer et al. (1997) "Design of peptidomimetic ligands for the pp60srcSH2 domain" *Bioorganic and Medicinal Chemistry* 5(1):41-47.

Ramjee et al. (2000) "The Kinetic and Structural Characterization of the Reaction of Nafamostat with Bovine Pancreatic Trypsin" *Thrmb Res.* 98(6):559-569.

Reddy et al. (2012) "An improved process for the preparation of lisdexamfetamine and its pharmaceutically acceptable salts" Database Caplus, Abstract, Database accession No. 2012:654913.

Renatus et al. (1998) "Structural and Functional Analyses of Benzamidine-Based Inhibitors in Complex with Trypsin: Implications for the Inhibition of Factor Xa, tPA, and Urokinase" *J. Med. Chem.* 41(27):5445-5456.

Senoo et al. (1966) "Glutamic acid amides" Database Caplus, Abstract, Database accession No. 1966:19804.

Tanizawa et al. (1987) "Inverse Substrates for Tryspin and Tryspin-like Enzymes" *Acc. Chem. Res.* 20:337-343.

Testa et al. (2003) "Hydrolysis in Drug and Prodrug Metabolism" Verlag Helvetica Chimica Acta, Postfach, CH-8042, Switzerland, pp. 420-534.

Tirkkonen et al. (2004) "Drug interactions with the potential to prevent prodrug activation as a common source of irrational prescribing in hospital inpatients" *Clinical Pharmacology and Therapeutics* 76(6):639-647.

Umezawa (1976) "Structure and activities of protease inhibitors of microbial origin" *Methods in Enzymology* 45:678-695.

Song, Xiaoping et al. (2002) "Synthesis of a Novel Cyclic Prodrug of RGD Peptidomimetic to Improve Its Cell Membrane Permeation" Bioorg Chem 30(4):285-301.

* cited by examiner

COMPOSITIONS COMPRISING ENZYME-CLEAVABLE AMPHETAMINE PRODRUGS AND INHIBITORS THEREOF

CROSS-REFERENCE TO RELATED APPLICATIONS

This application claims priority benefit of the U.S. Provisional Application Ser. No. 61/326,609 filed on Apr. 21, 2010; the disclosure of which application is herein incorporated by reference in its entirety.

INTRODUCTION

Amphetamines are susceptible to misuse, abuse, or overdose. Use of and access to these drugs therefore needs to be controlled. The control of access to these types of drugs is expensive to administer and can result in denial of treatment for patients suffering from conditions such as Attention Deficit Hyperactivity Disorder (ADHD), Chronic Fatigue Syndrome (CFS), brain injury, narcolepsy, or obesity. Furthermore, control of use is often ineffective, leading to substantial morbidity and deleterious social consequences. Current existing amphetamine drug products provide no significant barriers to abuse and misuse by patients.

SUMMARY

The present disclosure provides pharmaceutical compositions, and their methods of use, where the pharmaceutical compositions comprise an amphetamine prodrug that provides enzymatically-controlled release of amphetamine or an amphetamine analog. The composition can further comprise an enzyme inhibitor that interacts with the enzyme(s) that mediates the enzymatically-controlled release of amphetamine or the amphetamine analog from the amphetamine prodrug so as to attenuate enzymatic cleavage of the amphetamine prodrug.

The embodiments include compositions comprising an amphetamine prodrug, wherein the amphetamine prodrug comprises amphetamine or an amphetamine analog covalently bound to a promoiety comprising a GI enzyme-cleavable moiety, wherein cleavage of the GI enzyme-cleavable moiety by a GI enzyme mediates release of amphetamine or the amphetamine analog; and, optionally, a GI enzyme inhibitor that interacts with the GI enzyme that mediates enzymatically-controlled release of amphetamine or the amphetamine analog from the amphetamine prodrug following ingestion of the composition. Such cleavage can initiate, contribute to or effect release of amphetamine or the amphetamine analog.

The embodiments include dose units comprising compositions comprising an amphetamine prodrug and a GI enzyme inhibitor, where the amphetamine prodrug and GI enzyme inhibitor are present in the dose unit in an amount effective to provide for a pre-selected pharmacokinetic (PK) profile following ingestion. In further embodiments, the pre-selected PK profile comprises at least one PK parameter value that is less than the PK parameter value of amphetamine released following ingestion of an equivalent dosage of amphetamine prodrug in the absence of inhibitor. In further embodiments, the PK parameter value is selected from an amphetamine Cmax value, an amphetamine exposure value, and a (1/amphetamine Tmax) value.

In certain embodiments, the dose unit provides for a pre-selected PK profile following ingestion of at least two dose units. In related embodiments, the pre-selected PK profile of such dose units is modified relative to the PK profile following ingestion of an equivalent dosage of amphetamine prodrug without inhibitor. In related embodiments, such a dose unit provides that ingestion of an increasing number of the dose units provides for a linear PK profile. In related embodiments, such a dose unit provides that ingestion of an increasing number of the dose units provides for a nonlinear PK profile. In related embodiments, the PK parameter value of the PK profile of such a dose units is selected from an amphetamine Cmax value, a (1/amphetamine Tmax) value, and an amphetamine exposure value.

The embodiments include compositions comprising a container suitable for containing a composition for administration to a patient; and a dose unit as described herein disposed within the container.

The embodiments include dose units of an amphetamine prodrug and a GI enzyme inhibitor wherein the dose unit has a total weight of from 1 microgram to 2 grams. The embodiments include pharmaceutical compositions of an amphetamine prodrug and a GI enzyme inhibitor wherein the combined weight of amphetamine prodrug and GI enzyme inhibitor is from 0.1% to 99% per gram of the composition.

The present disclosure provides a compound of formula AM-(I), and compositions and dose units comprising a compound of formula AM-(I):

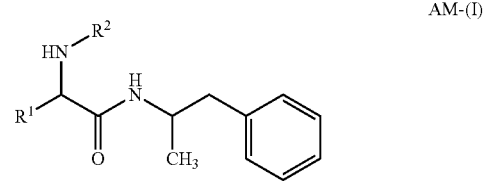

AM-(I)

wherein
$R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and
$R^2$ is an acyl, substituted acyl, or an N-acyl derivative of a peptide;
or a salt, hydrate or solvate thereof.

The present disclosure provides a compound of formula AM-(II), and compositions and dose units comprising a compound of formula AM-(II):

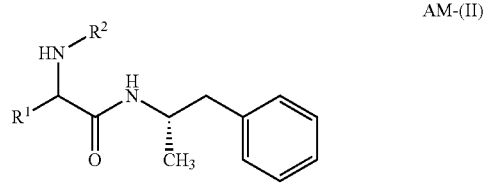

AM-(II)

wherein
$R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and
$R^2$ is an acyl, substituted acyl, or an N-acyl derivative of a peptide;
or a salt, hydrate or solvate thereof.

The present disclosure provides Compound AM-1, and compositions and dose units comprising Compound AM-1:

Compound AM-1

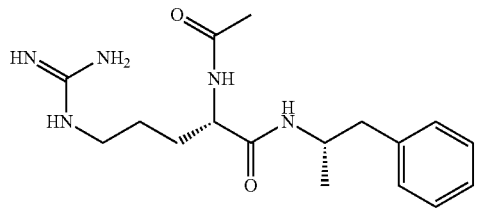

or a salt, hydrate or solvate thereof.

The present disclosure provides Compound AM-2, and compositions and dose units comprising Compound AM-2:

Compound AM-2

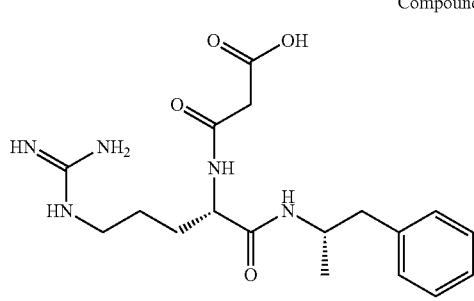

or a salt, hydrate or solvate thereof.

The present disclosure provides Compound AM-5, and compositions and dose units comprising Compound AM-5:

Compound AM-5

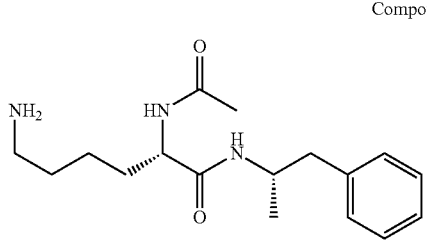

or a salt, hydrate or solvate thereof.

The present disclosure provides a compound of formula AM-(III), and compositions and dose units comprising a compound of formula AM-(III):

AM-(III)

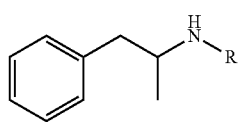

wherein
R is a GI enzyme-cleavable moiety.

The present disclosure provides a compound of formula AM-(IV), and compositions and dose units comprising a compound of formula AM-(IV):

AM-(IV)

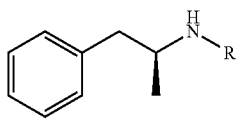

wherein
R is a GI enzyme-cleavable moiety.

The embodiments include methods for treating a patient comprising administering any of the compositions or dose units described herein to a patient in need thereof. The embodiments include methods to reduce side effects of a therapy comprising administering any of the compositions or dose units described herein to a patient in need thereof. The embodiments include methods of improving patient compliance with a therapy prescribed by a clinician comprising directing administration of any of the compositions or dose units described herein to a patient in need thereof. Such embodiments can provide for improved patient compliance with a prescribed therapy as compared to patient compliance with a prescribed therapy using drug and/or using prodrug without inhibitor as compared to prodrug with inhibitor.

The embodiments include methods of reducing risk of unintended overdose of amphetamine comprising directing administration of any of the pharmaceutical compositions or dose units described herein to a patient in need of treatment.

The embodiments include methods of making a dose unit comprising combining an amphetamine prodrug and a GI enzyme inhibitor in a dose unit, wherein the amphetamine prodrug and GI enzyme inhibitor are present in the dose unit in an amount effective to attenuate release of amphetamine from the amphetamine prodrug.

The embodiments include methods of deterring misuse or abuse of multiple dose units of an amphetamine prodrug comprising combining an amphetamine prodrug and a GI enzyme inhibitor in a dose unit, wherein the amphetamine prodrug and GI enzyme inhibitor are present in the dose unit in an amount effective to attenuate release of amphetamine from the amphetamine prodrug such that ingestion of multiples of dose units by a patient does not provide a proportional release of amphetamine. In further embodiments, release of drug is decreased compared to release of drug by an equivalent dosage of prodrug in the absence of inhibitor.

One embodiment is a method for identifying a prodrug and a GI enzyme inhibitor suitable for formulation in a dose unit. Such a method can be conducted as, for example, an in vitro assay, an in vivo assay, or an ex vivo assay.

The embodiments include methods for identifying an amphetamine prodrug and a GI enzyme inhibitor suitable for formulation in a dose unit comprising combining an amphetamine prodrug, a GI enzyme inhibitor, and a GI enzyme in a reaction mixture, and detecting amphetamine prodrug conversion, wherein a decrease in amphetamine prodrug conversion in the presence of the GI enzyme inhibitor as compared to amphetamine prodrug conversion in the absence of the GI enzyme inhibitor indicates the amphetamine prodrug and GI enzyme inhibitor are suitable for formulation in a dose unit.

The embodiments include methods for identifying an amphetamine prodrug and a GI enzyme inhibitor suitable for formulation in a dose unit comprising administering to an animal an amphetamine prodrug and a GI enzyme inhibitor and detecting amphetamine prodrug conversion, wherein a decrease in amphetamine conversion in the presence of the GI enzyme inhibitor as compared to amphetamine conversion in the absence of the GI enzyme inhibitor indicates the amphetamine prodrug and GI enzyme inhibitor are suitable for formulation in a dose unit. In certain embodiments, administering comprises administering to the animal increasing doses of inhibitor co-dosed with a selected fixed dose of amphetamine prodrug. Detecting prodrug conversion can facilitate identification of a dose of inhibitor and a dose of amphetamine prodrug that provides for a preselected pharmacokinetic (PK) profile. Such methods can be conducted as, for example, an in vivo assay or an ex vivo assay.

The embodiments include methods for identifying an amphetamine prodrug and a GI enzyme inhibitor suitable for formulation in a dose unit comprising administering to an animal tissue an amphetamine prodrug and a GI enzyme inhibitor and detecting amphetamine prodrug conversion, wherein a decrease in amphetamine prodrug conversion in the presence of the GI enzyme inhibitor as compared to amphetamine prodrug conversion in the absence of the GI enzyme inhibitor indicates the amphetamine prodrug and GI enzyme inhibitor are suitable for formulation in a dose unit.

BRIEF DESCRIPTION OF THE FIGURES

FIG. 4(a) shows a graph of mean plasma concentrations over time of amphetamine release following PO administration of increasing doses of Compound AM-1. FIG. 4(b) shows a graph of mean plasma concentrations over time of prodrug disappearance and of amphetamine release following PO administration of Compound AM-1.

FIG. 7(a) shows a graph of mean plasma concentrations over time of amphetamine release following PO administration of increasing doses of Compound AM-2. FIG. 7(b) shows a graph of mean plasma concentrations over time of prodrug disappearance and of amphetamine release following PO administration of Compound AM-2.

DEFINITIONS

Figure 1:
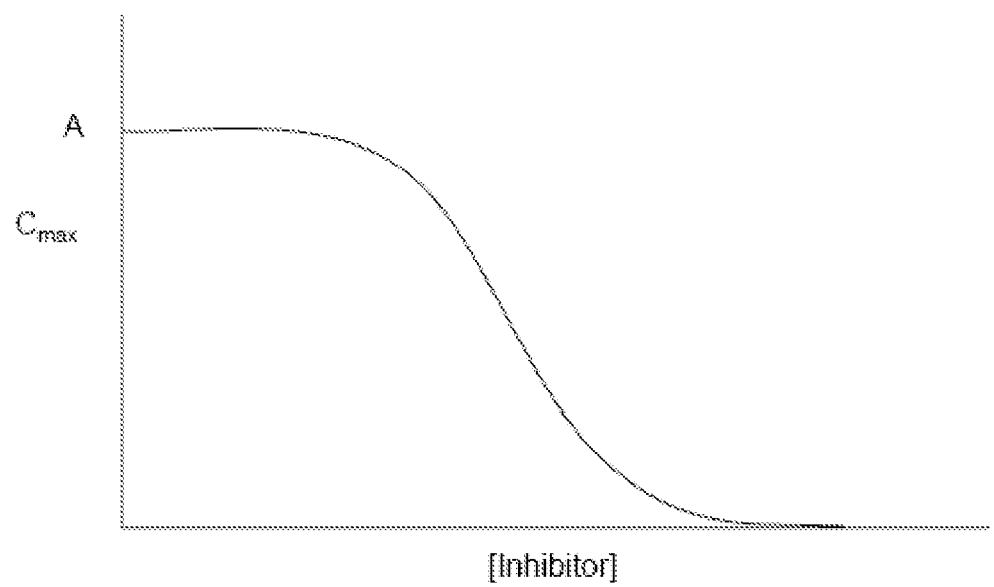
FIG. 1 is a schematic representing the effect of increasing the level of a GI enzyme inhibitor ("inhibitor", X-axis) on a PK parameter (e.g., drug Cmax) (Y-axis) for a fixed dose of prodrug. The effect of inhibitor upon a prodrug PK parameter can range from undetectable, to moderate, to complete inhibition (i.e., no detectable drug release).

The following terms have the following meaning unless otherwise indicated. Any undefined terms have their art recognized meanings.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —$C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —$C(O)OR^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^a$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group is specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to —O—, —S—, —S—S—, —O—S—, —$NR^{37}R^{38}$—, =N—N=, —N=N—, —N=N—$NR^{39}R^{40}$, —$PR^{41}$—, —P(O)$_2$—, —$POR^{42}$—, —O—P(O)$_2$—, —S—O—, —S—(O)—, —SO$_2$—, —$SnR^{43}R^{44}$— and the like, where $R^{37}$, $R^{38}$, $R^{39}$, $R^{40}$, $R^{41}$, $R^{42}$, $R^{43}$ and $R^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole. β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —O$^-$, =O, —$OR^{60}$, —$SR^{60}$, —S$^-$, =S, —$NR^{60}R^{61}$, =$NR^{60}$, —$CF_3$, —CN, —OCN, —SCN, —NO, —$NO_2$, =$N_2$, —$N_3$, —S(O)$_2$O$^-$, —S(O)$_2$OH, —S(O)$_2R^{60}$, —OS(O)$_2$O$^-$, —OS(O)$_2R^{60}$, —P(O)(O$^-$)$_2$, —P(O)(O$R^{60}$)(O$^-$), —OP(O)(O$R^{60}$)(O$R^{61}$), —C(O)$R^{60}$, —C(S)$R^{60}$, —C(O)O$R^{60}$, —C(O)$NR^{60}R^{61}$, —C(O)O$^-$, —C(S)O$R^{60}$, —$NR^{62}$C(O)$NR^{60}R^{61}$, —$NR^{62}$C(S)$NR^{60}R^{61}$, —$NR^{62}$C($NR^{63}$)$NR^{60}R^{61}$ and —C($NR^{62}$)$NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring.

In certain embodiments, substituents include -M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

"Dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"Pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax) and side effects.

"Gastrointestinal enzyme" or "GI enzyme" refers to an enzyme located in the gastrointestinal (GI) tract, which encompasses the anatomical sites from mouth to anus. Trypsin is an example of a GI enzyme.

"Gastrointestinal enzyme-cleavable moiety" or "GI enzyme-cleavable moiety" refers to a group comprising a site susceptible to cleavage by a GI enzyme. For example, a "trypsin-cleavable moiety" refers to a group comprising a site susceptible to cleavage by trypsin.

"Gastrointestinal enzyme inhibitor" or "GI enzyme inhibitor" refers to any agent capable of inhibiting the action of a gastrointestinal enzyme on a substrate. The term also encompasses salts of gastrointestinal enzyme inhibitors. For example, a "trypsin inhibitor" refers to any agent capable of inhibiting the action of trypsin on a substrate.

"Pharmaceutical composition" refers to at least one compound and can further comprise a pharmaceutically acceptable carrier, with which the compound is administered to a patient.

"Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Pharmaceutically acceptable carrier" refers to a diluent, adjuvant, excipient or vehicle with, or in which a compound is administered.

"Preventing" or "prevention" or "prophylaxis" refers to a reduction in risk of occurrence of a condition, such as ADHD, CFS, brain injury, narcolepsy, or obesity.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Treating" or "treatment" of any condition, such as ADHD, CFS, brain injury, narcolepsy, or obesity, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound (e.g. prodrug) that, when administered to a patient for preventing or treating a condition such as ADHD, CFS, brain injury, narcolepsy, or obesity, is sufficient to effect such treatment. The "therapeutically effective amount" will vary depending on the compound, the condition and its severity and the age, weight, etc., of the patient.

DETAILED DESCRIPTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a compound refers to one or more compounds. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. In certain instances, this nomenclature has been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{17}$O, $^{18}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Representative Embodiments

Reference will now be made in detail to various embodiments. It will be understood that the invention is not limited to these embodiments. To the contrary, it is intended to cover alternatives, modifications, and equivalents as may be included within the spirit and scope of the allowed claims.

The present disclosure provides pharmaceutical compositions, and their methods of use, where the pharmaceutical compositions comprise an amphetamine prodrug that provides enzymatically-controlled release of amphetamine or an amphetamine analog. The composition can further comprise an enzyme inhibitor that interacts with the enzyme(s) that mediates the enzymatically-controlled release of amphetamine or the amphetamine analog from the prodrug so as to attenuate enzymatic cleavage of the prodrug. In certain embodiments, the disclosure provides pharmaceutical compositions which comprise an enzyme inhibitor and an amphetamine prodrug that contains an enzyme-cleavable moiety that, when cleaved, releases amphetamine or the amphetamine analog.

According to one aspect, the embodiments include pharmaceutical compositions, which comprise a gastrointestinal GI enzyme-cleavable amphetamine prodrug and, optionally, a GI enzyme inhibitor. A "GI enzyme-cleavable amphetamine prodrug" is an amphetamine prodrug that comprises a promoiety comprising a GI enzyme-cleavable moiety. A GI enzyme-cleavable moiety has a site that is susceptible to cleavage by a GI enzyme. Examples of amphetamine prodrugs and enzyme inhibitors are described below.

Amphetamine Prodrugs

Amphetamine refers to a chemical substance that exerts its pharmacological action by modulating neurotransmitters, such as dopamine, serotonin and norepinephrine. In certain embodiments, amphetamine is a compound with a pharmacophore that crosses the blood-brain barrier and has CNS stimulation and central appetite suppressant effects. See, for example, Foye's Principles of Medicinal Chemistry, Sixth Edition, ed. T. L. Lemke and D. A. Williams, Lippincott Williams & Wilkins, 2008, particularly Chapter 13, pages 392-416.

The present disclosure provides an amphetamine prodrug which provides enzymatically-controlled release of amphetamine. The disclosure provides a promoiety that is attached to amphetamine through the amphetamine amino group.

"Amino-containing amphetamine analogs" or "amphetamine analogs" refer to analogs or derivatives of amphetamine that contain an amino group. For instance, the following amphetamine analogs contain an amino group that can be a point of attachment to a promoiety through the amino group: Benzedrine (i.e., dl-amphetamine), dextroamphetamine (i.e., d-amphetamine), levoamphetamine (i.e., l-amphetamine), 4-fluoroamphetamine (4-FA), 3-fluoroamphetamine (3-FA), 2-fluoroamphetamine (2-FA), 4-methylthioamphetamine (4-MTA), 3,4-methylenedioxyamphetamine (MDA), para-methoxyamphetamine (PMA), 3-methoxyamphetamine (3-MeOA), 4-ethoxyamphetamine (4-ETA), 2,5-dimethoxy-4-ethoxyamphetamine (MEM), 2,5-dimethoxy-4-propoxyamphetamine (MPM), 4-methylamphetamine (4-MA), 2-methylamphetamine (2-MA), 3-methylamphetamine (3-MA), 3,4-dimethylamphetamine, 3-methoxy-4-methylamphetamine (MMA), 3-trifluoromethylamphetamine, 3-hydroxyamphetamine, 4-hydroxyamphetamine, (1R,2S)-3-[-2-amino-1-hydroxy-propyl]phenol, 2,5-dimethoxy-4-methylamphetamine (DOM), 2,6-dimethoxy-4-methylamphetamine (Ψ-DOM), indanylamphetamine, 5-(2-aminopropyl)-2,3-dihydrobenzofuran (5-APDB), 6-(2-aminopropyl)-2,3-dihydrobenzofuran (6-APDB), 5-(2-aminopropyl)indole (5-IT), naphthylaminopropane (NAP), phenylpropanolamine (PPA), d-norpseudoephedrine, benzoylethanamine, para-bromoamphetamine (PBA), para-chloroamphetamine (PCA), para-iodoamphetamine (PIA), α,β-dimethylamphetamine, o-chloro-α,α-dimethylphenethylamine, 3,4-dihydroxyamphetamine (3,4-DHA), 2,4-dimethoxyamphetamine (2,4-DMA), 2,5-dimethoxyamphetamine (2,5-DMA), 3,4-dimethoxyamphetamine (3,4-DMA), α-methylnorepinephrine (α-Me-NE), 2,5-dimethoxy-4-methylthioamphetamine (Aleph), 2,5-dimethoxy-4-ethylthioamphetamine (Aleph-2), 2,5-dimethoxy-4-isopropylthioamphetamine (Aleph-4), 2,5-dimethoxy-4-phenylthioamphetamine (Aleph-6), 2,5-dimethoxy-4-propylthioamphetamine (Aleph-7), 2,5-dimethoxy-bromoamphetamine (DOB), 2,5-dimethoxychloroamphetamine (DOC), 2,5-dimethoxyfluoroethylamphetamine (DOEF) 2,5-dimethoxyethylamphetamine (DOET), 2,5-dimethoxyfluoroamphetamine (DOF), 2,5-dimethoxyiodoamphetamine (DOI), 2,5-dimethoxynitroamphetamine (DON), 2,5-dimethoxypropylamphetamine (DOPR), 2,5-dimethoxytrifluoromethylamphetamine (DOTFM), 2-methyl-3,4-methylenedioxyamphetamine (2-methyl-MDA), 3-methyl-4,5-methylenedioxyamphetamine (5-methyl-MDA), 3-methoxy-4,5-methylenedioxyamphetamine (MMDA), 2-methoxy-4,5-methylenedioxyamphetamine (MMDA-2), 2-methoxy-3,4-methylenedioxyamphetamine (MMDA-3a), 4-methoxy-2,3-methylenedioxyamphetamine (MMDA-3b), 2-methylthio-3,4-methylenethioxyamphetamine (2T-MMDA-3a), 2-methoxy-4,5-methylenethioxyamphetamine (4T-MMDA-2), 3,4,5-trimethoxyamphetamine (TMA), 2,4,5-trimethoxyamphetamine (TMA-2), 2,3,4-trimethoxyamphetamine (TMA-3), 2,3,5-trimethoxyamphetamine (TMA-4), 2,3,6-trimethoxyamphetamine (TMA-5), 2,4,6-trimethoxyamphetamine (TMA-6), 2,5-dimethoxy-3,4-dimethylamphetamine, 2,5-dimethoxy-3,4-methylenedioxyamphetamine (DMMDA), tyramine, phentermine, alpha-allyl-phenethylamine, (1-(8-bromobenzo[1,2-b;4,5-b]difuran-4-yl)-2-aminopropane (bromo-DragonFLY), 3,4,5-trimethoxyphenethylamine (mescaline), 2,5-dimethoxy-4-bromophenethylamine (2C-B), 2,5-dimethoxy-4-chlorophenethylamine (2C-C), 2,5-dimethoxy-4-iodophenethylamine (2C-I), 2,5-dimethoxy-4-methyl-phenethylamine (2C-D), 2,5-dimethoxy-4-ethylphenethylamine (2C-E), 2,5-dimethoxy-4-n-propylphenethylamine (2C-P), 2,5-dimethoxy-4-fluorophenethylamine (2C-F), 2,5-dimethoxy-4-nitrophenethylamine (2C-N), 2,5-dimethoxy-4-ethylthiophenethylamine (2C-T-2), 2,5-dimethoxy-4-isopropylthiophenethylamine (2C-T-4), 2,5-dimethoxy-4-propylthiophenethylamine (2C-T-7), 2,5-dimethoxy-4-cyclopropylmethylthio-phenethylamine (2C-T-8), 2,5-dimethoxy-4-tert-butylthio-phenethylamine (2C-T-9), 2,5-dimethoxy-4-(2-fluoroethylthio)-phenethylamine (2C-T-21), ephedrine, pseudoephedrine, and the like.

Any type of reactive group on an amphetamine analog can provide a handle for a point of attachment to a promoiety. Examples of reactive groups on an amphetamine analog include, but are not limited to, amino, amide, alcohol (including phenol), and ketone. In certain embodiments, an amino group on an amphetamine analog provides a point of attachment to a promoiety by reaction to form an amino linkage or an amide. For example, the amino group of the amphetamine analog can provide a point of attachment to a promoiety by reaction to form an amino linkage or an amide. An amide on an amphetamine analog can provide a point of attachment to a promoiety by reaction to form a linkage, such as an amide enol or an N-acylated amide. An alcohol (e.g., phenol) on an amphetamine analog can provide a point of attachment to a promoiety by reaction to form a linkage, such as a carbamate, a carbonate, an ether, or an ester. A ketone on an amphetamine analog can provide a point of attachment to a promoiety by reaction to form a linkage, such as an enol carbamate.

It is contemplated that amphetamine analogs bearing at least some of the functionalities described herein will be developed; such amphetamines are included as part of the scope of this disclosure.

The disclosure provides for an amphetamine prodrug, wherein amphetamine or the amphetamine analog has an optionally substituted amphetamine residue of the following general structure:

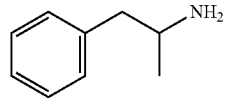

In certain embodiments, a promoiety can be attached to amphetamine or the amphetamine analog via modification of the amino moiety of the amphetamine residue. Release of amphetamine or the amphetamine analog is mediated by enzymatic cleavage of the promoiety from amphetamine or the amphetamine analog. In certain embodiments, a promoiety can be attached to amphetamine or the amphetamine analog through the amino moiety of the amphetamine residue, such as via a covalent bond. Release of amphetamine or the amphetamine analog is mediated by enzymatic cleavage of the promoiety from amphetamine or the amphetamine analog. In some cases, the promoiety comprises an enzyme-cleavable moiety that is susceptible to cleavage by a GI enzyme. Such cleavage can initiate, contribute to or effect drug release.

The disclosure provides an amphetamine prodrug which provides enzymatically-controlled release of amphetamine or an amphetamine analog. In an amphetamine prodrug, a promoiety is attached via modification of the amino moiety of the amphetamine residue, such as through an amino linkage or as an amide. Release of amphetamine or the amphetamine analog is mediated by enzymatic cleavage of the promoiety from amphetamine or the amphetamine analog. The disclosure provides for release of amphetamine or the amphetamine analog through enzyme cleavage of the promoiety from amphetamine or the amphetamine analog.

Formula AM-(I)

The present disclosure provides amphetamine prodrugs in which the promoiety is attached through the amino group of amphetamine. The disclosure provides compounds of the general formula AM-(I):

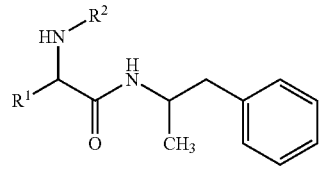

wherein
$R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and
$R^2$ is an acyl, substituted acyl, or an N-acyl derivative of a peptide;
or a salt, hydrate or solvate thereof.

Formula AM-(II)

The embodiments include a compound of formula AM-(II):

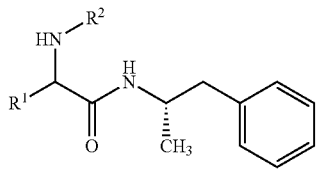

wherein
$R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and
$R^2$ is an acyl, substituted acyl, or an N-acyl derivative of a peptide;
or a salt, hydrate or solvate thereof.

In formulae AM-(I) and AM-(II), $R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl.

In certain instances, in formulae AM-(I) and AM-(II), $R^1$ is a side chain of an amino acid, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine. In certain instances, $R^1$ is a side chain of an L-amino acid, such as L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine or L-valine.

In certain instances, in formulae AM-(I) and AM-(II), $R^1$ is —$CH_2CH_2CH_2NH(C(=NH)(NH_2))$ or —$CH_2CH_2CH_2CH_2NH_2$. In certain instances, in formulae AM-(I) and AM-(II), $R^1$ is —$CH_2CH_2CH_2NH(C(=NH)(NH_2))$ or —$CH_2CH_2CH_2CH_2NH_2$, the configuration of the carbon atom to which $R^1$ is attached corresponding with that in an L-amino acid. In certain instances, in formulae AM-(I) and AM-(II), $R^1$ is —$CH_2CH_2CH_2NH(C(=NH)(NH_2))$, the configuration of the carbon atom to which $R^1$ is attached corresponding with that in an L-amino acid. In certain instances, in formulae AM-(I) and AM-(II), $R^1$ is —CH$_2$CH$_2$CH$_2$CH$_2$NH$_2$, the configuration of the carbon atom to which R$^1$ is attached corresponding with that in an L-amino acid.

In formulae AM-(I) and AM-(II), R$^2$ is an acyl, substituted acyl, or an N-acyl derivative of a peptide. In certain instances, R$^2$ is acyl. In certain instances, R$^2$ is substituted acyl. In certain instances, R$^2$ is acetyl, benzoyl, malonyl, piperonyl or succinyl. In certain instances, R$^2$ is acetyl, malonyl, or succinyl. In certain instances, R$^2$ is acetyl. In certain instances, R$^2$ is malonyl. In certain instances, R$^2$ is succinyl. In certain instances, R$^2$ is an N-acyl derivative of a peptide.

In certain instances, R$^2$ is a peptide of the formula (R$^4$)$_p$, wherein p is an integer from 1 to 100, and each R$^4$ is an independently selected amino acid, wherein the R$^4$ at the terminal end of the peptide is N-acylated. In certain instances, each R$^4$ is an independently selected L-amino acid. In certain instances, p is an integer from 1 to 90, 80, 70, 60, 50, 40, 30, 20, or 10. In certain instances, p is 1, 2, 3, 4, 5, 6, 7, 8, 9, or 10. In certain instances, the terminal end of the peptide is N-acylated, wherein the acyl group is acetyl, benzoyl, malonyl, piperonyl or succinyl. In certain instances, the terminal end of the peptide is N-acylated, wherein the acyl group is acetyl, malonyl, or succinyl. In certain instances, the terminal end of the peptide is N-acylated, wherein the acyl group is acetyl. In certain instances, the terminal end of the peptide is N-acylated, wherein the acyl group is malonyl. In certain instances, the terminal end of the peptide is N-acylated, wherein the acyl group is succinyl.

The disclosure provides for a compound of the following formula:

Compound AM-1

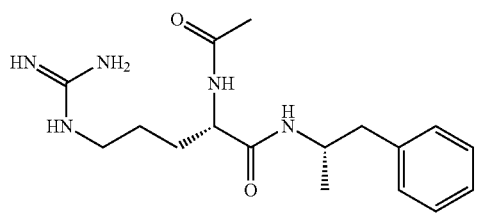

or a salt, hydrate or solvate thereof.

The disclosure provides for a compound of the following formula:

Compound AM-2

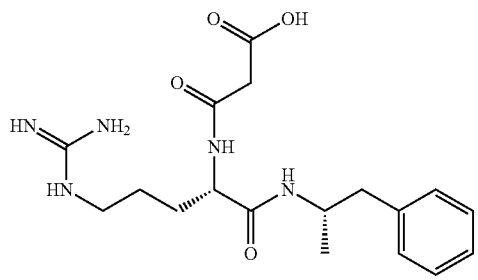

or a salt, hydrate or solvate thereof.

The disclosure provides for a compound of the following formula:

Compound AM-5

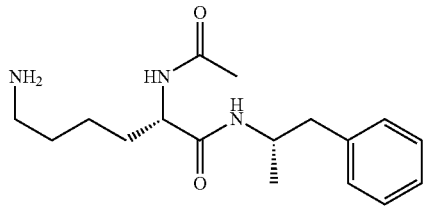

or a salt, hydrate or solvate thereof.

In certain embodiments, in formulae AM-(I) and AM-(II), —C(O)—CH(R$^1$)—NHR$^2$ is a GI enzyme-cleavable moiety. A GI enzyme-cleavable moiety is a structural moiety that is capable of being cleaved by a GI enzyme. In certain instances, a GI enzyme-cleavable moiety comprises a charged moiety that can fit into the active site of a GI enzyme and is able to orient the prodrug for cleavage at a scissile bond. For instance, the charged moiety can be a basic moiety that exists as a charged moiety at physiological pH.

For example, to form a GI enzyme-cleavable moiety, R$^1$ can include, but is not limited to, a side chain of lysine (such as L-lysine), a side chain of arginine (such as L-arginine), a side chain of homolysine, a side chain of homoarginine, and a side chain of ornithine. Other GI enzyme-cleavable moieties include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines and (bicyclo[2.2.2]octan-1-yl)methanamine and derivatives thereof.

In formulae AM-(I) and AM-(II), R$^2$ is selected from acyl, substituted acyl, and N-acyl derivative of a peptide. In certain instances, in formulae AM-(I) and AM-(II), R$^2$ is an N-acyl derivative of a peptide. The peptide may include one to 100 amino acids, where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

In certain embodiments, in formulae AM-(I) and AM-(II), —C(O)—CH(R$^1$)—NHR$^2$ is a trypsin-cleavable moiety. A trypsin-cleavable moiety is a structural moiety that is capable of being cleaved by trypsin. In certain instances, a trypsin-cleavable moiety comprises a charged moiety that can fit into an active site of trypsin and is able to orient the prodrug for cleavage at a scissile bond. For instance, the charged moiety can be a basic moiety that exists as a charged moiety at physiological pH.

In certain embodiments, in formulae AM-(I) and AM-(II), $R^1$ represents a side chain of an amino acid or a derivative of a side chain of an amino acid that effects —C(O)—CH($R^1$)—NH$R^2$ to be a trypsin-cleavable moiety. A derivative refers to a substance that has been altered from another substance by modification, partial substitution, homologation, truncation, or a change in oxidation state.

For example, to form a trypsin-cleavable moiety, $R^1$ can include, but is not limited to, a side chain of lysine (such as L-lysine), arginine (such as L-arginine), homolysine, homoarginine, and ornithine. Other values for $R^1$ include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines and (bicyclo[2.2.2]octan-1-yl)methanamine and derivatives thereof.

In certain instances, in formulae AM-(I) and AM-(II), $R^1$ represents —CH$_2$CH$_2$CH$_2$NH(C(=NH)(NH$_2$)) or —CH$_2$CH$_2$CH$_2$CH$_2$NH$_2$, the configuration of the carbon atom to which $R^1$ is attached corresponding with that in an L-amino acid.

In formulae AM-(I) and AM-(II), $R^2$ is selected from acyl, substituted acyl, and N-acyl derivative of a peptide. In certain instances, $R^2$ is an N-acyl derivative of an amino acid. In certain instances, $R^2$ is an N-acyl derivative of a peptide. The peptide may include one to 100 amino acids and where each amino acid can be selected independently, and where the terminal amino acid is an N-acyl amino acid. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

Formula AM-(III)

The present disclosure provides compounds of the general formula AM-(III):

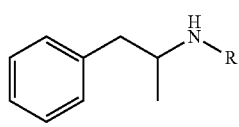

AM-(III)

wherein
R is a GI enzyme-cleavable moiety or a trypsin-cleavable moiety.

Formula AM-(IV)

The present disclosure provides compounds of the general formula AM-(IV):

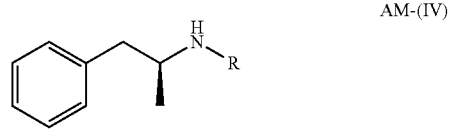

AM-(IV)

wherein
R is a GI enzyme-cleavable moiety or a trypsin-cleavable moiety.

In certain embodiments, in formulae AM-(III) and AM-(IV), R is a GI enzyme-cleavable moiety. A GI enzyme-cleavable moiety is a structural moiety that is capable of being cleaved by GI enzyme. In certain instances, a GI enzyme-cleavable moiety comprises a charged moiety that can fit into the active site of a GI enzyme and is able to orient the prodrug for cleavage at a scissile bond. For instance, the charged moiety can be a basic moiety that exists as a charged moiety at physiological pH.

In certain embodiments, in formulae AM-(III) and AM-(IV), R is —C(O)—CH($R^1$)—NH($R^2$), wherein $R^1$ represents a side chain of an amino acid or a derivative of a side chain of an amino acid that effects R to be a GI enzyme-cleavable moiety and $R^2$ is an acyl, substituted acyl, or an N-acyl derivative of a peptide. A derivative refers to a substance that has been altered from another substance by modification, partial substitution, homologation, truncation, or a change in oxidation state.

For example, to form a GI enzyme-cleavable moiety, $R^1$ can include, but is not limited to, a side chain of lysine (such as L-lysine), arginine (such as L-arginine), homolysine, homoarginine, and ornithine. Other values for R include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines, and (bicyclo[2,2,2]octan-1-yl)methanamine and derivatives thereof.

In certain embodiments, in formulae AM-(III) and AM-(IV), R is a trypsin-cleavable moiety. A trypsin-cleavable moiety is a structural moiety that is capable of being cleaved by trypsin. In certain instances, a trypsin-cleavable moiety comprises a charged moiety that can fit into an active site of trypsin and is able to orient the prodrug for cleavage at a scissile bond. For instance, the charged moiety can be a basic moiety that exists as a charged moiety at physiological pH.

In certain embodiments, in formulae AM-(III) and AM-(IV), R is —C(O)—CH($R^1$)—NH($R^2$), wherein $R^1$ represents a side chain of an amino acid or a derivative of a side chain of an amino acid that effects R to be a trypsin-cleavable moiety and $R^2$ is an acyl, substituted acyl, or an N-acyl derivative of a peptide. A derivative refers to a substance that has been altered from another substance by modification, partial substitution, homologation, truncation, or a change in oxidation state.

For example, to form a trypsin-cleavable moiety, $R^1$ can include, but is not limited to, a side chain of lysine (such as L-lysine), arginine (such as L-arginine), homolysine, homoarginine, and ornithine. Other values for R include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines and (bicyclo[2.2.2]octan-1-yl)methanamine and derivatives thereof.

In certain instances, in formulae AM-(III) and AM-(IV), $R^1$ is —$CH_2CH_2CH_2NH(C(=NH)(NH_2))$ or —$CH_2CH_2CH_2CH_2NH_2$, the configuration of the carbon atom to which $R^1$ is attached corresponding with that in an L-amino acid.

In certain embodiments, in formulae AM-(III) and AM-(IV), $R^2$ is acyl or substituted acyl. In certain instances, $R^2$ is an amino acid or an N-acyl derivative of an amino acid.

In certain instances, $R^2$ is an N-acyl derivative of a peptide. In some cases, the peptide comprises one to 100 amino acids and where each amino acid can be selected independently and the terminal amino acid is N-acylated. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

The present disclosure also provides pharmaceutical compositions comprising a pharmaceutically acceptable carrier and a therapeutically effective amount of a compound of formulae AM-(I) or AM-(II) or a pharmaceutically acceptable salt or solvate or stereoisomer thereof. In certain embodiments, the pharmaceutical composition comprises a compound of formula AM-(I). In certain embodiments, the pharmaceutical composition comprises a compound of formula AM-(II). The present disclosure also provides pharmaceutical compositions comprising a pharmaceutically acceptable carrier and a therapeutically effective amount of Compound AM-1, Compound AM-2, or Compound AM-5 or a pharmaceutically acceptable salt or solvate or stereoisomer thereof. In certain embodiments, the pharmaceutical composition comprises Compound AM-1. In certain embodiments, the pharmaceutical composition comprises Compound AM-2. In certain embodiments, the pharmaceutical composition comprises Compound AM-5.

The present disclosure also provides pharmaceutical compositions comprising a pharmaceutically acceptable carrier and a therapeutically effective amount of a compound of formulae AM-(III) or AM-(IV) or a pharmaceutically acceptable salt or solvate or stereoisomer thereof. In certain embodiments, the pharmaceutical composition comprises a compound of formula AM-(III). In certain embodiments, the pharmaceutical composition comprises a compound of formula AM-(IV).

General Synthetic Procedures for Compounds AM-1 and AM-2

The compounds described herein may be obtained via the routes generically illustrated in Scheme 1.

The promoieties described herein, may be prepared and attached to compounds containing amino groups by procedures known to those of skill in the art (See e.g., Green et al., "Protective Groups in Organic Chemistry," (Wiley, $2^{nd}$ ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, (Wiley Interscience); Trost et al., "Comprehensive Organic Synthesis," (Pergamon Press, 1991); "Theilheimer's Synthetic Methods of Organic Chemistry," Volumes 1-45, (Karger, 1991); March, "Advanced Organic Chemistry," (Wiley Interscience), 1991; Larock "Comprehensive Organic Transformations," (VCH Publishers, 1989); Paquette, "Encyclopedia of Reagents for Organic Synthesis," (John Wiley & Sons, 1995), Bodanzsky, "Principles of Peptide Synthesis," (Springer Verlag, 1984); Bodanzsky, "Practice of Peptide Synthesis," (Springer Verlag, 1984). Further, starting materials may be obtained from commercial sources or via well established synthetic procedures, supra.

Compounds AM-1 and AM-2 may be obtained via the routes generically illustrated in Scheme 1.

Scheme 1

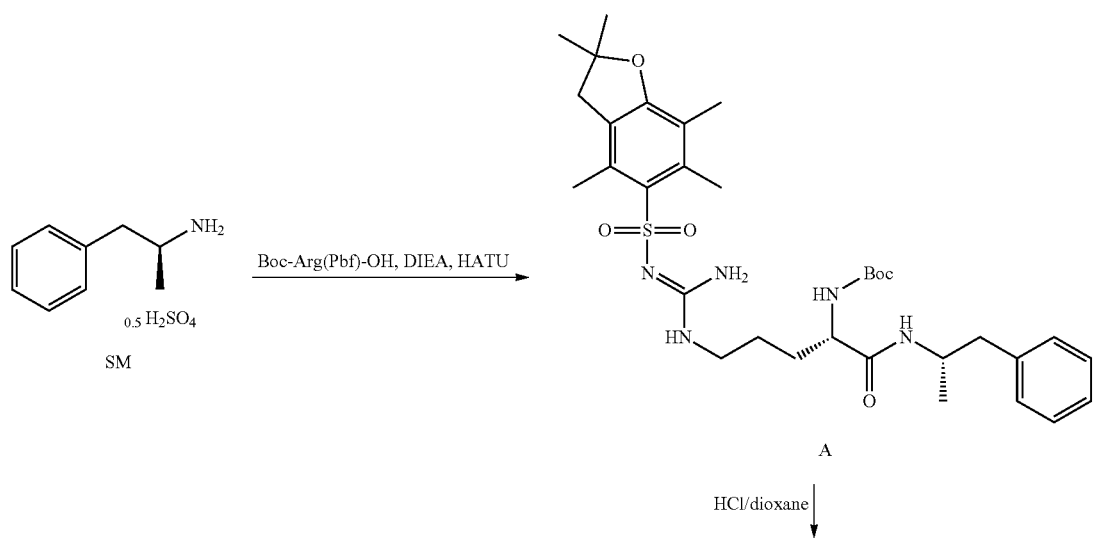

-continued

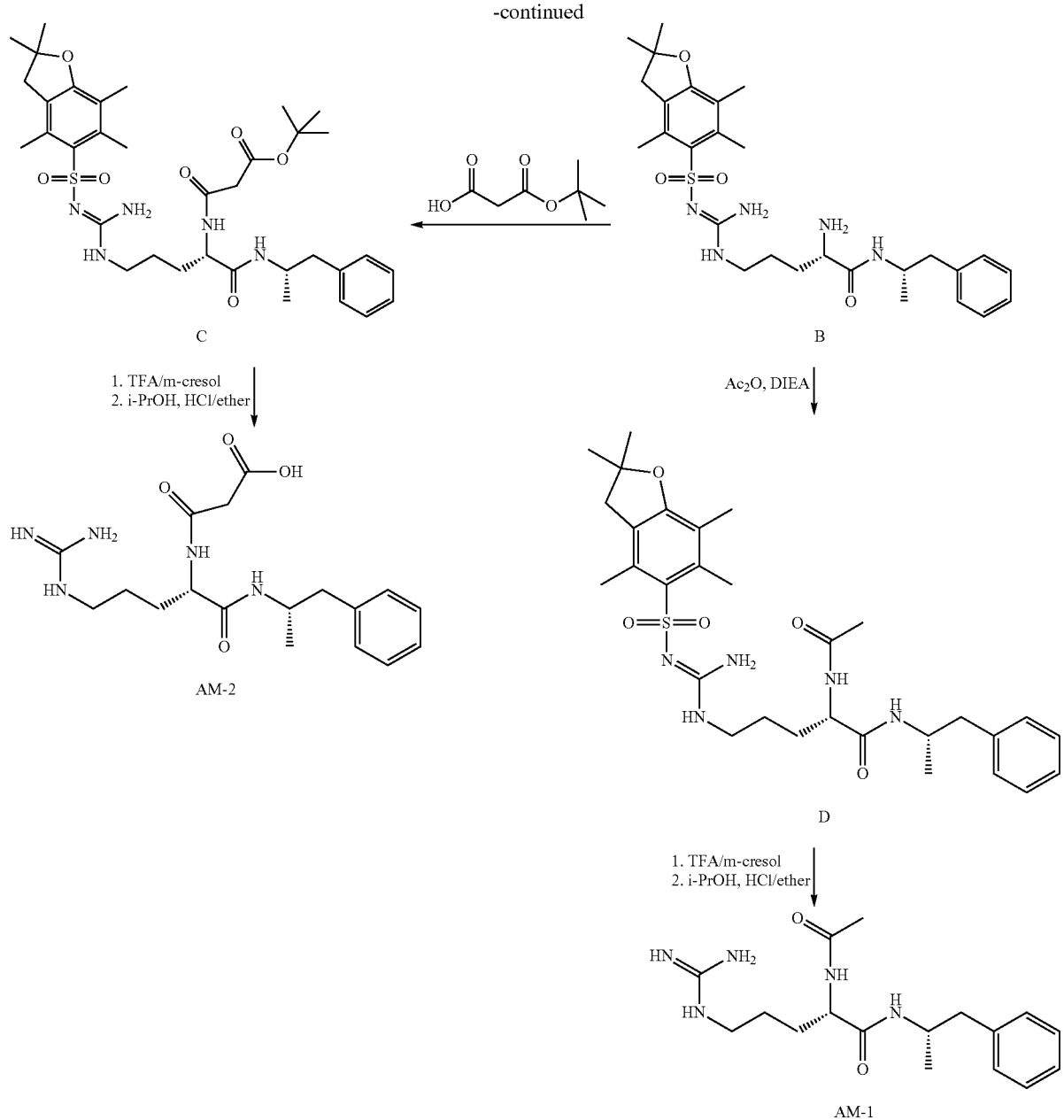

In Scheme 1, Compound SM is coupled with Boc-Arg (Pbf)-OH to form Compound A. Standard peptide coupling reagents can be used for the reaction. Suitable peptide coupling reagents include, but are not limited to, EDCI and HOBt, PyBroP and diisopropylethylamine, or HATU. Then, the Boc group of Compound A is removed to yield Compound B. The Boc group can be removed with acidic conditions. Suitable reagents that can be used for the deprotection reaction include trifluoroacetic acid and hydrochloric acid.

With further reference to Scheme 1, a malonyl group is attached to Compound B via a reaction with mono-tert-butyl malonate to form Compound C. Reaction between Compound B and mono-tert-butyl malonate can be aided with use of activation reagents, such as symmetric anhydrides, O-(benzotriazol-1-yl)-N,N,N',N'-tetramethyluronium hexafluorophosphate (HBTU), dicyclohexylcarbodiimide (DCC) diisopropylcarbodiimide (DIC)/1-hydroxybenzotriazole (HOBt), and benzotriazole-1-yl-oxytris(dimethylamino)phosphonium hexafluorophosphate (BOP).

Then, the Pbf group of Compound C is removed to yield Compound AM-2. The Pbf group and can be removed with acidic conditions. A suitable reagent that can be used for the deprotection reaction is trifluoroacetic acid.

In another synthetic route to obtain Compound AM-1, Compound B is acetylated at the amino group to yield Compound D. Acetylation of amino groups can be performed with acetic anhydride, acetic acid, or an acetyl halide.

Then, the Pbf group of Compound D is removed to yield Compound AM-1. The Pbf group and can be removed with acidic conditions. A suitable reagent that can be used for the deprotection reaction is trifluoroacetic acid.

Examples of Amphetamine Prodrugs

Examples of certain amphetamine prodrugs are shown below. In Formulae CC-(I) to CC-(IV), AA can represent a side chain of an amino acid. Amino acids, including amino acid variants, are discussed in a section herein.

Formula CC-(I)

A certain example is a compound of Formula CC-(I):

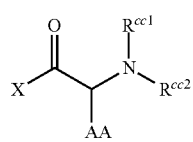
CC-(I)

wherein

X is an amphetamine, wherein a hydrogen atom of the amphetamine amino group is replaced by a covalent bond to —C(O)—C(AA)-NR$^{cc1}$R$^{cc2}$;

R$^{cc1}$ and R$^{cc2}$ are independently selected from hydrogen, alkyl, substituted alkyl, acyl, substituted acyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, substituted heteroarylalkyl; and AA is a side chain of an amino acid.

A certain formula of CC-(I) is shown below:

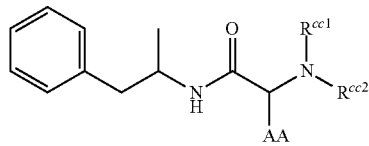

wherein

R$^{cc1}$ and R$^{cc2}$ are independently selected from hydrogen, alkyl, substituted alkyl, acyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and AA is a side chain of an amino acid.

Formula CC-(II)

A certain example is a compound of Formula CC-(II):

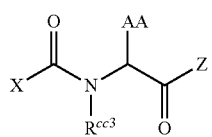
CC-(II)

wherein

X is an amphetamine, wherein a hydrogen atom of the amphetamine amino group is replaced by a covalent bond to —C(O)—NR$^{cc3}$—C(AA)-C(O)—Z;

R$^{cc3}$ is selected from hydrogen, alkyl, substituted alkyl, acyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

AA is a side chain of an amino acid; and

Z is selected from NH—R$^{cc4}$, O—R$^{cc4}$, OH and NH$_2$; and

R$^{cc4}$ is selected from hydrogen, alkyl, substituted alkyl, aryl, substituted aryl, acyl, arylalkyl and substituted arylalkyl.

A certain formula of CC-(II) is shown below:

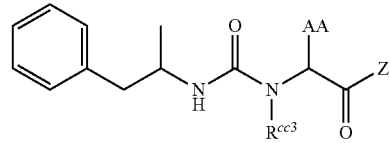

wherein

R$^{cc3}$ is selected from hydrogen, alkyl, substituted alkyl, acyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

AA is a side chain of an amino acid; and

Z is selected from NH—R$^{cc4}$, O—R$^{cc4}$, OH and NH$_2$; and

R$^{cc4}$ is selected from hydrogen, alkyl, substituted alkyl, aryl, substituted aryl, acyl, arylalkyl and substituted arylalkyl.

Formula CC-(III)

A certain example is a compound of Formula CC-(III):

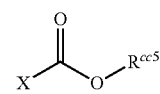
CC-(III)

wherein

X is an amphetamine, wherein a hydrogen atom of the amphetamine amino group is replaced by a covalent bond to —C(O)—O—NR$^{cc5}$; and

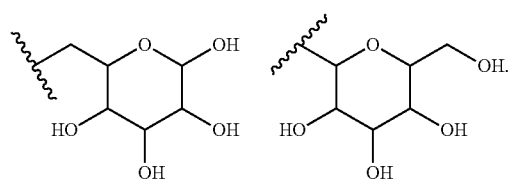 [SMILES: *CC1OC(O)C(O)C(O)C1O ; *C1OC(CO)C(O)C(O)C1O]

R$^{cc5}$ is selected from

A certain formula of CC-(III) is shown below:

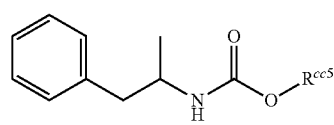

wherein

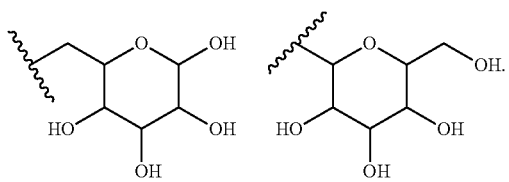 [SMILES: *CC1OC(O)C(O)C(O)C1O ; *C1OC(CO)C(O)C(O)C1O]

$R^{cc5}$ is selected from
Formula CC-(IV)

A certain example is a compound of Formula CC-(IV):

CC-(IV)

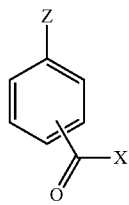

wherein

X is an amphetamine, wherein a hydrogen atom of the amphetamine amino group is replaced by a covalent bond to —C(O)—; and Z is amidino or guanidine.

A certain formula of CC-(IV) is shown below:

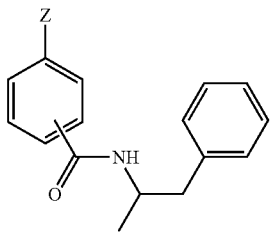

wherein

Z is amidino or guanidine.

Amino Acids Found in Prodrugs

"Amino acid" means a building block of a polypeptide. As used herein, "amino acid" includes the 20 common naturally occurring L-amino acids and all amino acids variants. In certain embodiments, an amino acid is a cleavable substrate for a gastrointestinal enzyme.

"Naturally occurring amino acids" means the 20 common naturally occurring L-amino acids, that is, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

"Amino acid variants" means an amino acid other than any of the 20 common naturally occurring L-amino acids that is hydrolysable by a protease in a manner similar to the ability of a protease to hydrolyze a naturally occurring L-amino acid. Amino acid variants, thus, include amino acids or analogs of amino acids other than the 20 naturally-occurring amino acids. Amino acid variants include synthetic amino acids. Amino acid variants also include amino acid derivatives. A derivative refers to a substance that has been altered from another substance by modification, partial substitution, homologation, truncation, or a change in oxidation state while retaining the ability to be cleaved by a GI enzyme.

Certain examples of amino acid variants include, but are not limited to: 2-aminoindane-2-carboxylic acid, 2-aminoisobutyric acid, 4-amino-phenylalanine, 5-hydroxylysine, biphenylalanine, citrulline, cyclohexylalanine, cyclohexylglycine, diethylglycine, dipropylglycine, homoarginine, homocitrulline, homophenylalanine, homoproline, homoserine, homotyrosine, hydroxyproline, lanthionine, naphthylalanine, norleucine, ornithine, phenylalanine(4-fluoro), phenylalanine(4-nitro), phenylglycine, pipecolic acid, tert-butylalanine, tert-butylglycine, tert-leucine, tetrahydroisoquinoline-3-carboxylic acid, α-aminobutyric acid, γ-amino butyric acid, 2,3-diaminoproprionic acid, phenylalanine(2,3,4,5,6 pentafluoro), aminohexanoic acid and derivatives thereof.

Certain examples of amino acid variants include, but are not limited to, N-methyl amino acids. For example, N-methyl-alanine, N-methyl aspartic acid, N-methyl-glutamic acid, N-methyl-glycine (sarcosine) are N-methyl amino acids.

Certain examples of amino acid variants include, but are not limited to: dehydroalanine, ethionine, hypusine, lanthionine, pyrrolysine, α-aminoisobutyric acid, selenomethionine and derivatives thereof.

Certain examples of amino acid variants include, but are not limited to: (3, 2-amino benzoic acid, 2-amino methyl benzoic acid, 2-amino-3-guanidinopropionic acid, 2-amino-3-methoxy benzoic acid, 2-amino-3-ureidopropionic acid, 3-amino benzoic acid, 4-amino benzoic acid, 4-amino methyl benzoic acid, 4-nitroanthranillic acid, 5-acetamido-2-aminobenzoic acid, butanoic acid (HMB), glutathione, homocysteine, statine, taurine, β-alanine, 2-hydroxy-4-(methylthio), (3,4)-diamino benzoic acid, (3,5)-diamino benzoic acid and derivatives thereof.

Certain examples of amino acid variants include, but are not limited to: (2 amino ethyl) cysteine, 2-amino-3-ethyoxybutanoic acid, buthionine, cystathion, cysteic acid, ethionine, ethoxytheorine, methylserine, N-ϵ-ϵ-dimethyl-lysine, N-ω-nitro-arginine, saccharopine, isoserine derivatives thereof, and combinations thereof.

Certain examples of amino acid variants include, but are not limited to: l-carnitine, selenocysteine, l-sarcosine, l-lysinol, benzoic acid, citric acid, choline, EDTA or succinic acid and derivatives thereof.

Certain examples of amino acid variants are amino alcohols. Examples of amino alcohols include, but are not limited to: alaninol, indano, norephedrine, asparaginol, aspartimol, glutamol, leucinol, methioninol, phenylalaninol, prolinol, tryptophanol, valinol, isoleucinol, argininol, serinol, tyrosinol, threoninol, cysteinol, lysinol, histidinol and derivatives thereof.

Enzyme Inhibitors

The enzyme capable of cleaving the enzymatically-cleavable moiety of an amphetamine prodrug or amphetamine analog prodrug can be a peptidase, also called a protease. In certain embodiments, the enzyme is an enzyme located in the gastrointestinal (GI) tract, i.e., a gastrointestinal enzyme, or a GI enzyme. The enzyme can be a digestive enzyme such as a gastric, intestinal, pancreatic or brush border enzyme or enzyme of GI microbial flora, such as those involved in peptide hydrolysis. Examples include a pepsin, such as pepsin A or pepsin B; a trypsin; a chymotrypsin; an elastase; a carboxypeptidase, such as carboxypeptidase A or carboxypeptidase B; an aminopeptidase (such as aminopeptidase N or aminopeptidase A; an endopeptidase; an exopeptidase; a dipeptidylaminopeptidase such as dipeptidylaminopeptidase IV; a dipeptidase; a tripeptidase; or an enteropeptidase. In certain embodiments, the enzyme is a cytoplasmic protease located on or in the GI brush border. In certain embodiments, the enzyme is trypsin. Accordingly, in certain embodiments, the corresponding composition is administered orally to the patient.

The disclosure provides for a composition comprising a GI enzyme inhibitor. Such an inhibitor can inhibit at least one of any of the GI enzymes disclosed herein. An example of a GI enzyme inhibitor is a protease inhibitor, such as a trypsin inhibitor.

As used herein, the term "GI enzyme inhibitor" refers to any agent capable of inhibiting the action of a GI enzyme on a substrate. The ability of an agent to inhibit a GI enzyme can be measured using assays well known in the art.

In certain embodiments, the GI enzyme capable of cleaving the enzymatically-cleavable moiety may be a protease—the promoiety comprising the enzymatically-cleavable moiety being linked to the amphetamine or prodrug through an amide (e.g., a peptide: —NHC(O)—) bond. The disclosure provides for inhibitors of proteases.

Proteases can be classified as exopeptidases or endopeptidases. Examples of exopeptidases include aminopeptidase and carboxypeptidase (A, B, or Y). Examples of endopeptidases include trypsin, chymotrypsin, elastase, pepsin, and papain. The disclosure provides for inhibitors of exopeptidase and endopeptidase.

In some embodiments, the enzyme is a digestive enzyme of a protein. The disclosure provides for inhibitors of digestive enzymes. A gastric phase involves stomach enzymes, such as pepsin. An intestinal phase involves enzymes in the small intestine duodenum, such as trypsin, chymotrypsin, elastase, carboxypeptidase A, and carboxypeptidase B. An intestinal brush border phase involves enzymes in the small intestinal brush border, such as aminopeptidase N, aminopeptidase A, endopeptidases, dipeptidases, dipeptidylaminopeptidase, and dipeptidylaminopeptidase IV. An intestinal intracellular phase involves intracellular peptidases, such as dipeptidases (i.e., iminopeptidase) and aminopeptidase.

In certain embodiments, the enzyme inhibitor in the disclosed compositions is a peptidase inhibitor or protease inhibitor. In certain embodiments, the enzyme is a digestive enzyme such as a gastric, pancreatic or brush border enzyme, such as those involved in peptide hydrolysis. Examples include pepsin, trypsin, chymotrypsin, colipase, elastase, aminopeptidase N, aminopeptidase A, dipeptidylaminopeptidase IV, tripeptidase or enteropeptidase.

Proteases can be inhibited by naturally occurring peptide or protein inhibitors, or by small molecule naturally occurring or synthetic inhibitors. Examples of protein or peptide inhibitors that are protease inhibitors include, but are not limited to, α1-antitrypsin from human plasma, aprotinin, trypsin inhibitor from soybean (SBTI), Bowman-Birk Inhibitor from soybean (BBSI), trypsin inhibitor from egg white (ovomucoid), chromostatin, and potato-derived carboxypeptidase inhibitor. Examples of small molecule irreversible inhibitors that are protease inhibitors include, but are not limited to, TPCK (1-chloro-3-tosylamido-4-phenyl-2-butanone), TLCK (1-chloro-3-tosylamido-7-amino-2-heptone), and PMSF (phenylmethyl sulfonyl floride). Examples of small molecule irreversible inhibitors that are protease inhibitors include, but are not limited to benzamidine, apixaban, camostat, 3,4-dichloroisocoumarin, ε-aminocaprionic acid, amastatin, lysianadioic acid, 1,10-phenanthroline, cysteamine, and bestatin. Other examples of small molecule inhibitors are Compound 101, Compound 102, Compound 103, Compound 104, Compound 105, Compound 106, Compound 107, Compound 108, Compound 109 and Compound 110, described in more detail below.

The following table shows examples of gastrointestinal (GI) proteases, examples of their corresponding substrates, and examples of corresponding inhibitors.

| Table of Examples of GI Proteases and Corresponding Susbtrates and Inhibitors | | |
|---|---|---|
| GI Protease | Substrates | Inhibitors |
| Trypsin | $R_{n-1}$ = Arg, Lys, positively charged residues | TLCK, Benzamidine, Apixaban, Bowman Birk |
| Chymotrypsin | $R_{n-1}$ = Phe, Tyr, Trp, bulky hydrophobic residues | ε-Aminocaprionic TPCK Bowman-Birk |
| Pepsin | $R_n$ = Leu, Phe, Trp, Tyr | Pepstatin, PMSF |
| Carboypeptidase B | $R_n$ = Arg, Lys | Potato-derived inhibitor, Lysianadioic acid |
| Carboypeptidase A | $R_n$ not = Arg, Lys | Potato-derived inhibitor, 1,10-phenanthroline |
| Elastase | $R_{n-1}$ = Ala, Gly, Ser, small neutral residues | α1-antitrypsin, 3,4-dichlorocoumarin |
| Aminopeptidase | All free N-terminal AA | Bestatin, Amastatin |

Trypsin Inhibitors

As used herein, the term "trypsin inhibitor" refers to any agent capable of inhibiting the action of trypsin on a substrate. The term "trypsin inhibitor" also encompasses salts of trypsin inhibitors. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, *J. Biol. Chem.* 241, 3955 and Y. Birk, 1976, Meth. Enzymol. 45, 700. In certain instances, a trypsin inhibitor can interact with an active site of trypsin, such as the S1 pocket and the S3/4 pocket. The S1 pocket has an aspartate residue which has affinity for positively charged moiety. The S3/4 pocket is a hydrophobic pocket. The disclosure provides for specific trypsin inhibitors and non-specific serine protease inhibitors.

There are many trypsin inhibitors known in the art, both those specific to trypsin and those that inhibit trypsin and other proteases such as chymotrypsin. The disclosure provides for trypsin inhibitors that are proteins, peptides, and small molecules. The disclosure provides for trypsin inhibitors that are irreversible inhibitors or reversible inhibitors. The disclosure provides for trypsin inhibitors that are competitive inhibitors, non-competitive inhibitors, or uncompetitive inhibitors. The disclosure provides for natural, synthetic or semi-synthetic trypsin inhibitors.

Trypsin inhibitors can be derived from a variety of animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, *Meth. Enzymol.* 45, 678.

In one embodiment, the trypsin inhibitor is derived from soybean. Trypsin inhibitors derived from soybean (*Glycine max*) are readily available and are considered to be safe for human consumption. They include, but are not limited to, SBTI, which inhibits trypsin, and Bowman-Birk inhibitor, which inhibits trypsin and chymotrypsin. Such trypsin inhibitors are available, for example from Sigma-Aldrich, St. Louis, Mo., USA.

A trypsin inhibitor can be an arginine mimic or lysine mimic, either natural or synthetic compound. In certain embodiments, the trypsin inhibitor is an arginine mimic or a lysine mimic, wherein the arginine mimic or lysine mimic is a synthetic compound. As used herein, an arginine mimic or lysine mimic can include a compound capable of binding to the P$^1$ pocket of trypsin and/or interfering with trypsin active site function. The arginine or lysine mimic can be a cleavable or non-cleavable moiety.

Examples of trypsin inhibitors, which are arginine mimics and/or lysine mimics, include, but not limited to, arylguanidine, benzamidine, 3,4-dichloroisocoumarin, diisopropylfluorophosphate, gabexate mesylate, and phenylmethanesulfonyl fluoride, or substituted versions or analogs thereof. In certain embodiments, trypsin inhibitors comprise a covalently modifiable group, such as a chloroketone moiety, an aldehyde moiety, or an epoxide moiety. Other examples of trypsin inhibitors are aprotinin, camostat and pentamidine.

Other examples of trypsin inhibitors include compounds of formula:

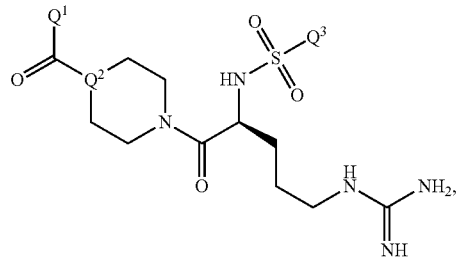

wherein:
$Q^1$ is selected from —O-$Q^4$ or -$Q^4$-COOH, where $Q^4$ is $C_1$-$C_4$ alkyl;
$Q^2$ is N or CH; and
$Q^3$ is aryl or substituted aryl.

Certain trypsin inhibitors include compounds of formula:

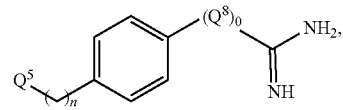

wherein:
$Q^5$ is —C(O)—COOH or —NH-$Q^6$-$Q^7$-$SO_2$—$C_6H_5$, where
$Q^6$ is —$(CH_2)_p$—COOH;
$Q^7$ is —$(CH_2)_r$—$C_6H_5$;
$Q^8$ is NH;
n is an integer from zero to two;
o is zero or one;
p is an integer from one to three; and
r is an integer from one to three.

Other examples of trypsin inhibitors include compounds of formula:

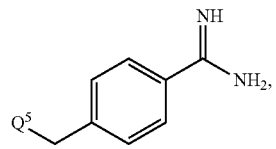

wherein:
$Q^5$ is —C(O)—COOH or —NH-$Q^6$-$Q^7$-$SO_2$—$C_6H_5$, where
$Q^6$ is —$(CH_2)_p$—COOH;
$Q^7$ is —$(CH_2)_r$—$C_6H_5$; and
p is an integer from one to three; and
r is an integer from one to three.

Certain trypsin inhibitors include the following:

| Compound | | |
|---|---|---|
| 101 | 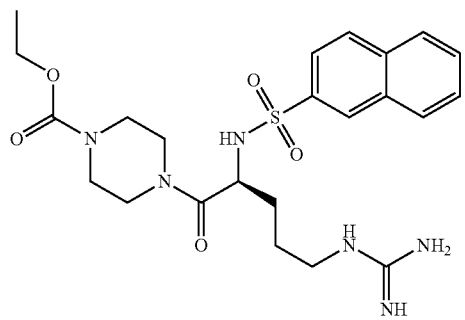 [SMILES: CCOC(=O)N1CCN(C(=O)[C@H](CCCNC(=N)N)NS(=O)(=O)c2ccc3ccccc3c2)CC1] | (S)-ethyl 4-(5-guanidino-2-(naphthalene-2-sulfonamido)pentanoyl)piperazine-1-carboxylate |

-continued

| | | |
|---|---|---|
| Compound 102 | 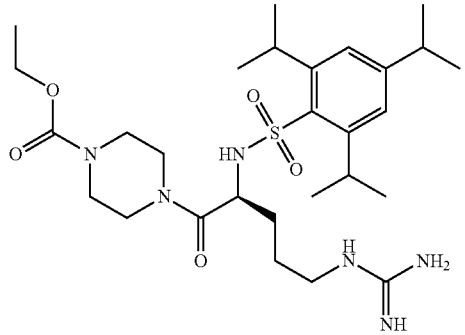 [SMILES: CCOC(=O)N1CCN(C(=O)[C@H](CCCNC(=N)N)NS(=O)(=O)c2c(C(C)C)cc(C(C)C)cc2C(C)C)CC1] | (S)-ethyl 4-(5-guanidino-2-(2,4,6-triisopropylphenylsulfonamido)pentanoyl)piperazine-1-carboxylate |
| Compound 103 | 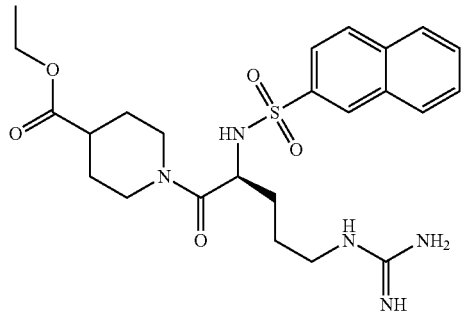 [SMILES: CCOC(=O)C1CCN(C(=O)[C@H](CCCNC(=N)N)NS(=O)(=O)c2ccc3ccccc3c2)CC1] | (S)-ethyl 1-(5-guanidino-2-(naphthalene-2-sulfonamido)pentanoyl)piperidine-4-carboxylate |
| Compound 104 | 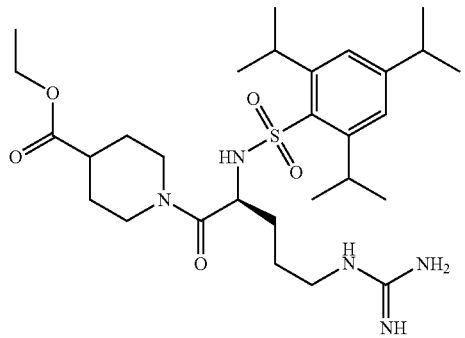 [SMILES: CCOC(=O)C1CCN(C(=O)[C@H](CCCNC(=N)N)NS(=O)(=O)c2c(C(C)C)cc(C(C)C)cc2C(C)C)CC1] | (S)-ethyl 1-(5-guanidino-2-(2,4,6-triisopropylphenylsulfonamido)pentanoyl)piperidine-4-carboxylate |
| Compound 105 | 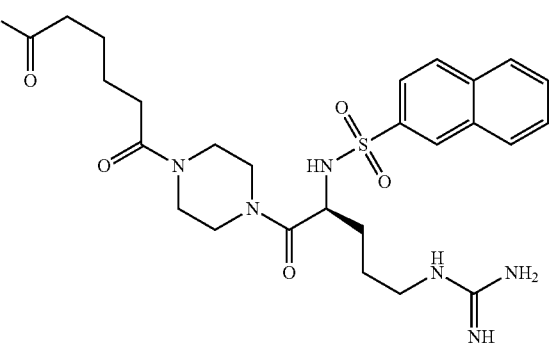 | (S)-6-(4-(5-guanidino-2-(naphthalene-2-sulfonamido)pentanoyl)piperazin-1-yl)-6-oxohexanoic acid |
| Compound 106 | 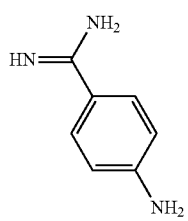 | 4-aminobenzimidamide (also 4-aminobenzamidine) |

| Compound 107 | ![structure] | 3-(4-carbamimidoylphenyl)-2-oxopropanoic acid |
| Compound 108 | ![structure] | (S)-5-(4-carbamimidoylbenzylamino)-5-oxo-4-((R)-4-phenyl-2-(phenylmethylsulfonamido)butanamido)pentanoic acid |
| Compound 109 | ![structure] | 6-carbamimidoylnaphthalen-2-yl 4-(diaminomethyleneamino)benzoate |
| Compound 110 | ![structure] | 4,4'-(pentane-1,5-diylbis(oxy))dibenzimidamide |

In certain embodiments, the trypsin inhibitor is SBTI, BBSI, Compound 101, Compound 106, Compound 108, Compound 109, or Compound 110. In certain embodiments, the trypsin inhibitor is camostat. In certain embodiments, the trypsin inhibitor is Compound 109.

In certain embodiments, the trypsin inhibitor is a compound of formula T-I:

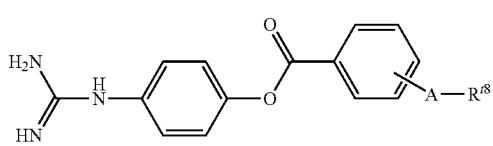

(T-I)

wherein
A represents a group of the following formula:

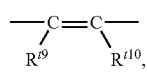

$R^{t9}$ and $R^{t10}$ each represents independently a hydrogen atom or a $C_{1-4}$ alkyl group, $R^{t8}$ represents a group selected from the following formulae:

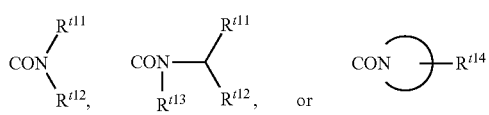

wherein $R^{t11}$, $R^{t12}$ and $R^{t13}$ each represents independently
(1) a hydrogen atom,
(2) a phenyl group,
(3) a $C_{1-4}$ alkyl group substituted by a phenyl group,
(4) a $C_{1-10}$ alkyl group,
(5) a $C_{1-10}$ alkoxyl group,
(6) a $C_{2-10}$ alkenyl group having 1 to 3 double bonds,
(7) a $C_{2-10}$ alkynyl group having 1 to 2 triple bonds,
(8) a group of formula: $R^{t15}$—C(O)X$R^{t16}$,
wherein $R^{t15}$ represents a single bond or a $C_{1-8}$ alkylene group, X represents an oxygen atom or an NH-group, and
$R^{t16}$ represents a hydrogen atom, a $C_{1-4}$ alkyl group, a phenyl group or a $C_{1-4}$ alkyl group substituted by a phenyl group, or
(9) a $C_{3-7}$ cycloalkyl group;

the structure represents a 4-7 membered monocyclic hetero-ring containing 1 to 2 nitrogen or oxygen atoms,
$R^{t14}$ represents a hydrogen atom, a $C_{1-4}$ alkyl group substituted by a phenyl group or a group of formula: $COOR^{t17}$, wherein $R^{t17}$ represents a hydrogen atom, a $C_{1-4}$ alkyl group or a $C_{1-4}$ alkyl group substituted by a phenyl group;
provided that $R^{t11}$, $R^{t12}$ and $R^{t13}$ do not represent simultaneously hydrogen atoms;
or nontoxic salts, acid addition salts or hydrates thereof.

In certain embodiments, the trypsin inhibitor is a compound selected from the following:

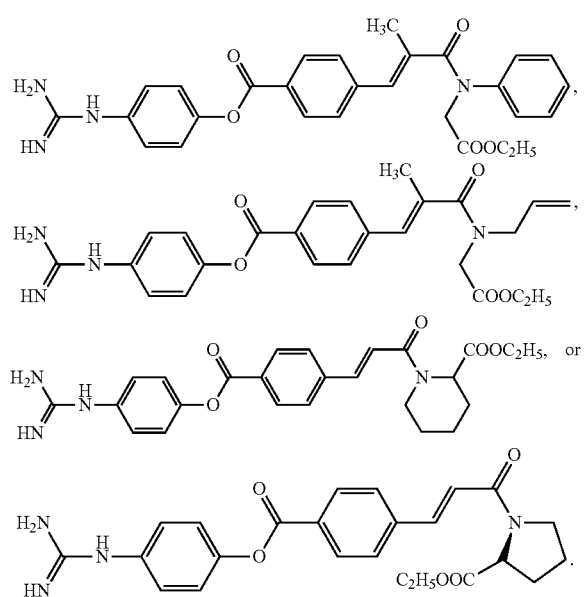

In certain embodiments, the trypsin inhibitor is a compound of formula T-II:

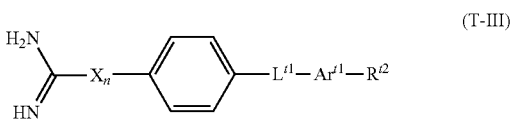

(T-II)

wherein
X is NH;
n is zero or one; and
$R^{t1}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —$(CH_2)_m$—C(O)—O—$(CH_2)_m$—C(O)—N—$R^{n1}R^{n2}$, wherein each m is independently an integer from zero to 2; and $R^{n1}$ and $R^{n2}$ are independently selected from hydrogen and $C_{1-4}$ alkyl.

In certain embodiments, in formula T-II, $R^{t1}$ is guanidino or amidino.

In certain embodiments, in formula T-II, $R^{t1}$ is —$(CH_2)_m$—C(O)—O—$(CH_2)_m$—C(O)—N—$R^{n1}R^{n2}$, wherein m is one and $R^{n1}$ and $R^{n2}$ are methyl.

In certain embodiments, the trypsin inhibitor is a compound of formula T-III:

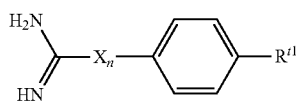

(T-III)

wherein
X is NH;
n is zero or one;
$L^{t1}$ is selected from —C(O)—O—; —O—C(O)—; —O—$(CH_2)_m$—O—; —$OCH_2$—$Ar^{t2}$—$CH_2O$—; —C(O)—$NR^{t3}$—; and —$NR^{t3}$—C(O)—;
$R^{t3}$ is selected from hydrogen, $C_{1-6}$ alkyl, and substituted $C_{1-6}$ alkyl;
$Ar^{t1}$ and $Ar^{t2}$ are each independently a substituted or unsubstituted aryl group;
m is an integer from 1 to 3; and
$R^{t2}$ is selected from hydrogen, halogen, nitro, alkyl, substituted alkyl, alkoxy, carboxyl, alkoxycarbonyl, acyl, aminoacyl, guanidino, amidino, carbamide, amino, substituted amino, hydroxyl, cyano and —$(CH_2)_m$—C(O)—O—$(CH_2)_m$—C(O)—N—$R^{n1}R^{n2}$, wherein each m is independently an integer from zero to 2; and $R^{n1}$ and $R^{n2}$ are independently selected from hydrogen and $C_{1-4}$ alkyl.

In certain embodiments, in formula T-III, $R^{t2}$ is guanidino or amidino.

In certain embodiments, in formula T-III, $R^{t2}$ is —$(CH_2)_m$—C(O)—O—$(CH_2)$—C(O)—N—$R^{n1}R^{n2}$, wherein m is one and $R^{n1}$ and $R^{n2}$ are methyl.

In certain embodiments, the trypsin inhibitor is a compound of formula T-IV:

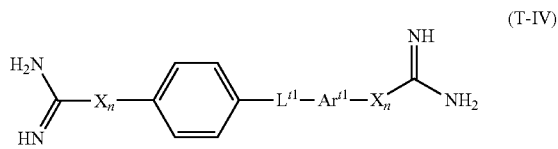

(T-IV)

wherein
each X is NH;
each n is independently zero or one;
$L^{t1}$ is selected from —C(O)—O—; —O—C(O)—; —O—$(CH_2)_m$—O—; —$OCH_2$—$Ar^{t2}$—$CH_2O$—; —C(O)—$NR^{t3}$—; and —$NR^{t3}$—C(O)—;
$R^{t3}$ is selected from hydrogen, $C_{1-6}$ alkyl, and substituted $C_{1-6}$ alkyl;
$Ar^{t1}$ and $Ar^{t2}$ are each independently a substituted or unsubstituted aryl group; and
m is an integer from 1 to 3.

In certain embodiments, in formula T-IV, $Ar^{t1}$ or $Ar^{t2}$ is phenyl.

In certain embodiments, in formula T-IV, $Ar^{t1}$ or $Ar^{t2}$ is naphthyl.

In certain embodiments, the trypsin inhibitor is Compound 109.

In certain embodiments, the trypsin inhibitor is

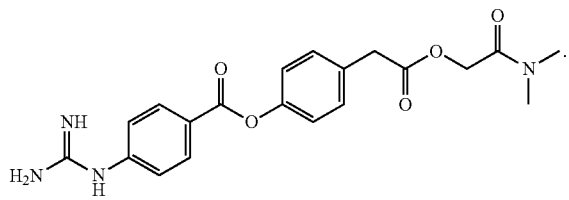 [SMILES: CN(C)C(=O)COC(=O)Cc1ccc(OC(=O)c2ccc(NC(=N)N)cc2)cc1]

In certain embodiments, the trypsin inhibitor is Compound 110 or a bis-arylamidine variant thereof; see, for example, J. D. Geratz, M. C.-F. Cheng and R. R. Tidwell (1976) *J Med. Chem.* 19, 634-639.

It will be appreciated that the pharmaceutical composition according to the embodiments may further comprise one or more additional trypsin inhibitors.

It is to be appreciated that the invention also includes inhibitors of other enzymes involved in protein assimilation that can be used in combination with a prodrug disclosed herein comprising an amino acid of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine or amino acid variants thereof.

Combinations of Amphetamine Prodrugs and Enzyme Inhibitors

As discussed above, the present disclosure provides pharmaceutical compositions which comprise an enzyme inhibitor and an amphetamine prodrug that contains an enzyme-cleavable moiety that, when cleaved, facilitates release of amphetamine.

Examples of compositions containing an amphetamine prodrug and an enzyme inhibitor (e.g., a trypsin inhibitor) are described below.

Combinations of Formulae AM-(I) to AM-(II) and Enzyme Inhibitor

The embodiments provide a pharmaceutical composition, which comprises an enzyme inhibitor and a compound of general Formulae AM-(I) to AM-(IV), or a pharmaceutically acceptable salt thereof.

The embodiments provide a pharmaceutical composition, which comprises a compound of Formulae T-I to T-IV and a compound of general Formulae AM-(I) to AM-(IV), or a pharmaceutically acceptable salt thereof. The embodiments provide a pharmaceutical composition, which comprises Compound 109 and a compound of general Formulae AM-(I) to AM-(IV), or a pharmaceutically acceptable salt thereof.

Certain embodiments provide for a combination of a compound of Formula AM-(I) and an enzyme inhibitor. In certain embodiments, combinations of a compound of Formula AM-(I) and an enzyme inhibitor include, but are not limited to the following: a compound of Formula AM-(I) and SBTI; a compound of Formula AM-(I) and BBSI; a compound of Formula AM-(I) and Compound 101; a compound of Formula AM-(I) and Compound 106; a compound of Formula AM-(I) and Compound 108; a compound of Formula AM-(I) and Compound 109; a compound of Formula AM-(I) and Compound 110; or a pharmaceutically acceptable salt thereof; and the like.

Certain embodiments provide for a combination of a compound of Formula AM-(II) and an enzyme inhibitor. In certain embodiments, combinations of a compound of Formula AM-(II) and an enzyme inhibitor include, but are not limited to the following: a compound of Formula AM-(II) and SBTI; a compound of Formula AM-(II) and BBSI; a compound of Formula AM-(II) and Compound 101; a compound of Formula AM-(II) and Compound 106; a compound of Formula AM-(II) and Compound 108; a compound of Formula AM-(II) and Compound 109; a compound of Formula AM-(II) and Compound 110; or a pharmaceutically acceptable salt thereof; and the like.

Certain embodiments provide for a combination of a compound of Formula AM-(III) and an enzyme inhibitor. In certain embodiments, combinations of a compound of Formula AM-(III) and an enzyme inhibitor include, but are not limited to the following: a compound of Formula AM-(III) and SBTI; a compound of Formula AM-(III) and BBSI; a compound of Formula AM-(III) and Compound 101; a compound of Formula AM-(III) and Compound 106; a compound of Formula AM-(III) and Compound 108; a compound of Formula AM-(III) and Compound 109; a compound of Formula AM-(III) and Compound 110; or a pharmaceutically acceptable salt thereof; and the like.

Certain embodiments provide for a combination of a compound of Formula AM-(IV) and an enzyme inhibitor. In certain embodiments, combinations of a compound of Formula AM-(IV) and an enzyme inhibitor include, but are not limited to the following: a compound of Formula AM-(IV) and SBTI; a compound of Formula AM-(IV) and BBSI; a compound of Formula AM-(IV) and Compound 101; a compound of Formula AM-(IV) and Compound 106; a compound of Formula AM-(IV) and Compound 108; a compound of Formula AM-(IV) and Compound 109; a compound of Formula AM-(IV) and Compound 110; or a pharmaceutically acceptable salt thereof; and the like.

Certain embodiments provide for a combination of Compound AM-1 and a trypsin inhibitor. Compound AM-1 is 2-Acetylamino-5-guanidino-pentanoic acid ((R)-1-methyl-2-phenylethyl)-amide, or amphetamine-arginine-acetate. In certain embodiments, combinations of Compound AM-1 and a trypsin inhibitor include, but are not limited to the following: Compound AM-1 and SBTI; Compound AM-1 and BBSI; Compound AM-1 and Compound 101; Compound AM-1 and Compound 106; Compound AM-1 and Compound 108; Compound AM-1 and Compound 109; Compound AM-1 and Compound 110; or a pharmaceutically acceptable salt thereof; and the like.

Certain embodiments provide for a combination of Compound AM-2 and a trypsin inhibitor. Compound AM-2 is N-[4-Guanidino-1-((R)-1-methyl-2-phenyl-ethylcarbamoyl)-butyl]-malonic acid, or amphetamine-arginine-malonic acid. In certain embodiments, combinations of Compound AM-2 and a trypsin inhibitor include, but are not limited to the following: Compound AM-2 and SBTI; Compound AM-2 and BBSI; Compound AM-2 and Compound 101; Compound AM-2 and Compound 106; Compound AM-2 and Compound 108; Compound AM-2 and Compound 109; Compound AM-2 and Compound 110; or a pharmaceutically acceptable salt thereof; and the like.

Certain embodiments provide for a combination of Compound AM-5 and a trypsin inhibitor. Compound AM-5 is amphetamine-lysine-acetate. In certain embodiments, combinations of Compound AM-5 and a trypsin inhibitor include, but are not limited to the following: Compound AM-5 and SBTI; Compound AM-5 and BBSI; Compound AM-5 and Compound 101; Compound AM-5 and Compound 106; Compound AM-2 and Compound 108; Compound AM-5 and Compound 109; Compound AM-5 and Compound 110; or a pharmaceutically acceptable salt thereof; and the like.

The embodiments provide a pharmaceutical composition, which comprises Compound 109 and a compound of formula AM-(I) or a pharmaceutically acceptable salt thereof. The embodiments provide a pharmaceutical composition, which comprises Compound 109 and a compound of formula AM-(II) or a pharmaceutically acceptable salt thereof. The embodiments provide a pharmaceutical composition, which comprises Compound 109 and Compound AM-1 or a pharmaceutically acceptable salt thereof. The embodiments provide a pharmaceutical composition, which comprises Compound 109 and Compound AM-2 or a pharmaceutically acceptable salt thereof. The embodiments provide a pharmaceutical composition, which comprises Compound 109 and Compound AM-5 or a pharmaceutically acceptable salt thereo Combinations of Amphetamine Prodrugs and Other Drugs The disclosure provides for an amphetamine prodrug and a further prodrug or drug included in a pharmaceutical composition. Such a prodrug or drug may provide additional stimulant effects or may have effects other than, or in addition to, the effects associated with amphetamines. Embodiments provide a pharmaceutical composition, which comprises an amphetamine prodrug and a further prodrug or drug and optionally comprises an enzyme inhibitor. Also included are pharmaceutically acceptable salts thereof.

In certain embodiments, the enzyme inhibitor is selected from SBTI, BBSI, Compound 101, Compound 106, Compound 108, Compound 109, and Compound 110. In certain embodiments, the enzyme inhibitor is camostat.

In certain embodiments, a pharmaceutical composition can comprise an amphetamine prodrug, a non-amphetamine drug and at least one enzyme inhibitor.

Pharmaceutical Compositions and Methods of Use

The pharmaceutical composition according to the embodiments can further comprise a pharmaceutically acceptable carrier. The composition is conveniently formulated in a form suitable for oral (including buccal and sublingual) administration, for example as a tablet, capsule, thin film, powder, suspension, solution, syrup, dispersion or emulsion. The composition can contain components conventional in pharmaceutical preparations, e.g., one or more carriers, binders, lubricants, excipients (e.g., to impart controlled release characteristics), pH modifiers, sweeteners, bulking agents, coloring agents or further active agents.

Patients can be humans, and also other mammals, such as livestock, zoo animals and companion animals, such as a cat, dog or horse.

In some aspects, the embodiments provide a pharmaceutical composition as described herein for use in the treatment of conditions such as, but not limited to, Attention Deficit Hyperactivity Disorder (ADHD), Chronic Fatigue Syndrome (CFS), brain injuries, narcolepsy, obesity, etc. The pharmaceutical composition according to the embodiments is useful, for example, in the treatment of a patient suffering from, ADHD, CFS, brain injury, narcolepsy, obesity, etc. Accordingly, the present disclosure provides methods of treating or preventing ADHD, CFS, brain injury, narcolepsy, or obesity in a subject, the methods involving administering to the subject a disclosed composition. The present disclosure provides for a disclosed composition for use in therapy or prevention or as a medicament. The present disclosure also provides the use of a disclosed composition for the manufacture of a medicament, especially for the manufacture of a medicament for the treatment or prevention of ADHD, CFS, brain injury, narcolepsy, or obesity.

The present disclosure provides use of an amphetamine prodrug and an enzyme inhibitor, such as a trypsin inhibitor, in the treatment of ADHD, CFS, brain injury, narcolepsy, or obesity. The present disclosure provides use of an amphetamine prodrug and an enzyme inhibitor, such as a trypsin inhibitor, in the prevention of ADHD, CFS, brain injury, narcolepsy, or obesity.

The present disclosure provides use of an amphetamine prodrug and an enzyme inhibitor, such as a trypsin inhibitor, in the manufacture of a medicament for treatment of ADHD, CFS, brain injury, narcolepsy, or obesity. The present disclosure provides use of an amphetamine prodrug and an enzyme inhibitor, such as a trypsin inhibitor, in the manufacture of a medicament for prevention of ADHD, CFS, brain injury, narcolepsy, or obesity.

In another aspect, the embodiments provide a method of treating ADHD, CFS, brain injury, narcolepsy, or obesity in a patient requiring treatment, which comprises administering an effective amount of a pharmaceutical composition as described herein. In another aspect, the embodiments provides a method of preventing ADHD, CFS, brain injury, narcolepsy, or obesity in a patient requiring treatment, which comprises administering an effective amount of a pharmaceutical composition as described herein.

The amount of composition disclosed herein to be administered to a patient to be effective (i.e., to provide blood levels of amphetamine sufficient to be effective in the treatment or prophylaxis of ADHD, CFS, brain injury, narcolepsy, or obesity) will depend upon the bioavailability of the particular composition, the susceptibility of the particular composition to enzyme activation in the gut, the amount and potency of enzyme inhibitor (e.g., trypsin inhibitor) present in the composition, as well as other factors, such as the species, age, weight, sex, and condition of the patient, manner of administration and judgment of the prescribing physician. In general, the composition dose can be such that the amphetamine prodrug is in the range of from 0.01 milligrams prodrug per kilogram to 20 milligrams prodrug per kilogram (mg/kg) body weight. For example, a composition comprising a residue of amphetamine can be administered at a dose equivalent to administering free amphetamine in the range of from 0.01 mg/kg to 40 mg/kg body weight, or 0.1 to 30 mg/kg body weight, or 0.2 to 20 mg/kg body weight. In one embodiment wherein the composition comprises an amphetamine prodrug, the composition can be administered at a dose such that the level of amphetamine achieved in the blood is in the range of from 0.5 ng/ml to 200 ng/ml.

The amount of an enzyme inhibitor (e.g., a trypsin inhibitor) to be administered to the patient to be effective (i.e., to attenuate release of amphetamine when administration of an amphetamine prodrug disclosed herein alone would lead to overexposure of amphetamine) will depend upon the effective dose of the particular prodrug and the potency of the particular enzyme inhibitor, as well as other factors, such as the species, age, weight, sex and condition of the patient, manner of administration and judgment of the prescribing physician. In general, the dose of enzyme inhibitor can be in the range of from 0.001 mg to 50 mg per mg of prodrug disclosed herein. In a certain embodiment, the dose of enzyme inhibitor can be in the range of from 0.05 mg to 50 mg per mg of prodrug disclosed herein. In one embodiment, the dose of enzyme inhibitor can be in the range of from 0.01 nanomoles to 100 micromoles per micromole of prodrug disclosed herein.

Representative Embodiments of Dose Units of Prodrug and GI Enzyme Inhibitor Having a Desired Pharmacokinetic Profile The embodiments include a composition that comprises (a) an amphetamine prodrug of Formulae AM-(I) or AM-(II), which comprises amphetamine covalently bound to a promoiety comprising a GI enzyme-cleavable moiety, wherein cleavage of the GI enzyme-cleavable moiety by a GI enzyme mediates release of the amphetamine, and (b) a GI enzyme inhibitor that interacts with the GI enzyme that mediates enzymatically-controlled release of the amphetamine from the prodrug following ingestion of the composition. In one embodiment, the GI enzyme is trypsin, the GI enzyme-cleavable moiety is a trypsin-cleavable moiety, and the GI enzyme inhibitor is a trypsin inhibitor.

The embodiments include a dose unit comprising a composition, such as a pharmaceutical composition, comprising an amphetamine prodrug of Formulae AM-(I) or AM-(II) and a GI enzyme inhibitor, where the amphetamine prodrug of Formulae AM-(I) or AM-(II) and GI enzyme inhibitor are present in the dose unit in an amount effective to provide for a pre-selected pharmacokinetic (PK) profile following ingestion. In further embodiments, the pre-selected PK profile comprises at least one PK parameter value that is less than the PK parameter value of amphetamine released following ingestion of an equivalent dosage of an amphetamine prodrug of Formulae AM-(I) or AM-(II) in the absence of inhibitor. In further embodiments, the PK parameter value is selected from an amphetamine Cmax value, an amphetamine exposure value, and a (1/amphetamine Tmax) value.

In certain embodiments, the dose unit provides for a pre-selected PK profile following ingestion of at least two dose units. In related embodiments, the pre-selected PK profile of such dose units is modified relative to the PK profile following ingestion of an equivalent dosage of an amphetamine prodrug of Formulae AM-(I) or AM-(II) without inhibitor. In related embodiments, such a dose unit provides that ingestion of an increasing number of the dose units provides for a linear PK profile. In related embodiments, such a dose unit provides that ingestion of an increasing number of the dose units provides for a nonlinear PK profile. In related embodiments, the PK parameter value of the PK profile of such a dose unit is selected from an amphetamine Cmax value, a (1/amphetamine Tmax) value, and an amphetamine exposure value.

The embodiments include methods for treating a patient comprising administering any of the compositions, such as pharmaceutical compositions, comprising an amphetamine prodrug of Formulae AM-(I) or AM-(II) and a GI enzyme inhibitor or dose units described herein to a patient in need thereof. The embodiments include methods to reduce side effects of a therapy comprising administering any of such compositions, e.g., pharmaceutical compositions, or dose units described herein, to a patient in need thereof. The embodiments include methods of improving patient compliance with a therapy prescribed by a clinician comprising directing administration of any of such compositions, e.g., pharmaceutical compositions, or dose units described herein, to a patient in need thereof. Such embodiments can provide for improved patient compliance with a prescribed therapy as compared to patient compliance with a prescribed therapy using drug and/or using prodrug without inhibitor as compared to prodrug with inhibitor.

The embodiments include methods of reducing risk of unintended overdose of amphetamine comprising directing administration of any of such compositions, e.g., pharmaceutical compositions, or dose units described herein, to a patient in need of treatment.

The embodiments include methods of making a dose unit comprising combining an amphetamine prodrug of Formulae AM-(I) or AM-(II) and a GI enzyme inhibitor in a dose unit, wherein the amphetamine prodrug of Formulae AM-(I) or AM-(II) and GI enzyme inhibitor are present in the dose unit in an amount effective to attenuate release of amphetamine from the amphetamine prodrug of Formulae AM-(I) or AM-(II).

The embodiments include methods of deterring misuse or abuse of multiple dose units of an amphetamine prodrug of Formulae AM-(I) or AM-(II) comprising combining an amphetamine prodrug of Formulae AM-(I) or AM-(II) and a GI enzyme inhibitor in a dose unit, wherein the amphetamine prodrug of Formulae AM-(I) or AM-(II) and GI enzyme inhibitor are present in the dose unit in an amount effective to attenuate release of amphetamine from the amphetamine prodrug of Formulae AM-(I) or AM-(II) such that ingestion of multiples of dose units by a patient does not provide a proportional release of the amphetamine. In further embodiments, release of drug is decreased compared to release of drug by an equivalent dosage of prodrug in the absence of inhibitor.

One embodiment is a method for identifying a GI enzyme inhibitor and prodrug of Formulae AM-(I) or AM-(II) suitable for formulation in a dose unit. Such a method can be conducted as, for example, an in vitro assay, an in vivo assay, or an ex vivo assay. In one embodiment, the GI enzyme inhibitor is a trypsin inhibitor.

The embodiments include methods for identifying a GI enzyme inhibitor and prodrug of Formulae AM-(I) or AM-(II) suitable for formulation in a dose unit comprising combining a prodrug of Formulae AM-(I) or AM-(II), a GI enzyme inhibitor, and a GI enzyme in a reaction mixture, and detecting prodrug conversion, wherein a decrease in prodrug conversion in the presence of the GI enzyme inhibitor as compared to prodrug conversion in the absence of the GI enzyme inhibitor indicates the GI enzyme inhibitor and prodrug of Formulae AM-(I) or AM-(II) are suitable for formulation in a dose unit.

The embodiments include methods for identifying a GI enzyme inhibitor and prodrug of Formulae AM-(I) or AM-(II) suitable for formulation in a dose unit comprising administering to an animal a GI enzyme inhibitor and prodrug of Formulae AM-(I) or AM-(II) and detecting prodrug conversion, wherein a decrease in amphetamine conversion in the presence of the GI enzyme inhibitor as compared to amphetamine conversion in the absence of the GI enzyme inhibitor indicates the GI enzyme inhibitor and prodrug of Formulae AM-(I) or AM-(II) are suitable for formulation in a dose unit. In certain embodiments, administering comprises administering to the animal increasing doses of inhibitor co-dosed with a selected fixed dose of prodrug. Detecting prodrug conversion can facilitate identification of a dose of inhibitor and a dose of prodrug that provides for a pre-selected pharmacokinetic (PK) profile. Such methods can be conducted as, for example, an in vivo assay or an ex vivo assay.

The embodiments include methods for identifying a GI enzyme inhibitor and prodrug of Formulae I-XII suitable for formulation in a dose unit comprising administering to an animal tissue a GI enzyme inhibitor and prodrug of Formulae AM-(I) or AM-(II) and detecting prodrug conversion, wherein a decrease in prodrug conversion in the presence of the GI enzyme inhibitor as compared to prodrug conversion in the absence of the GI enzyme inhibitor indicates the GI enzyme inhibitor and prodrug of Formulae AM-(I) or AM-(II) are suitable for formulation in a dose unit.

Dose Units of Prodrug and Inhibitor Having a Desired Pharmacokinetic Profile

The present disclosure provides dose units of prodrug and inhibitor that can provide for a desired pharmacokinetic (PK) profile. Dose units can provide a modified PK profile compared to a reference PK profile as disclosed herein. It will be appreciated that a modified PK profile can provide for a modified pharmacodynamic (PD) profile. Ingestion of multiples of such a dose unit can also provide a desired PK profile.

Unless specifically stated otherwise, "dose unit" as used herein refers to a combination of a GI enzyme-cleavable prodrug (e.g., a trypsin-cleavable prodrug) and a GI enzyme inhibitor (e.g., a trypsin inhibitor). A "single dose unit" is a single unit of a combination of a GI enzyme-cleavable prodrug (e.g., a trypsin-cleavable prodrug) and a GI enzyme inhibitor (e.g., a trypsin inhibitor), where the single dose unit provide a therapeutically effective amount of drug (i.e., a sufficient amount of drug to produce a therapeutic effect, e.g., a dose within the respective drug's therapeutic window, or therapeutic range). "Multiple dose units" or "multiples of a dose unit" or a "multiple of a dose unit" refers to at least two single dose units.

As used herein, a "PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile".) A PK profile is characterized by PK parameters.

As used herein, a "PK parameter" refers to a measure of drug concentration in blood or plasma, such as: (1) "drug Cmax", the maximum concentration of drug achieved in blood or plasma; (2) "drug Tmax", the time elapsed following ingestion to achieve Cmax; and (3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

For purposes of describing the features of dose units of the present disclosure, "PK parameter values" that define a PK profile include drug Cmax (e.g., amphetamine Cmax), total drug exposure (e.g., area under the curve) (e.g., amphetamine exposure) and 1/(drug Tmax) (such that a decreased 1/Tmax is indicative of a delay in Tmax relative to a reference Tmax) (e.g., 1/amphetamine Tmax). Thus, a decrease in a PK parameter value relative to a reference PK parameter value can indicate, for example, a decrease in drug Cmax, a decrease in drug exposure, and/or a delayed Tmax.

Dose units of the present disclosure can be adapted to provide for a modified PK profile, e.g., a PK profile that is different from that achieved from dosing a given dose of prodrug in the absence of inhibitor (i.e., without inhibitor). For example, dose units can provide for at least one of decreased drug Cmax, delayed drug Tmax and/or decreased drug exposure compared to ingestion of a dose of prodrug in the same amount but in the absence of inhibitor. Such a modification is due to the inclusion of an inhibitor in the dose unit.

As used herein, "a pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax), and side effects.

FIG. 1 is a schematic illustrating an example of the effect of increasing inhibitor concentrations upon the PK parameter drug Cmax for a fixed dose of prodrug. At low concentrations of inhibitor, there may be no detectable effect on drug release, as illustrated by the plateau portion of the plot of drug Cmax (Y-axis) versus inhibitor concentration (X-axis). As inhibitor concentration increases, a concentration is reached at which drug release from prodrug is attenuated, causing a decrease in, or suppression of, drug Cmax. Thus, the effect of inhibitor upon a prodrug PK parameter for a dose unit of the present disclosure can range from undetectable, to moderate, to complete inhibition (i.e., no detectable drug release).

A dose unit can be adapted to provide for a desired PK profile (e.g., a concentration-time PK profile) following ingestion of a single dose. A dose unit can be adapted to provide for a desired PK profile (e.g., a concentration-dose PK profile) following ingestion of multiple dose units (e.g., at least 2, at least 3, at least 4 or more dose units).

Dose Units Providing Modified PK Profiles

A combination of a prodrug and an inhibitor in a dose unit can provide a desired (or "pre-selected") PK profile (e.g., a concentration-time PK profile) following ingestion of a single dose. The PK profile of such a dose unit can be characterized by one or more of a pre-selected drug Cmax, a pre-selected drug Tmax or a pre-selected drug exposure. The PK profile of the dose unit can be modified compared to a PK profile achieved from the equivalent dosage of prodrug in the absence of inhibitor (i.e., a dose that is the same as the dose unit except that it lacks inhibitor).

A modified PK profile can have a decreased PK parameter value relative to a reference PK parameter value (e.g., a PK parameter value of a PK profile following ingestion of a dosage of prodrug that is equivalent to a dose unit except without inhibitor). For example, a dose unit can provide for a decreased drug Cmax, decreased drug exposure, and/or delayed drug Tmax.

Figure 2:
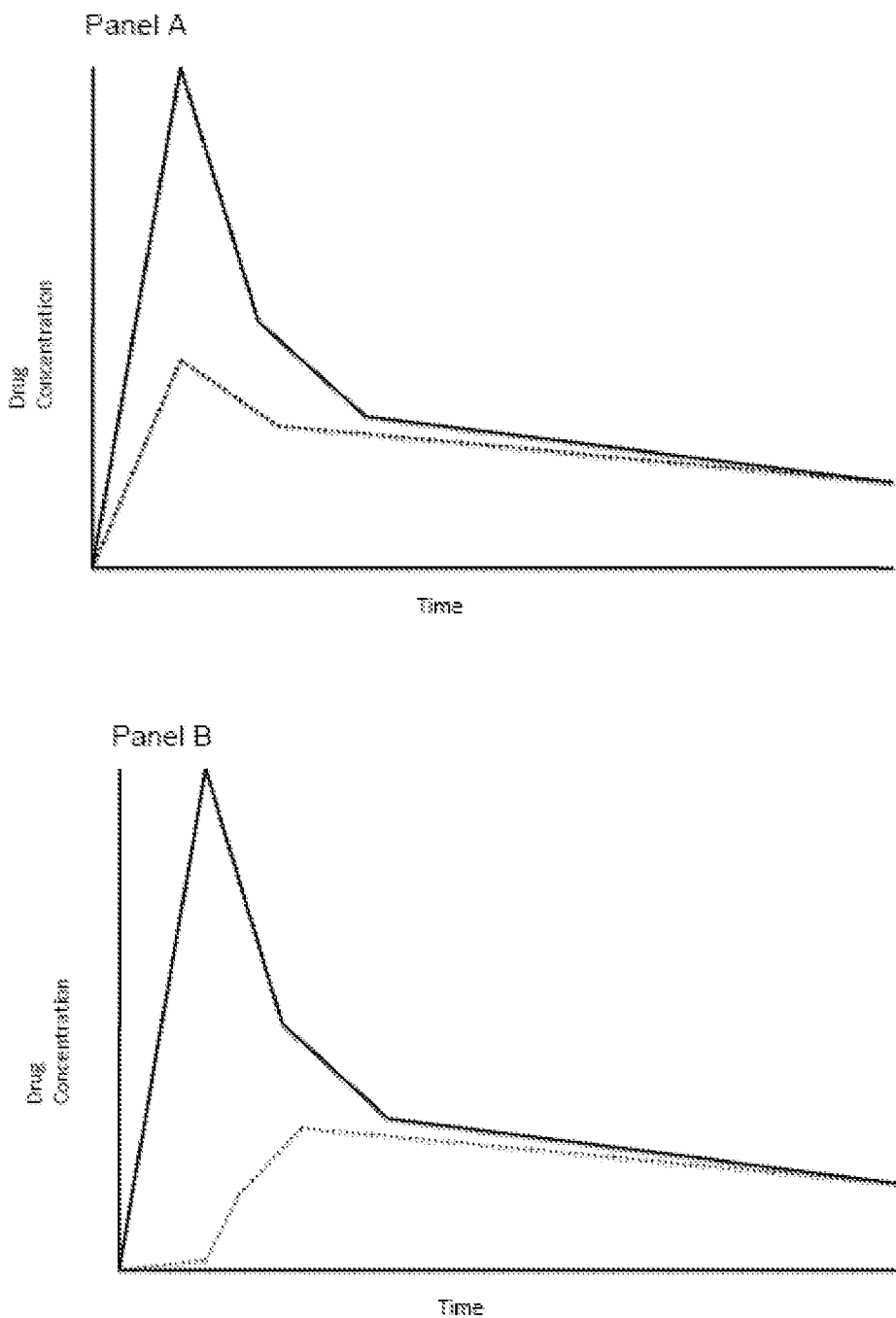
FIG. 2 provides schematics of drug concentration in plasma (Y-axis) over time (X-axis). Panel A is a schematic of a pharmacokinetic (PK) profile following ingestion of prodrug with a GI enzyme inhibitor (dashed line) where the drug Cmax is modified relative to that of prodrug without inhibitor (solid line). Panel B is a schematic of a PK profile following ingestion of prodrug with inhibitor (dashed line) where drug Cmax and drug Tmax are modified relative to that of prodrug without inhibitor (solid line). Panel C is a schematic of a PK profile following ingestion of prodrug with inhibitor (dashed line) where drug Tmax is modified relative to that of prodrug without inhibitor (solid line).
Figure 2:
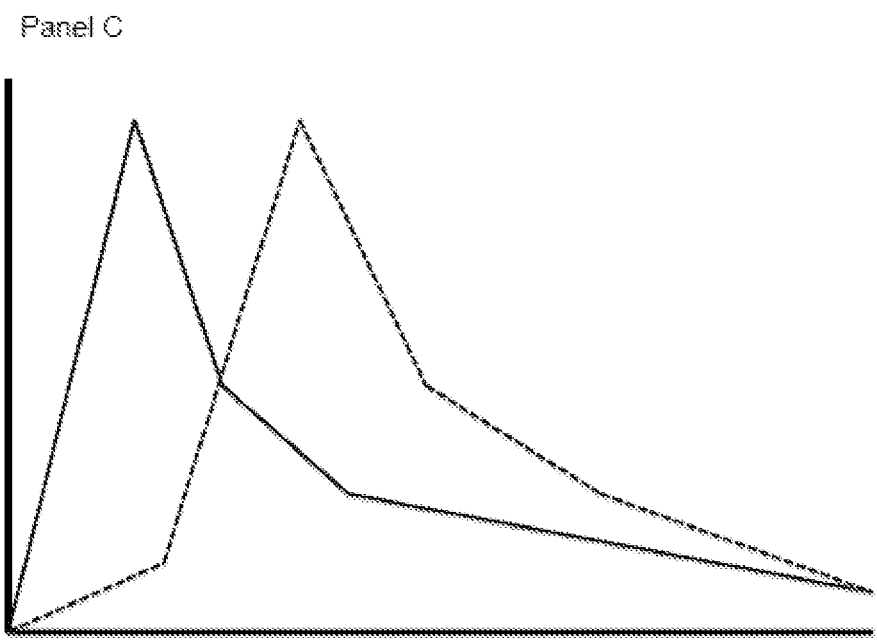

FIG. 2 presents schematic graphs showing examples of modified concentration-time PK profiles of a single dose unit. Panel A is a schematic of drug concentration in blood or plasma (Y-axis) following a period of time (X-axis) after ingestion of prodrug in the absence or presence of inhibitor. The solid, top line in Panel A provides an example of drug concentration following ingestion of prodrug without inhibitor. The dashed, lower line in Panel A represents drug concentration following ingestion of the same dose of prodrug with inhibitor. Ingestion of inhibitor with prodrug provides for a decreased drug Cmax relative to the drug Cmax that results from ingestion of the same amount of prodrug in the absence of inhibitor. Panel A also illustrates that the total drug exposure following ingestion of prodrug with inhibitor is also decreased relative to ingestion of the same amount of prodrug without inhibitor.

Panel B of FIG. 2 provides another example of a dose unit having a modified concentration-time PK profile. As in Panel A, the solid top line represents drug concentration over time in blood or plasma following ingestion of prodrug without inhibitor, while the dashed lower line represents drug concentration following ingestion of the same amount of prodrug with inhibitor. In this example, the dose unit provides a PK profile having a decreased drug Cmax, decreased drug exposure, and a delayed drug Tmax (i.e., decreased (1/drug Tmax) relative to ingestion of the same dose of prodrug without inhibitor.

Panel C of FIG. 2 provides another example of a dose unit having a modified concentration-time PK profile. As in Panel A, the solid line represents drug concentration over time in blood or plasma following ingestion of prodrug without inhibitor, while the dashed line represents drug concentration following ingestion of the same amount of prodrug with inhibitor. In this example, the dose unit provides a PK profile having a delayed drug Tmax (i.e., decreased (1/drug Tmax) relative to ingestion of the same dose of prodrug without inhibitor.

Dose units that provide for a modified PK profile (e.g., a decreased drug Cmax and/or delayed drug Tmax as compared to, a PK profile of drug or a PK profile of prodrug without inhibitor), find use in tailoring of drug dose according to a patient's needs (e.g., through selection of a particular dose unit and/or selection of a dosage regimen), reduction of side effects, and/or improvement in patient compliance (as compared to side effects or patient compliance associated with drug or with prodrug without inhibitor). As used herein, "patient compliance" refers to whether a patient follows the direction of a clinician (e.g., a physician) including ingestion of a dose that is neither significantly above nor significantly below that prescribed. Such dose units also reduce the risk of misuse, abuse or overdose by a patient as compared to such risk(s) associated with drug or prodrug without inhibitor. For example, dose units with a decreased drug Cmax provide less reward for ingestion than does a dose of the same amount of drug, and/or the same amount of prodrug without inhibitor.

Dose Units Providing Modified PK Profiles Upon Ingestion of Multiple Dose Units

A dose unit of the present disclosure can be adapted to provide for a desired PK profile (e.g., a concentration-time PK profile or concentration-dose PK profile) following ingestion of multiples of a dose unit (e.g., at least 2, at least 3, at least 4, or more dose units). A concentration-dose PK profile refers to the relationship between a selected PK parameter and a number of single dose units ingested. Such a profile can be dose proportional, linear (a linear PK profile) or nonlinear (a nonlinear PK profile). A modified concentration-dose PK profile can be provided by adjusting the relative amounts of prodrug and inhibitor contained in a single dose unit and/or by using a different prodrug and/or inhibitor.

Figure 3:
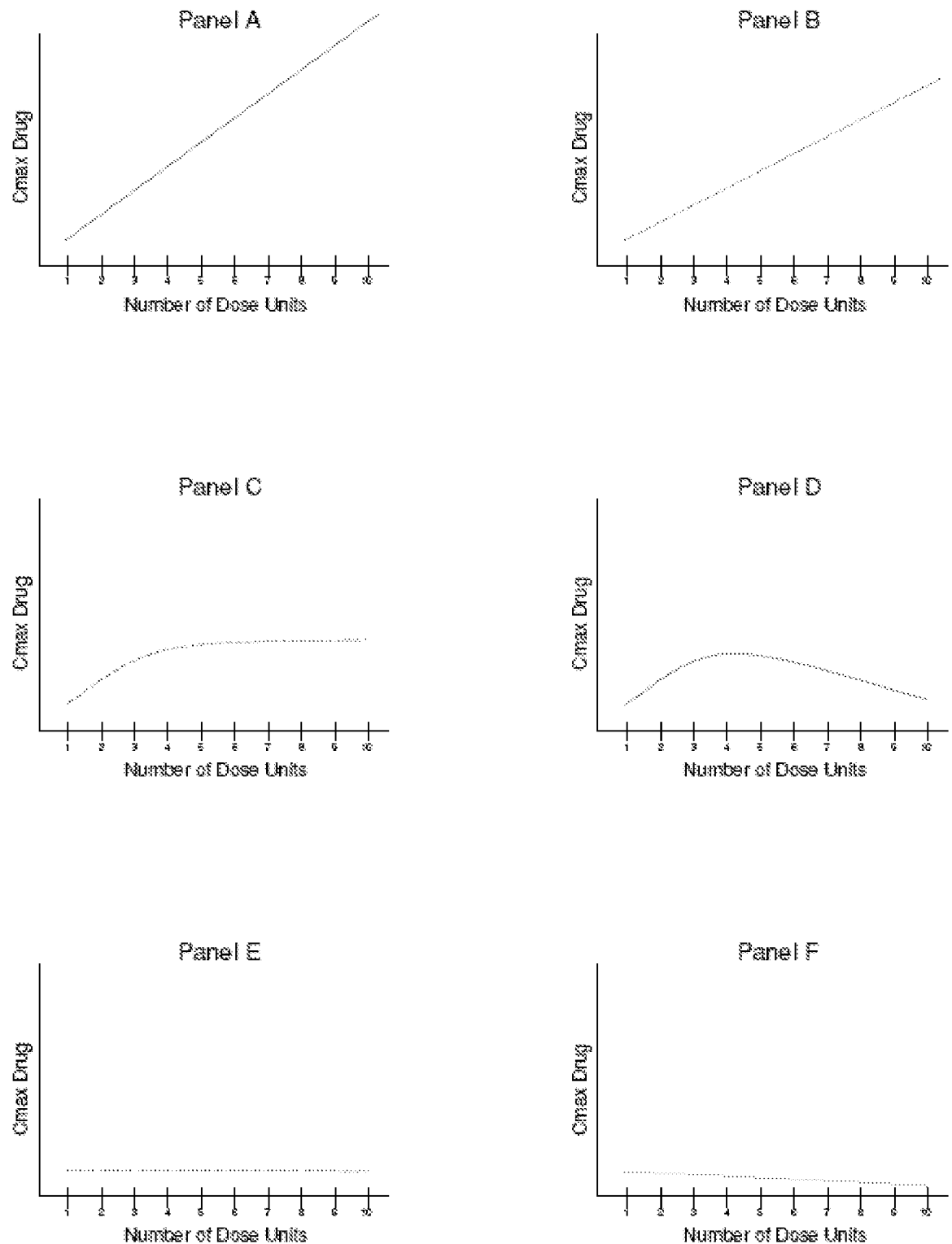
FIG. 3 provides schematics representing differential concentration-dose PK profiles that can result from the dosing of multiples of a dose unit (X-axis) of the present disclosure. Different PK profiles (as exemplified herein for a representative PK parameter, drug Cmax (Y-axis)) can be provided by adjusting the relative amount of prodrug and GI enzyme inhibitor contained in a single dose unit or by using a different prodrug or inhibitor in the dose unit.

FIG. 3 provides schematics of examples of concentration-dose PK profiles (exemplified by drug Cmax, Y-axis) that can be provided by ingestion of multiples of a dose unit (X-axis) of the present disclosure. Each profile can be compared to a concentration-dose PK profile provided by increasing doses of drug alone, where the amount of drug in the blood or plasma from one dose represents a therapeutically effective amount equivalent to the amount of drug released into the blood or plasma by one dose unit of the disclosure. Such a "drug alone" PK profile is typically dose proportional, having a forty-five degree angle positive linear slope. It is also to be appreciated that a concentration-dose PK profile resulting from ingestion of multiples of a dose unit of the disclosure can also be compared to other references, such as a concentration-dose PK profile provided by ingestion of an increasing number of doses of prodrug without inhibitor wherein the amount of drug released into the blood or plasma by a single dose of prodrug in the absence of inhibitor represents a therapeutically effective amount equivalent to the amount of drug released into the blood or plasma by one dose unit of the disclosure.

As illustrated by the relationship between prodrug and inhibitor concentration in FIG. 1, a dose unit can include inhibitor in an amount that does not detectably affect drug release following ingestion. Ingestion of multiples of such a dose unit can provide a concentration-dose PK profile such that the relationship between number of dose units ingested and PK parameter value is linear with a positive slope, which is similar to, for example, a dose proportional PK profile of increasing amounts of prodrug alone. Panel A of FIG. 3 depicts such a profile. Dose units that provide a concentration-dose PK profile having such an undetectable change in drug Cmax in vivo compared to the profile of prodrug alone can find use in thwarting enzyme conversion of prodrug from a dose unit that has sufficient inhibitor to reduce or prevent in vitro cleavage of the enzyme-cleavable prodrug by its respective enzyme.

Panel B in FIG. 3 represents a concentration-dose PK profile such that the relationship between the number of dose units ingested and a PK parameter value is linear with positive slope, where the profile exhibits a reduced slope relative to panel A. Such a dose unit provides a profile having a decreased PK parameter value (e.g., drug Cmax) relative to a reference PK parameter value exhibiting dose proportionality.

Concentration-dose PK profiles following ingestion of multiples of a dose unit can be non-linear, Panel C in FIG. 3 represents an example of a non-linear, biphasic concentration-dose PK profile. In this example, the biphasic concentration-dose PK profile contains a first phase over which the concentration-dose PK profile has a positive rise, and then a second phase over which the relationship between number of dose units ingested and a PK parameter value (e.g., drug Cmax) is relatively flat (substantially linear with zero slope). For such a dose unit, for example, drug Cmax can be increased for a selected number of dose units (e.g., 2, 3, or 4 dose units). However, ingestion of additional dose units does not provide for a significant increase in drug Cmax.

Panel D in FIG. 3 represents another example of a non-linear, biphasic concentration-dose PK profile. In this example, the biphasic concentration-dose PK profile is characterized by a first phase over which the concentration-dose PK profile has a positive rise and a second phase over which the relationship between number of dose units ingested and a PK parameter value (e.g., drug Cmax) declines. Dose units that provide this concentration-dose PK profile provide for an increase in drug Cmax for a selected number of ingested dose units (e.g., 2, 3, or 4 dose units). However, ingestion of further additional dose units does not provide for a significant increase in drug Cmax and instead provides for decreased drug Cmax.

Panel E in FIG. 3 represents a concentration-dose PK profile in which the relationship between the number of dose units ingested and a PK parameter (e.g., drug Cmax) is linear with zero slope. Such dose units do not provide for a significant increase or decrease in drug Cmax with ingestion of multiples of dose units.

Panel F in FIG. 3 represents a concentration-dose PK profile in which the relationship between number of dose units ingested and a PK parameter value (e.g., drug Cmax) is linear with a negative slope. Thus, drug Cmax decreases as the number of dose units ingested increases.

Dose units that provide for concentration-dose PK profiles when multiples of a dose unit are ingested find use in tailoring of a dosage regimen to provide a therapeutic level of released drug while reducing the risk of overdose, misuse, or abuse. Such reduction in risk can be compared to a reference, e.g., to administration of drug alone or prodrug alone. In one embodiment, risk is reduced compared to administration of a drug or prodrug that provides a proportional concentration-dose PK profile. A dose unit that provides for a concentration-dose PK profile can reduce the risk of patient overdose through inadvertent ingestion of dose units above a prescribed dosage. Such a dose unit can reduce the risk of patient misuse (e.g., through self-medication). Such a dose unit can discourage abuse through deliberate ingestion of multiple dose units. For example, a dose unit that provides for a biphasic concentration-dose PK profile can allow for an increase in drug release for a limited number of dose units ingested, after which an increase in drug release with ingestion of more dose units is not realized. In another example, a dose unit that provides for a concentration-dose PK profile of zero slope can allow for retention of a similar drug release profile regardless of the number of dose units ingested.

Ingestion of multiples of a dose unit can provide for adjustment of a PK parameter value relative to that of ingestion of multiples of the same dose (either as drug alone or as a prodrug) in the absence of inhibitor such that, for example, ingestion of a selected number (e.g., 2, 3, 4 or more) of a single dose unit provides for a decrease in a PK parameter value compared to ingestion of the same number of doses in the absence of inhibitor.

Pharmaceutical compositions include those having an inhibitor to provide for protection of a therapeutic compound from degradation in the GI tract. Inhibitor can be combined with a drug (i.e., not a prodrug) to provide for protection of the drug from degradation in the GI system. In this example, the composition of inhibitor and drug provide for a modified PK profile by increasing a PK parameter. Inhibitor can also be combined with a prodrug that is susceptible to degradation by a GI enzyme and has a site of action outside the GI tract. In this composition, the inhibitor protects ingested prodrug in the GI tract prior to its distribution outside the GI tract and cleavage at a desired site of action.

Methods Used to Define Relative Amounts of Prodrug and Inhibitor in a Dose Unit

Dose units that provide for a desired PK profile, such as a desired concentration-time PK profile and/or a desired concentration-dose PK profile, can be made by combining a prodrug and an inhibitor in a dose unit in relative amounts effective to provide for release of drug that provides for a desired drug PK profile following ingestion by a patient.

Prodrugs can be selected as suitable for use in a dose unit by determining the GI enzyme-mediated drug release competency of the prodrug. This can be accomplished in vitro, in vivo or ex vivo.

In vitro assays can be conducted by combining a prodrug with a GI enzyme (e.g., trypsin) in a reaction mixture. The GI enzyme can be provided in the reaction mixture in an amount sufficient to catalyze cleavage of the prodrug. Assays are conducted under suitable conditions, and optionally may be under conditions that mimic those found in a GI tract of a subject, e.g., human. "Prodrug conversion" refers to release of drug from prodrug. Prodrug conversion can be assessed by detecting a level of a product of prodrug conversion (e.g., released drug) and/or by detecting a level of prodrug that is maintained in the presence of the GI enzyme. Prodrug conversion can also be assessed by detecting the rate at which a product of prodrug conversion occurs or the rate at which prodrug disappears. An increase in released drug, or a decrease in prodrug, indicate prodrug conversion has occurred. Prodrugs that exhibit an acceptable level of prodrug conversion in the presence of the GI enzyme within an acceptable period of time are suitable for use in a dose unit in combination with an inhibitor of the GI enzyme that is shown to mediate prodrug conversion.

In vivo assays can assess the suitability of a prodrug for use in a dose unit by administration of the prodrug to an animal (e.g., a human or non-human animal, e.g., rat, dog, pig, etc.). Such administration can be enteral (e.g., oral administration). Prodrug conversion can be detected by, for example, detecting a product of prodrug conversion (e.g., released drug or a metabolite of released drug) or detecting prodrug in blood or plasma of the animal at a desired time point(s) following administration.

Ex vivo assays, such as a gut loop or inverted gut loop assay, can assess the suitability of a prodrug for use in a dose unit by, for example, administration of the prodrug to a ligated section of the intestine of an animal. Prodrug conversion can be detected by, for example, detecting a product of prodrug conversion (e.g., released drug or a metabolite of released drug) or detecting prodrug in the ligated gut loop of the animal at a desired time point(s) following administration.

Inhibitors are generally selected based on, for example, activity in interacting with the GI enzyme(s) that mediate release of drug from a prodrug with which the inhibitor is to be co-dosed. Such assays can be conducted in the presence of enzyme either with or without prodrug. Inhibitors can also be selected according to properties such as half-life in the GI system, potency, avidity, affinity, molecular size and/or enzyme inhibition profile (e.g., steepness of inhibition curve in an enzyme activity assay, inhibition initiation rate). Inhibitors for use in prodrug-inhibitor combinations can be selected through use of in vitro, in vivo and/or ex vivo assays.

One embodiment is a method for identifying a prodrug and a GI enzyme inhibitor suitable for formulation in a dose unit wherein the method comprises combining a prodrug (e.g., an amphetamine prodrug), a GI enzyme inhibitor (e.g., a trypsin inhibitor), and a GI enzyme (e.g., trypsin) in a reaction mixture and detecting prodrug conversion. Such a combination is tested for an interaction between the prodrug, inhibitor and enzyme, i.e., tested to determine how the inhibitor will interact with the enzyme that mediates enzymatically-controlled release of the drug from the prodrug. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit. Such a method can be an in vitro assay.

One embodiment is a method for identifying a prodrug and a GI enzyme inhibitor suitable for formulation in a dose unit wherein the method comprises administering to an animal a prodrug (e.g., an amphetamine prodrug) and a GI enzyme inhibitor (e.g., a trypsin inhibitor) and detecting prodrug conversion. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit. Such a method can be an in vivo assay; for example, the prodrug and GI enzyme inhibitor can be administered orally. Such a method can also be an ex vivo assay; for example, the prodrug and GI enzyme inhibitor can be administered orally or to a tissue, such as an intestine, that is at least temporarily exposed. Detection can occur in the blood or plasma or respective tissue. As used herein, tissue refers to the tissue itself and can also refer to contents within the tissue.

One embodiment is a method for identifying a prodrug and a GI enzyme inhibitor suitable for formulation in a dose unit wherein the method comprises administering a prodrug and a gastrointestinal (GI) enzyme inhibitor to an animal tissue that has removed from an animal and detecting prodrug conversion. In one embodiment, a decrease in prodrug conversion in the presence of the GI enzyme inhibitor as compared to prodrug conversion in the absence of the GI enzyme inhibitor indicates the prodrug and GI enzyme inhibitor are suitable for formulation in a dose unit.

In vitro assays can be conducted by combining a prodrug, an inhibitor and a GI enzyme in a reaction mixture. The GI enzyme can be provided in the reaction mixture in an amount sufficient to catalyze cleavage of the prodrug, and assays conducted under suitable conditions, optionally under conditions that mimic those found in a GI tract of a subject, e.g., human. Prodrug conversion can be assessed by detecting a level of a product of prodrug conversion (e.g., released drug) and/or by detecting a level of prodrug maintained in the presence of the GI enzyme. Prodrug conversion can also be assessed by detecting the rate at which a product of prodrug conversion occurs or the rate at which prodrug disappears. Prodrug conversion that is modified in the presence of inhibitor as compared to a level of prodrug conversion in the absence of inhibitor indicates the inhibitor is suitable for attenuation of prodrug conversion and for use in a dose unit. Reaction mixtures having a fixed amount of prodrug and increasing amounts of inhibitor, or a fixed amount of inhibitor and increasing amounts of prodrug, can be used to identify relative amounts of prodrug and inhibitor which provide for a desired modification of prodrug conversion.

In vivo assays can assess combinations of prodrugs and inhibitors by co-dosing of prodrug and inhibitor to an animal. Such co-dosing can be enteral. "Co-dosing" refers to administration of prodrug and inhibitor as separate doses or a combined dose (i.e., in the same formulation). Prodrug conversion can be detected by, for example, detecting a product of prodrug conversion (e.g., released drug or drug metabolite) or detecting prodrug in blood or plasma of the animal at a desired time point(s) following administration. Combinations of prodrug and inhibitor can be identified that provide for a prodrug conversion level that yields a desired PK profile as compared to, for example, prodrug without inhibitor.

Combinations of relative amounts of prodrug and inhibitor that provide for a desired PK profile can be identified by dosing animals with a fixed amount of prodrug and increasing amounts of inhibitor, or with a fixed amount of inhibitor and increasing amounts of prodrug. One or more PK parameters can then be assessed, e.g., drug Cmax, drug Tmax, and drug exposure. Relative amounts of prodrug and inhibitor that provide for a desired PK profile are identified as amounts of prodrug and inhibitor for use in a dose unit. The PK profile of the prodrug and inhibitor combination can be, for example, characterized by a decreased PK parameter value relative to prodrug without inhibitor. A decrease in the PK parameter value of an inhibitor-to-prodrug combination (e.g., a decrease in drug Cmax, a decrease in 1/drug Tmax (i.e., a delay in drug Tmax) or a decrease in drug exposure) relative to a corresponding PK parameter value following administration of prodrug without inhibitor can be indicative of an inhibitor-to-prodrug combination that can provide a desired PK profile. Assays can be conducted with different relative amounts of inhibitor and prodrug.

In vivo assays can be used to identify combinations of prodrug and inhibitor that provide for dose units that provide for a desired concentration-dose PK profile following ingestion of multiples of the dose unit (e.g., at least 2, at least 3, at least 4 or more). Ex vivo assays can be conducted by direct administration of prodrug and inhibitor into a tissue and/or its contents of an animal, such as the intestine, including by introduction by injection into the lumen of a ligated intestine (e.g., a gut loop, or intestinal loop, assay, or an inverted gut assay). An ex vivo assay can also be conducted by excising a tissue and/or its contents from an animal and introducing prodrug and inhibitor into such tissues and/or contents.

For example, a dose of prodrug that is desired for a single dose unit is selected (e.g., an amount that provides an efficacious plasma drug level). A multiple of single dose units for which a relationship between that multiple and a PK parameter to be tested is then selected. For example, if a concentration-dose PK profile is to be designed for ingestion of 2, 3, 4, 5, 6, 7, 8, 9 or 10 dose units, then the amount of prodrug equivalent to ingestion of that same number of dose units is determined (referred to as the "high dose"). The multiple of dose units can be selected based on the number of ingested pills at which drug Cmax is modified relative to ingestion of the single dose unit. If, for example, the profile is to provide for abuse deterrence, then a multiple of 10 can be selected, for example. A variety of different inhibitors (e.g., from a panel of inhibitors) can be tested using different relative amounts of inhibitor and prodrug. Assays can be used to identify suitable combination(s) of inhibitor and prodrug to obtain a single dose unit that is therapeutically effective, wherein such a combination, when ingested as a multiple of dose units, provides a modified PK parameter compared to ingestion of the same multiple of drug or prodrug alone (wherein a single dose of either drug or prodrug alone releases into blood or plasma the same amount of drug as is released by a single dose unit).

Increasing amounts of inhibitor are then co-dosed to animals with the high dose of prodrug. The dose level of inhibitor that provides a desired drug Cmax following ingestion of the high dose of prodrug is identified and the resultant inhibitor-to-prodrug ratio determined.

Prodrug and inhibitor are then co-dosed in amounts equivalent to the inhibitor-to-prodrug ratio that provided the desired result at the high dose of prodrug. The PK parameter value of interest (e.g., drug Cmax) is then assessed. If a desired PK parameter value results following ingestion of the single dose unit equivalent, then single dose units that provide for a desired concentration-dose PK profile are identified. For example, where a zero dose linear profile is desired, the drug Cmax following ingestion of a single dose unit does not increase significantly following ingestion of a multiple number of the single dose units.

Methods for Manufacturing, Formulating, and Packaging Dose Units

Dose units of the present disclosure can be made using manufacturing methods available in the art and can be of a variety of forms suitable for enteral (including oral, buccal and sublingual) administration, for example as a tablet, capsule, thin film, powder, suspension, solution, syrup, dispersion or emulsion. The dose unit can contain components conventional in pharmaceutical preparations, e.g. one or more carriers, binders, lubricants, excipients (e.g., to impart controlled release characteristics), pH modifiers, flavoring agents (e.g., sweeteners), bulking agents, coloring agents or further active agents. Dose units of the present disclosure can include can include an enteric coating or other component(s) to facilitate protection from stomach acid, where desired.

Dose units can be of any suitable size or shape. The dose unit can be of any shape suitable for enteral administration, e.g., ellipsoid, lenticular, circular, rectangular, cylindrical, and the like.

Dose units provided as dry dose units can have a total weight of from about 1 microgram to about 1 gram, and can be from about 5 micrograms to 1.5 grams, from about 50 micrograms to 1 gram, from about 100 micrograms to 1 gram, from 50 micrograms to 750 milligrams, and may be from about 1 microgram to 2 grams.

Dose units can comprise components in any relative amounts. For example, dose units can be from about 0.1% to 99% by weight of active ingredients (i.e., prodrug and inhibitor) per total weight of dose unit (0.1% to 99% total combined weight of prodrug and inhibitor per total weight of single dose unit). In some embodiments, dose units can be from 10% to 50%, from 20% to 40%, or about 30% by weight of active ingredients per total weight dose unit.

Dose units can be provided in a variety of different forms and optionally provided in a manner suitable for storage. For example, dose units can be disposed within a container suitable for containing a pharmaceutical composition. The container can be, for example, a bottle (e.g., with a closure device, such as a cap), a blister pack (e.g., which can provide for enclosure of one or more dose units per blister), a vial, flexible packaging (e.g., sealed Mylar or plastic bags), an ampule (for single dose units in solution), a dropper, thin film, a tube and the like.

Containers can include a cap (e.g., screw cap) that is removably connected to the container over an opening through which the dose units disposed within the container can be accessed.

Containers can include a seal which can serve as a tamper-evident and/or tamper-resistant element, which seal is disrupted upon access to a dose unit disposed within the container. Such seal elements can be, for example, a frangible element that is broken or otherwise modified upon access to a dose unit disposed within the container. Examples of such frangible seal elements include a seal positioned over a container opening such that access to a dose unit within the container requires disruption of the seal (e.g., by peeling and/or piercing the seal). Examples of frangible seal elements include a frangible ring disposed around a container opening and in connection with a cap such that the ring is broken upon opening of the cap to access the dose units in the container.

Dry and liquid dose units can be placed in a container (e.g., bottle or package, e.g., a flexible bag) of a size and configuration adapted to maintain stability of dose units over a period during which the dose units are dispensed into a prescription. For example, containers can be sized and configured to contain 10, 20, 30, 40, 50, 60, 70, 80, 90, 100 or more single dry or liquid dose units. The containers can be sealed or resealable. The containers can packaged in a carton (e.g., for shipment from a manufacturer to a pharmacy or other dispensary). Such cartons can be boxes, tubes, or of other configuration, and may be made of any material (e.g., cardboard, plastic, and the like). The packaging system and/or containers disposed therein can have one or more affixed labels (e.g., to provide information such as lot number, dose unit type, manufacturer, and the like).

The container can include a moisture barrier and/or light barrier, e.g., to facilitate maintenance of stability of the active ingredients in the dose units contained therein. Where the dose unit is a dry dose unit, the container can include a desiccant pack which is disposed within the container. The container can be adapted to contain a single dose unit or multiples of a dose unit. The container can include a dispensing control mechanism, such as a lock out mechanism that facilitates maintenance of dosing regimen.

The dose units can be provided in solid or semi-solid form, and can be a dry dose unit. "Dry dose unit" refers to a dose unit that is in other than in a completely liquid form. Examples of dry dose units include, for example, tablets, capsules (e.g., solid capsules, capsules containing liquid), thin film, microparticles, granules, powder and the like. Dose units can be provided as liquid dose units, where the dose units can be provided as single or multiple doses of a formulation containing prodrug and inhibitor in liquid form. Single doses of a dry or liquid dose unit can be disposed within a sealed container, and sealed containers optionally provided in a packaging system, e.g., to provide for a prescribed number of doses, to provide for shipment of dose units, and the like.

Dose units can be formulated such that the prodrug and inhibitor are present in the same carrier, e.g., solubilized or suspended within the same matrix. Alternatively, dose units can be composed of two or more portions, where the prodrug and inhibitor can be provided in the same or different portions, and can be provided in adjacent or non-adjacent portions.

Dose units can be provided in a container in which they are disposed, and may be provided as part of a packaging system (optionally with instructions for use). For example, dose units containing different amounts of prodrug can be provided in separate containers, which containers can be disposed with in a larger container (e.g., to facilitate protection of dose units for shipment). For example, one or more dose units as described herein can be provided in separate containers, where dose units of different composition are provided in separate containers, and the separate containers disposed within package for dispensing.

In another example, dose units can be provided in a double-chambered dispenser where a first chamber contains a prodrug formulation and a second chamber contains an inhibitor formulation. The dispenser can be adapted to provide for mixing of a prodrug formulation and an inhibitor formulation prior to ingestion. For example, the two chambers of the dispenser can be separated by a removable wall (e.g., frangible wall) that is broken or removed prior to administration to allow mixing of the formulations of the two chambers. The first and second chambers can terminate into a dispensing outlet, optionally through a common chamber. The formulations can be provided in dry or liquid form, or a combination thereof. For example, the formulation in the first chamber can be liquid and the formulation in the second chamber can be dry, both can be dry, or both can be liquid.

Dose units that provide for controlled release of prodrug, of inhibitor, or of both prodrug and inhibitor are contemplated by the present disclosure, where "controlled release"

refers to release of one or both of prodrug and inhibitor from the dose unit over a selected period of time and/or in a pre-selected manner.

Methods of Use of Dose Units

Dose units are advantageous because they find use in methods to reduce side effects and/or improve tolerability of drugs to patients in need thereof by, for example, limiting a PK parameter as disclosed herein. The present disclosure thus provides methods to reduce side effects by administering a dose unit of the present disclosure to a patient in need so as to provide for a reduction of side effects as compared to those associated with administration of drug and/or as compared to administration of prodrug without inhibitor. The present disclosure also provides methods to improve tolerability of drugs by administering a dose unit of the present disclosure to a patient in need so as to provide for improvement in tolerability as compared to administration of drug and/or as compared to administration of prodrug without inhibitor.

Dose units find use in methods for increasing patient compliance of a patient with a therapy prescribed by a clinician, where such methods involve directing administration of a dose unit described herein to a patient in need of therapy so as to provide for increased patient compliance as compared to a therapy involving administration of drug and/or as compared to administrations of prodrug without inhibitor. Such methods can help increase the likelihood that a clinician-specified therapy occurs as prescribed.

Dose units can provide for enhanced patient compliance and clinician control. For example, by limiting a PK parameter (e.g., such as drug Cmax or drug exposure) when multiples (e.g., two or more, three or more, or four or more) dose units are ingested, a patient requiring a higher dose of drug must seek the assistance of a clinician. The dose units can provide for control of the degree to which a patient can readily "self-medicate", and further can provide for the patient to adjust dose to a dose within a permissible range. Dose units can provide for reduced side effects, by for example, providing for delivery of drug at an efficacious dose but with a modified PK profile over a period of treatment, e.g., as defined by a decreased PK parameter (e.g., decreased drug Cmax, decreased drug exposure).

Dose units find use in methods to reduce the risk of unintended overdose of drug that can follow ingestion of multiple doses taken at the same time or over a short period of time. Such methods of the present disclosure can provide for reduction of risk of unintended overdose as compared to risk of unintended overdose of drug and/or as compared to risk of unintended overdose of prodrug without inhibitor. Such methods involve directing administration of a dosage described herein to a patient in need of drug released by conversion of the prodrug. Such methods can help avoid unintended overdosing due to intentional or unintentional misuse of the dose unit.

The present disclosure provides methods to reduce misuse and abuse of a drug, as well as to reduce risk of overdose, that can accompany ingestion of multiples of doses of a drug, e.g., ingested at the same time. Such methods generally involve combining in a dose unit a prodrug and an inhibitor of a GI enzyme that mediates release of drug from the prodrug, where the inhibitor is present in the dose unit in an amount effective to attenuate release of drug from the prodrug, e.g., following ingestion of multiples of dose units by a patient. Such methods provide for a modified concentration-dose PK profile while providing therapeutically effective levels from a single dose unit, as directed by the prescribing clinician. Such methods can provide for, for example, reduction of risks that can accompany misuse and/or abuse of a prodrug, particularly where conversion of the prodrug provides for release of a narcotic or other drug of abuse (e.g., amphetamine). For example, when the prodrug provides for release of a drug of abuse, dose units can provide for reduction of reward that can follow ingestion of multiples of dose units of a drug of abuse.

Dose units can provide clinicians with enhanced flexibility in prescribing drug. For example, a clinician can prescribe a dosage regimen involving different dose strengths, which can involve two or more different dose units of prodrug and inhibitor having different relative amounts of prodrug, different amounts of inhibitor, or different amounts of both prodrug and inhibitor. Such different strength dose units can provide for delivery of drug according to different PK parameters (e.g., drug exposure, drug Cmax, and the like as described herein). For example, a first dose unit can provide for delivery of a first dose of drug following ingestion, and a second dose unit can provide for delivery of a second dose of drug following ingestion. The first and second prodrug doses of the dose units can be different strengths, e.g., the second dose can be greater than the first dose. A clinician can thus prescribe a collection of two or more, or three or more dose units of different strengths, which can be accompanied by instructions to facilitate a degree of self-medication, e.g., to increase delivery of an amphetamine drug according to a patient's needs to treat ADHD, CFS, brain injury, narcolepsy, or obesity.

Thwarting Tampering by Trypsin Mediated Release of Amphetamine from Prodrugs

The disclosure provides for a composition comprising a compound disclosed herein and a trypsin inhibitor that reduces drug abuse potential. A trypsin inhibitor can thwart the ability of a user to apply trypsin to effect the release of amphetamine from the amphetamine prodrug in vitro. For example, if an abuser attempts to incubate trypsin with a composition of the embodiments that includes an amphetamine prodrug and a trypsin inhibitor, the trypsin inhibitor can reduce the action of the added trypsin, thereby thwarting attempts to release amphetamine for purposes of abuse.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Example 1
Synthesis of Amphetamine Prodrug Compounds
Synthesis of Amphetamine-arginine-acetate (Compound AM-1; also referred to as 2-acetylamino-5-guanidino-pentanoic acid ((R)-1-methyl-2-phenyl-ethyl)-amide) and Amphetamine-arginine-malonic acid (Compound AM-2; also referred to as N-[4-guanidino-1-((R)-1-methyl-2-phenyl-ethylcarbamoyl)-butyl]-malonic acid)
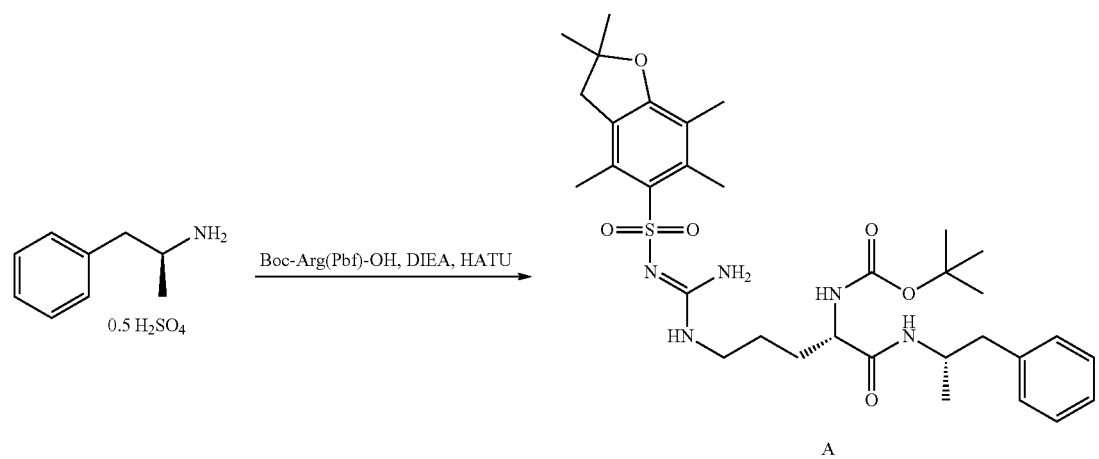
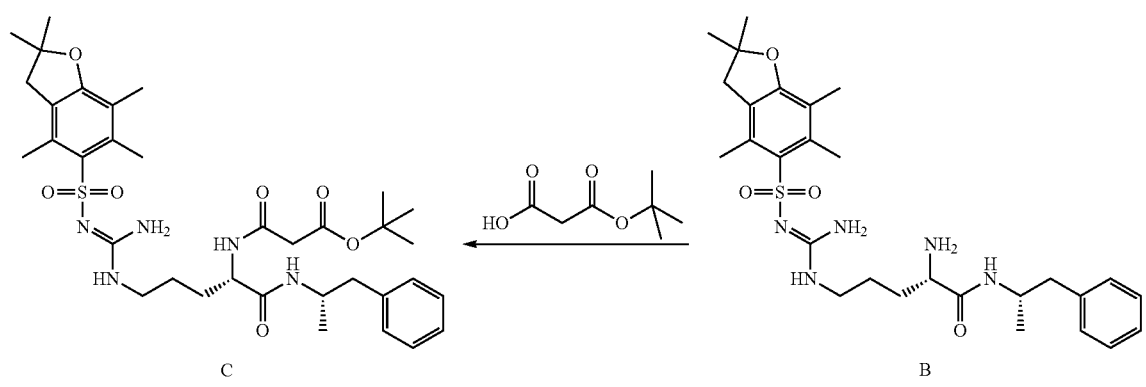

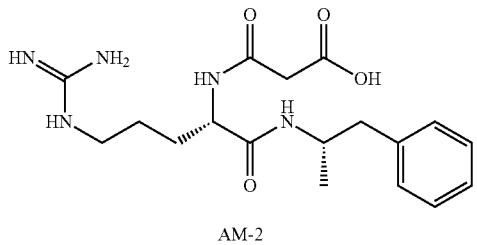

AM-2

-continued

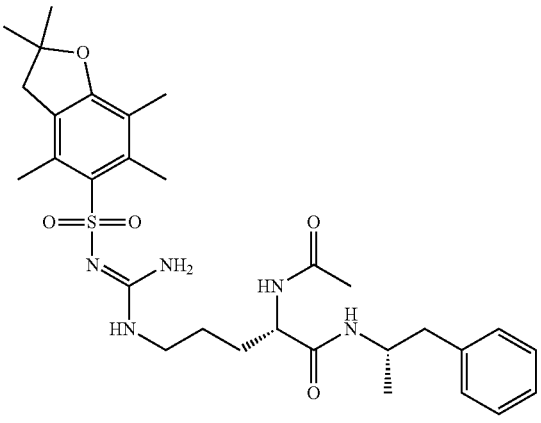

D

1. TFA/m-cresol
2. i-PrOH, HCl/ether

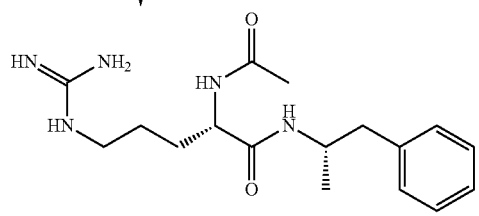

AM-1

Preparation of Compound A

D-Amphetamine sulfate (5.0 g, 27.1 mmol), Boc-Arg (Pbf)-OH (10.0 g, 19.0 mmol) and HATU (10.8 g, 28.5 mmol) were suspended in DMF (100 mL), brought to 5° C. and treated drop wise with DIEA (13.3 mL, 76.0 mmol) over 10 min. The reaction mixture was stirred at 5° C. for an additional 10 min, warmed to ambient temperature, followed by stirring for 30 min. The reaction was then diluted with EtOAc (400 mL) and poured into water (600 mL). The layers were separated, the aqueous layer extracted with EtOAc (3×300 mL) and the combined organic layers washed with 2% aq. $H_2SO_4$ (150 mL), water (2×600 mL) and brine (600 mL). The organic layer was dried over $MgSO_4$, filtered and concentrated in vacuo to give compound A in quantitative yield (13.9 g, 19.0 mmol) as a light-yellow foamy solid. LC-MS [M+H] 644.7 ($C_{33}H_{49}N_5O_6S$+H, calc: 644.8). Compound A was used without further purification.

Preparation of Compound B

A solution of compound A (13.9 g, 19.0 mmol) in DCM (80 mL) was treated with 4 M HCl in dioxane (48 mL, 190 mmol) and the mixture stirred at ambient temperature for 45 min. Ether (1 L) was added and the resulting white precipitate filtered, washed with ether (50 mL), hexane (50 mL) and then dried in vacuo to give compound B as an off-white solid in quantitative yield (11.9 g, 19.0 mmol). LC-MS [M+H] 544.4 ($C_{28}H_{41}N_5O_4S$+H, calc: 544.7). Compound B was used without further purification.

Preparation of Compound C

To a cooled solution (5° C.) of compound B (11.9 g, 19.0 mmol) and mono tert-butyl malonate (3.2 g, 20.0 mmol) in DMF (70 mL) was added portion wise, BOP (9.0 g, 20.3 mmol) over 5 min. This step was then followed by drop wise addition of DIEA (13.3 mL, 76.0 mmol) over 15 min. Stirring was continued for an additional 15 min, after which the ice bath was removed and the mixture warmed to ambient temperature. After 30 min at ambient temperature, the reaction mixture was diluted with EtOAc (600 mL) and poured into water (600 mL). The layers were separated and the aqueous layer extracted with EtOAc (2×300 mL). The combined organic layers were washed with 2% aq. $H_2SO_4$ (150 mL), water (2×450 mL) and brine (400 mL), followed by drying over $MgSO_4$, filtration, and finally the solvent was evaporated in vacuo. The resulting residue was dried in vacuo to give compound C in 93% yield (12.1 g, 17.6 mmol) as a yellowish foamy solid. LC-MS [M+H] 686.5 ($C_{35}H_{51}N_5O_7S$+H, calc: 685.9). Compound C was used without further purification.

Preparation of Compound AM-2

A solution of compound C (12.1 g, 17.6 mmol) in 5% m-cresol/TFA (350 mL) was stirred at ambient temperature. After 45 min, the solvent was removed in vacuo until about 100 mL volume remained, followed by dilution with hexane (500 mL). The solvent was decanted off, and the oily precipitate was concentrated in vacuo. The residue was dissolved in 0.1% TFA/$H_2O$ (125 mL), sonicated for 30 min, and the layers separated. The aqueous emulsion (140 mL total volume) cleared up after standing in the refrigerator overnight. This product was divided into four portions, and each was subjected to HPLC purification [Nanosyn-Pack Microsorb (100-10) C-18 column (50×300 mm); flow rate: 100 mL/min; injection volume: 40 mL; mobile phase A: 100% water, 0.1% TFA; mobile phase B: 100% ACN, 0.1% TFA; isocratic elution at 0% B in 2 min, gradient elution to 8% B in 12 min, isocratic elution at 8% B in 30 min, gradient elution from 8% B to 33% B in 51 min; detection at UV 254 nm]. Fractions containing the desired compound were combined and concentrated in vacuo to yield the TFA salt of Compound AM-2 in 38% yield (4.0 g, 6.7 mmol, 96% purity) as colorless viscous oil. A part of this material (640 mg, 1.06 mmol) was dissolved in i-PrOH (3 mL) and treated with 2 N HCl in ether (30 mL, 60 mmol) to give the hydrochloride salt of Compound AM-2 (430 mg, 0.95 mmol, 99% purity). LC-MS [M+H] 378.3 ($C_{18}H_{27}N_5O_4$+H, calc: 378.4). Retention time [Chromolith SpeedRod RP-18e C18 column (4.6×50 mm); flow rate: 1.5 ml/min; mobile phase A: 0.1% TFA/water; mobile phase B 0.1% TFA/ACN; gradient elution from 5% B to 100% B over 9.6 min, detection 254 nm]: 2.15 min.

Preparation of Compound D

To a solution of compound B (3.3 g, 5.0 mmol) in chloroform (30 mL) was added DIEA (2.3 mL, 13.1 mmol) and acetic anhydride (697 mg, 6.8 mmol). After stirring at ambient temperature for 30 min, the mixture was treated with 2 M $EtNH_2$ in THF (2.8 mL, 1.8 mmol). Stirring was continued for an additional 30 min. The solvent was then removed in vacuo, and the residue acidified to pH ~3 with 2% aq. $H_2SO_4$ and extracted with EtOAc (3×100 mL). The combined organic layers were washed with water (150 mL), sat. $NaHCO_3$ solution (150 mL) and brine (150 mL) After drying over $MgSO_4$, the solvent was evaporated in vacuo to give compound D in 95% yield (2.8 g, 4.8 mmol) as a colorless foamy solid. LC-MS [M+H] 586.2 ($C_{30}H_{43}N_5O_5S$+H, calc: 586.8). Compound D was used without further purification.

Preparation of Compound AM-1

A solution of compound D (2.8 g, 4.8 mmol) in 5% m-cresol/TFA (70 mL) was stirred at ambient temperature. After 45 min, TFA was evaporated and the residue taken into MeOH (10 mL), diluted with hexane (400 mL) and cooled in the refrigerator (4° C.) for 30 min. After separation from the hexane layer, the oily precipitate was dissolved in water (30 mL) and purified by HPLC. [Nanosyn-Pack Microsorb (100-10)C-18 column (50×300 mm); flow rate: 100 mL/min; injection volume: 35 mL; mobile phase A: 100% water, 0.1% TFA; mobile phase B: 100% ACN, 0.1% TFA; isocratic elution at 5% B in 5 min, gradient elution to 12% B in 7 min, isocratic elution at 12% B in 20 min, gradient elution from 12% B to 40% B in 28 min; detection at UV 254 nm]. Fractions containing the desired compound were combined and concentrated in vacuo. Traces of water were removed by dissolving the residue in i-PrOH (50 mL) followed by evaporation in vacuo (procedure was repeated twice). The residue was dissolved in i-PrOH (20 mL) and treated with 2 N HCl in ether (100 mL, 200 mmol) to give the hydrochloride salt of Compound AM-1 in 76% yield (1.34 g, 3.6 mmol, 99% purity) LC-MS [M+H] 334.4 ($C_{17}H_{27}N_5O_2$+H, calc: 334.4). Retention time [Chromolith SpeedRod RP-18e C18 column (4.6×50 mm); flow rate: 1.5 ml/min; mobile phase A: 0.1% TFA/water; mobile phase B 0.1% TFA/ACN; gradient elution from 5% B to 100% B over 9.6 min, detection 254 nm]: 2.43 min.

Example 2

Synthesis of Amphetamine-Arginine-N-Methyl (Compound AM-4)

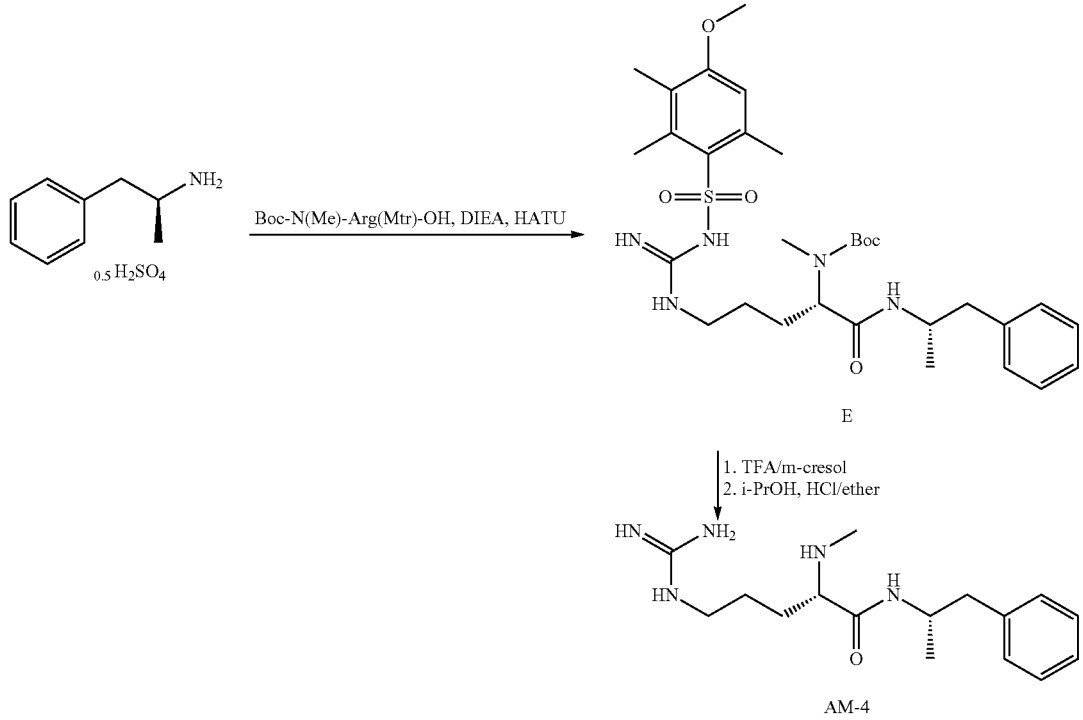

Preparation of Compound E

D-Amphetamine sulfate (496 mg, 2.68 mmol), Boc-N-Me-Arg(Mtr)-OH (940 mg, 1.88 mmol) and HATU (855 mg, 2.25 mmol) were suspended in DMF (20 mL), cooled to 5° C. and treated drop wise with DIEA (1.9 mL, 10.7 mmol) over 5 min. After addition, the reaction mixture was stirred at 5° C. for an additional 10 min. Next, the reaction was warmed to ambient temperature and stirred for 30 min. The reaction was then diluted with EtOAc (250 mL) and poured into water (200 mL). The layers were separated, the aqueous layer extracted with EtOAc (2×150 mL), and the combined organic layers washed with 2% aq. $H_2SO_4$ (50 mL), water (2×300 mL) and brine (200 mL). The organic layer was dried over MgSO₄, filtered and concentrated in vacuo to give compound E in quantitative yield (1.28 g, 1.88 mmol) as a colorless foamy solid. LC-MS [M+H] 618.6 ($C_{31}H_{47}N_5O_6S$+H, calc: 618.3). Compound E was used without further purification.

Preparation of Compound AM-4

A solution of compound E (1.28 g, 1.88 mmol) in 5% m-cresol/TFA (50 mL) was stirred at ambient temperature. After 6 h, the solvent was removed in vacuo until about 15 mL remained. The mixture was diluted with hexane (300 mL) and resulted in the formation of an oily precipitate. Hexane was decanted off and the oily precipitate was concentrated in vacuo to remove traces of hexane. The residue was dissolved in 0.1% TFA/H₂O (25 mL), sonicated for 10 min and subjected to HPLC purification [Nanosyn-Pack Microsorb (100-10) C-18 column (50×300 mm); flow rate: 100 mL/min; injection volume: 28 mL; mobile phase A: 100% water, 0.1% TFA; mobile phase B: 100% ACN, 0.1% TFA; gradient elution from 0 to 10% B in 10 min, isocratic elution at 10% B in 25 min, gradient elution from 10% B to 42% B in 55 min; detection at UV 254 nm]. Fractions containing the desired compound were combined and concentrated in vacuo. The residue was dissolved in toluene (30 mL, to remove traces of water) and co-evaporated in vacuo (procedure repeated twice). The residue was dissolved in ACN (5 mL), treated with 2.0 M HCl in ether (50 mL) followed by dilution with ether (200 mL). The resulting solid was filtered, washed with ether (3×30 mL) and hexane (40 mL) and dried in vacuo to provide the hydrochloride salt of Compound AM-4 in 48% yield (400.6 mg, 0.90 mmol) as a white solid. LC-MS [M+H] 306.4 ($C_{16}H_{27}N_5O$+H, calc: 306.2). Purity ~94% (UV/254 nm).

Example 3

Synthesis of Amphetamine-Lysine-Acetate (Compound AM-5)

AM-5

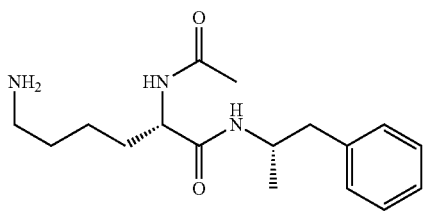

Compound AM-5 was prepared following the method described in Example 1 to prepare Amphetamine-arginine-acetate (Compound AM-1), but using Fmoc-Lys(Boc)-OH instead of Boc-Arg(Pbf)-OH, piperidine instead of HCl in dioxane (for deprotection of Fmoc group on α-nitrogen of Lys), and lastly HCl in dioxane for Boc deprotection of the Lys reside. LC-MS [M+H] 306.6 ($C_{17}H_{28}N_3O_2$+H, calc: 306.2).

Example 4

Synthesis of Amphetamine-Arginine (Compound AM-6)

AM-6

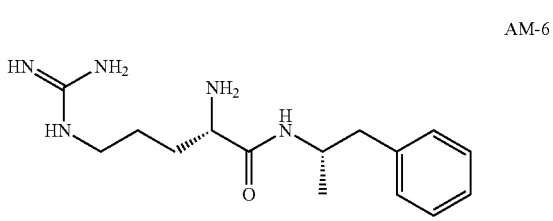 [SMILES: C[C@@H](Cc1ccccc1)NC(=O)[C@@H](N)CCCNC(=N)N]

Compound AM-6 was prepared following the method described in Example 1 to prepare Amphetamine-arginine-acetate (Compound AM-1), but skipping the step involving the use of acetic anhydride. LC-MS [M+H] 291.4 ($C_{15}H_{26}N_5O$+H, calc: 292.2).

Biological Data

Example 5

In Vitro Trypsin Conversion of Prodrugs to Amphetamine and Inhibition by Trypsin Inhibitor This Example demonstrates the ability of trypsin to cleave a prodrug of the embodiments to effect amphetamine release and the effect of trypsin inhibitors on such cleavage. This Example also determines the ability of trypsin to cleave lisdexamphetamine.

Compound AM-1 and Compound AM-2 (each of which can be prepared as described in Examples herein) and Compound AM-3 (lisdexamphetamine, available from Shire Pharmaceuticals, Wayne, Pa. (Vyvanse®)) were each incubated with trypsin from bovine pancreas (Catalog No. T8003, Type I, ~10,000 BAEE units/mg protein, Sigma-Aldrich, St. Louis, Mo.) in the absence or presence of trypsin inhibitor, Compound 109 (Catalog No. 3081, Tocris Bioscience, Ellisville, Mo.). The reactions included 0.761 mM Compound AM-1•HCl, Compound AM-2•HCl or Compound AM-3•HCl in the presence of 0.0228 mg/ml trypsin, 22.5 mM calcium chloride, 172 mM Tris pH 8 and either 0.25% DMSO or Compound 109 as indicated in Table 1, depending on whether inhibitor was included in the incubation. The reactions were conducted at 37° C. for 24 hr. When Compound 109 was part of the incubation mixture, the respective prodrug was added 5 min after the other incubation components. Samples were collected at specified time points, transferred into 0.5% formic acid in acetonitrile to stop trypsin activity and stored at less than −70° C. until analysis by LC-MS/MS.

Table 1 indicates the results of exposure of the test compounds to trypsin in the absence or presence of trypsin inhibitor. The results are expressed as half-life of prodrug when exposed to trypsin (i.e., prodrug trypsin half-life) in hours and rate of amphetamine formulation in umols/h/U BAEE.

TABLE 1

In vitro trypsin conversion of prodrugs to amphetamine and inhibition by trypsin inhibitor

| | No trypsin inhibitor | | | With trypsin inhibitor | |
|---|---|---|---|---|---|
| Prodrug | Pro-drug trypsin half-life, h Ave ± sd | Rate of AMP formation, umols/h/U BAEE Ave ± sd | Compound 109 | Pro-drug trypsin half-life, h Ave ± sd | Rate of AMP formation, umols/h/U BAEE Ave ± sd |
| AM-1 | 39.9 ± 0.5 | 0.0455 ± 0.0102 | 2 uM | 54.0 ± 4.6 | nd |
| AM-2 | 59.9 ± 17.1 | 0.0310 ± 0.0004 | 2 uM | 68.5 ± 16.4 | nd |
| AM-3 | 112 ± 14 | nd | 2 uM | 393 ± 431 | nd | nd = not detectable

The results in Table 1 indicated that trypsin released amphetamine from Compound AM-1 and Compound AM-2 and that a trypsin inhibitor of the embodiments attenuated trypsin-mediated release of amphetamine. The rate of formation of amphetamine from Compound AM-3 was not detectable showing that trypsin did not efficiently release amphetamine from Compound AM-3.

Example 6

Pharmacokinetics of Compound AM-1 Following PO Administration to Rats

This Example compares the pharmacokinetics of two concentrations of Compound AM-1 administered orally (PO) to rats.

Saline solutions of Compound AM-1 (which can be prepared as described in Examples herein) were dosed as indicated in Table 2 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice and then stored in a −80° C. freezer until analysis by HPLC/MS.

Figure 4A:
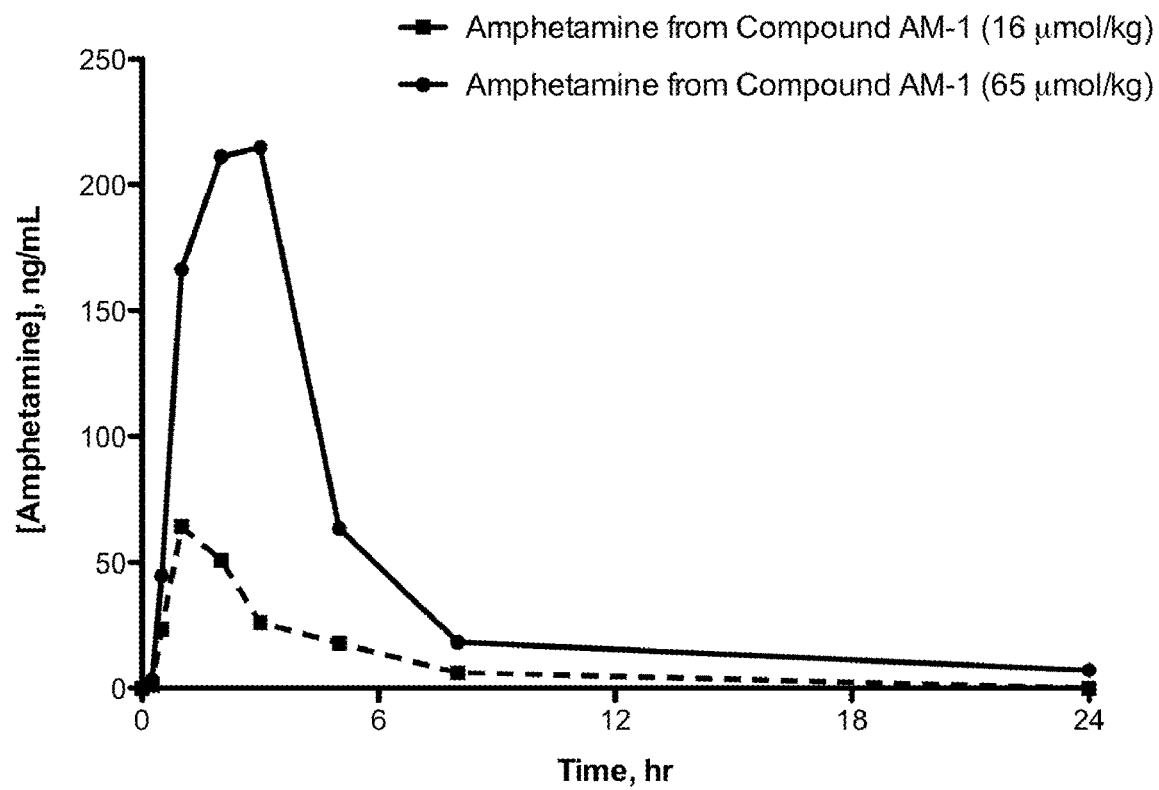
FIGS. 4(a) and 4(b) provide graphs of amphetamine exposure results for rats administered with different doses of Compound AM-1 according to embodiments of the present disclosure.
Figure 4B:
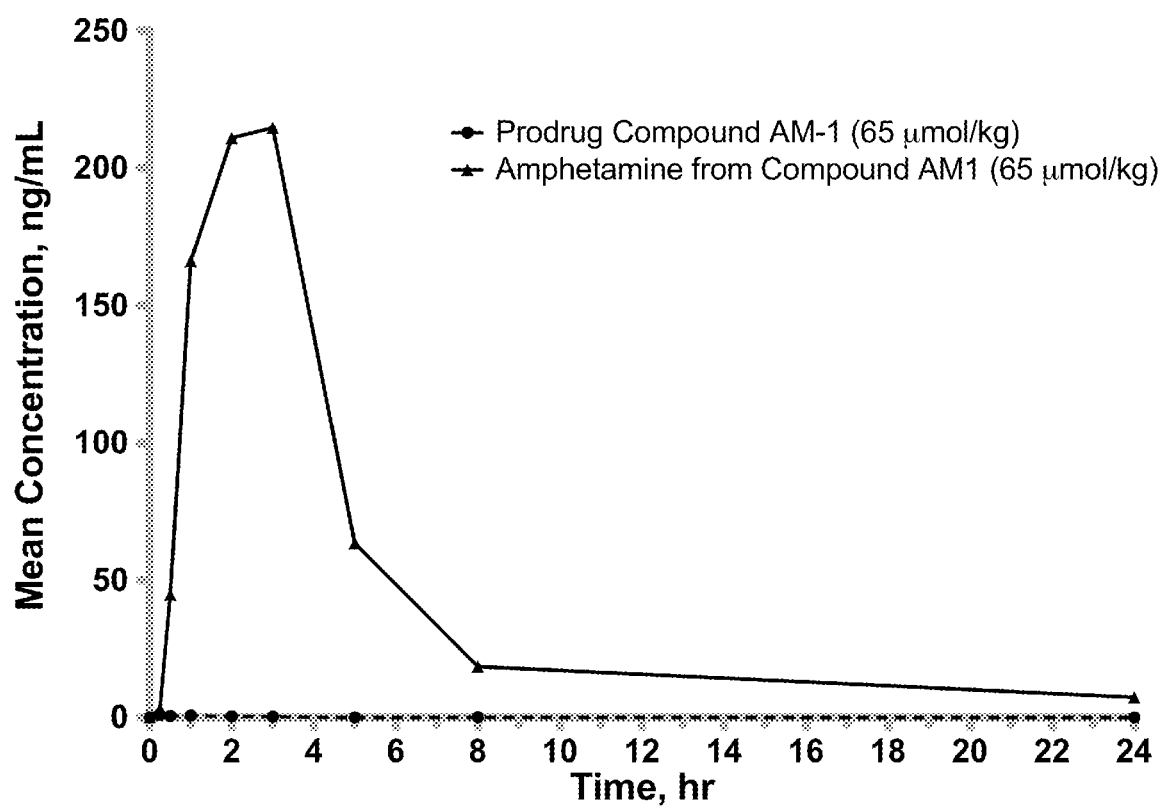

Table 2, FIG. 4(a) and FIG. 4(b) provide amphetamine exposure results for rats administered with different doses of Compound AM-1. Table 2 and FIG. 4(b) also provide prodrug exposure results for rats administered the higher dose of Compound AM-1. Results in Table 2 are reported, for each group of 4 rats, as (a) maximum plasma concentration (Cmax) of prodrug Compound AM-1 (average±standard deviation), (b) time after administration of Compound AM-1 to reach maximum prodrug Compound AM-1 concentration (Tmax) (average±standard deviation), (c) maximum plasma concentration (Cmax) of amphetamine (AMP) (average±standard deviation) and (d) time after administration of Compound AM-1 to reach maximum amphetamine concentration (Tmax) (average±standard deviation).

TABLE 2

Cmax and Tmax values of prodrug Compound AM-1 and amphetamine in rat plasma

| Compound | Dose, mg/kg | Dose, μmol/kg | Prodrug AM-1 Cmax ± sd, ng/mL | Prodrug AM-1 Tmax ± sd, hr | AMP Cmax ± sd, ng/mL | AMP Tmax ± sd, hr |
|---|---|---|---|---|---|---|
| AM-1 | 6 | 16 | na | na | 64.2 ± 10 | 1.0 ± 0.0 |
| AM-1 | 24 | 65 | 1.28 ± 0.81 | 0.625 ± 0.43 | 248 ± 40 | 2.0 ± 0.8 |

Lower limit of quantitation for AMP for the 6-mg/kg dose was 1.000 ng/mL.
Lower limits of quantitation for prodrug and AMP for the 24-mg/kg dose were 0.100 and 0.500 ng/ml, respectively.
na = not analyzed FIG. 4(a) compares mean plasma concentrations over time of amphetamine release following PO administration of increasing doses of Compound AM-1. FIG. 4(b) compares mean plasma concentrations over time of prodrug disappearance and of amphetamine release following PO administration of Compound AM-1.

The results in Table 2, FIG. 4(a) and FIG. 4(b) indicate that plasma concentrations of amphetamine increased proportionally with Compound AM-1 dose. The results further indicated that the mean concentration of prodrug in plasma following oral administration of Compound AM-1 was very low, particularly as compared to the concentrations of Compound AM-2 (see Example 10) or lisdexamphetamine (see Example 14).

Example 7

Oral Administration of Compound AM-1 and Trypsin Inhibitor Compound 109 to Rats This Example demonstrates the ability of a trypsin inhibitor of the embodiments to affect drug release into plasma from Compound AM-1 administered orally.

Saline solutions of Compound AM-1 (which can be prepared as described in Examples herein) were dosed at 16 μmol/kg (6 mg/kg) with or without a co-dose of 55 μmol/kg (30 mg/kg) Compound 109 (Catalog No. 3081, Tocris Bioscience or Catalog No. WS38665, Waterstone Technology, Carmel, Ind.) as indicated in Table 3 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 μl plasma transferred from each sample into a fresh tube containing 2 μl of 50% formic acid. The tubes were vortexed for 5-10 seconds, immediately placed in dry ice and then stored in a −80° C. freezer until analysis by HPLC/MS.

Figure 5:
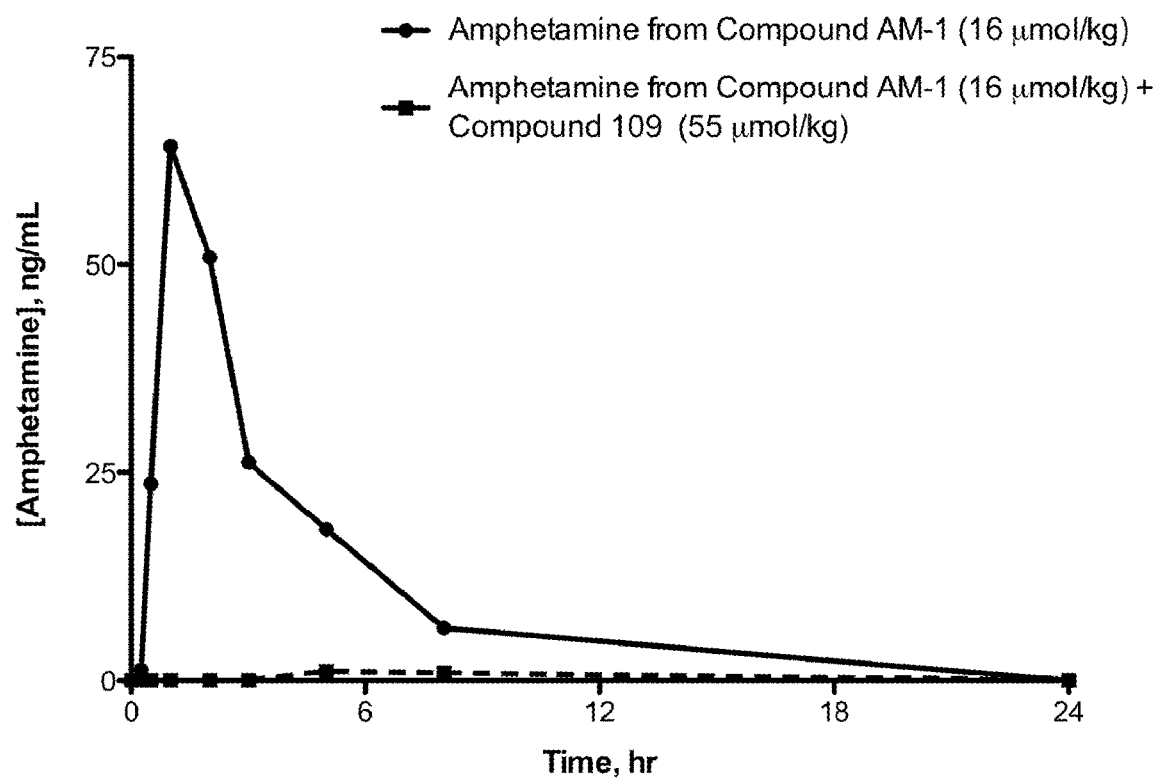
FIG. 5 provides a graph of mean plasma concentrations over time of amphetamine release following PO administration of Compound AM-1 with or without a co-dose of trypsin inhibitor according to embodiments of the present disclosure.

Table 3 and FIG. 5 provide amphetamine exposure results for rats administered with Compound AM-1 and with or without a co-dose of trypsin inhibitor. Results in Table 3 are reported, for each group of 4 rats, as (a) maximum plasma concentration (Cmax) of amphetamine (AMP) (average±standard deviation) and (b) time after administration of Compound AM-1, to reach maximum amphetamine concentration (Tmax) (average±standard deviation).

TABLE 3

Cmax and Tmax values of amphetamine in rat plasma

| AM-1 Dose, mg/kg | AM-1 Dose, µmol/kg | Compound 109 Dose, mg/kg | Compound 109 Dose, µmol/kg | AMP Cmax ± sd, ng/mL | Tmax ± sd, hr |
|---|---|---|---|---|---|
| 6 | 16 | 0 | 0 | 64.2 ± 10 | 1.0 ± 0.0 |
| 6 | 16 | 30 | 55 | 2.08 ± 2.4 | 6.5 ± 2.1 |

Lower limit of quantitation was 1.000 ng/mL.

FIG. 5 compares mean plasma concentrations over time of amphetamine release following PO administration of Compound AM-1 with or without a co-dose of trypsin inhibitor.

The results in Table 3 and FIG. 5 indicated Compound 109's ability to attenuate Compound AM-1's ability to release amphetamine both by suppressing Cmax and by delaying Tmax.

Example 8

Pharmacokinetics of Compound AM-1 Following IV Administration to Rats

This Example compares the plasma concentrations of prodrug and amphetamine in rats following intravenous (IV) administration of Compound AM-1.

Compound AM-1 (which can be prepared as described in Examples herein) was dissolved in saline and injected into the tail vein of 4 jugular vein-cannulated male Sprague Dawley rats at a dose of 5 mg/kg. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in a −80° C. freezer until analysis by high performance liquid chromatography/mass spectrometry (HPLC/MS).

Figure 6:
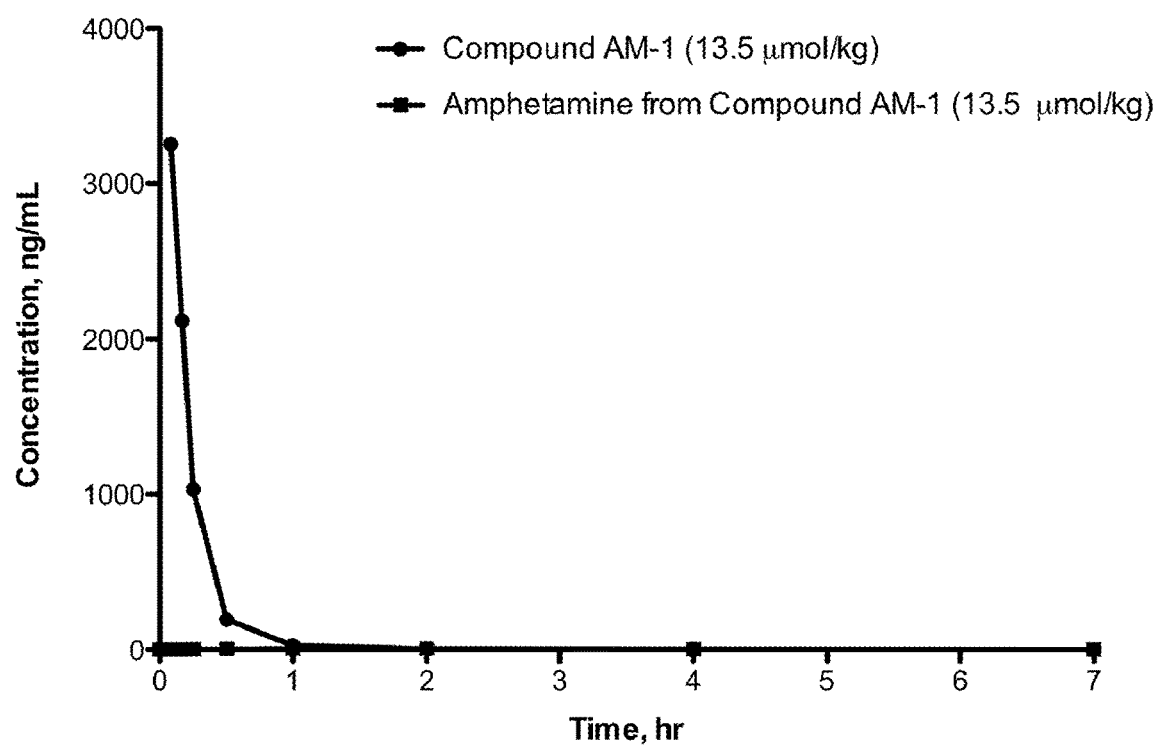
FIG. 6 provides a graph of mean plasma concentrations over time of Compound AM-1 and amphetamine following IV administration of Compound AM-1 to rats according to embodiments of the present disclosure.

Table 4 and FIG. 6 provide Compound AM-1 and amphetamine exposure results for the group of rats administered Compound AM-1 intravenously. Results in Table 4 are reported as maximum plasma concentration (Cmax) values (average±standard deviation) of Compound AM-1 and amphetamine, respectively.

TABLE 4

Cmax values of Compound AM-1 and amphetamine in rat plasma

| Compound | AM-1 Dose, mg/kg | AM-1 Dose, µmol/kg | AM-1 Cmax ± sd, ng/mL* | AMP Cmax ± sd, ng/mL^ |
|---|---|---|---|---|
| AM-1 | 5 | 13.5 | 3250 ± 310 | 7.48 ± 1.7 |

*Lower limit of quantitation was 0.100 ng/mL
^Lower limit of quantitation was 0.500 ng/mL FIG. 6 compares mean plasma concentrations over time of Compound AM-1 and amphetamine following IV administration of Compound AM-1 to rats.

Table 4 and FIG. 6 demonstrate that the plasma concentration of amphetamine in rats administered Compound AM-1 intravenously is only 0.23% of the plasma concentration of Compound AM-1, indicating that IV administration of Compound AM-1 does not lead to significant release of amphetamine.

Example 9

In Vivo Tolerability of Compound AM-1 in Rats

This Example demonstrates that Compound AM-1 was tolerated when administered intravenously to rats.

Male naïve Sprague-Dawley rats, 4 per dose, were used in the study. Rats were weighed, and then placed under a heat lamp for 15-20 minutes to dilate the lateral tail veins. Dose volumes are based on the body weights (1 mL/kg); dosing of Compound AM-1 (which can be prepared as described in Example 1 above) was as indicated in Table 5. Before dosing, rats were placed in Broome restrainers and the drug was introduced into one of the tail veins using a syringe and needle. After dosing, the timer was set and rats were observed for clinical signs. Blood samples were collected 5 minutes post-dose via the saphenous vein. The rats were observed up to 24 hours. Results are shown in Table 5.

TABLE 5

In vivo tolerability of Compound AM-1 in rats

| Compound | Dose, mg/kg | Dose, µmol/kg | Number of Rats dosed | Clinical observations |
|---|---|---|---|---|
| AM-1 | 32 | 87 | 4 | Whole body tremors for 13-30 sec; followed by hypoactivity, then normal after 2 min |

The results in Table 5 indicated that rats tolerate a dose of 87 µmol/kg of Compound AM-1 and recover to normal activity within 2 minutes.

Example 10

Pharmacokinetics of Compound AM-2 Following PO Administration to Rats

This Example compares the pharmacokinetics of two concentrations of Compound AM-2 administered orally (PO) to rats.

Saline solutions of Compound AM-2 (which can be prepared as described in Example 1 above) were dosed as indicated in Table 6 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in −80° C. freezer until analysis by HPLC/MS.

Figure 7A:
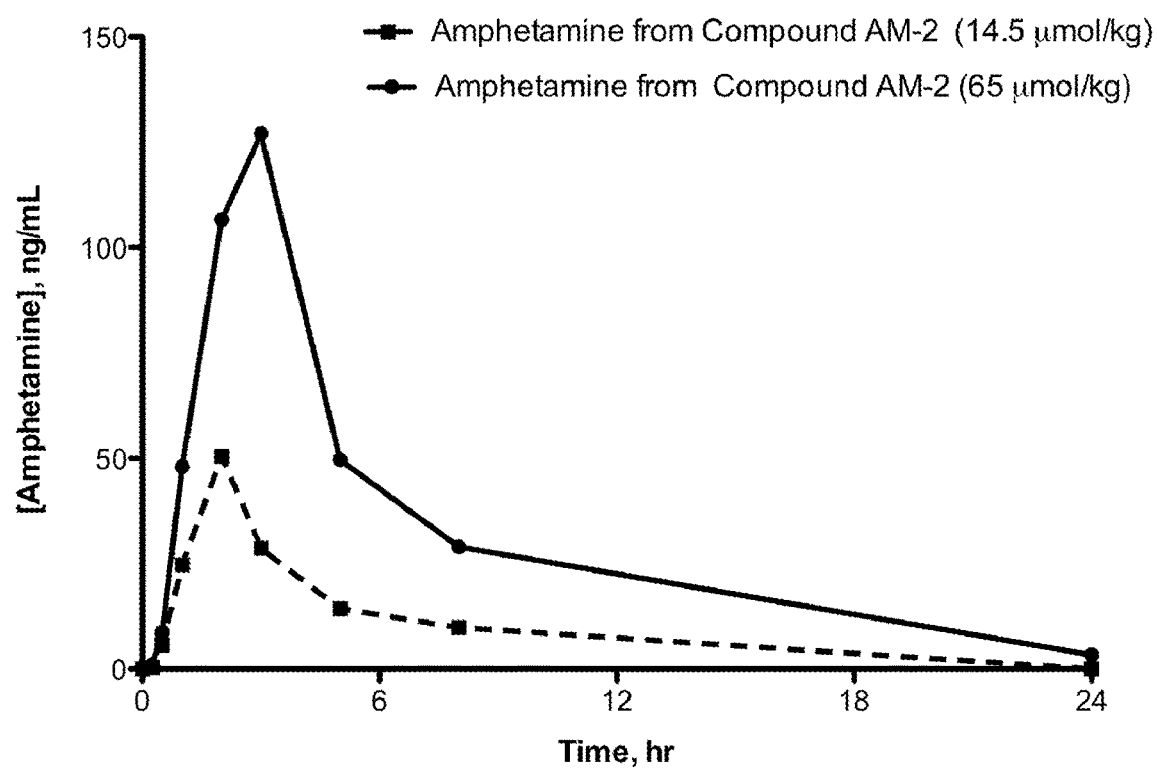
FIGS. 7(a) and 7(b) provide graphs of amphetamine exposure results for rats administered with different doses of Compound AM-2 according to embodiments of the present disclosure.
Figure 7B:
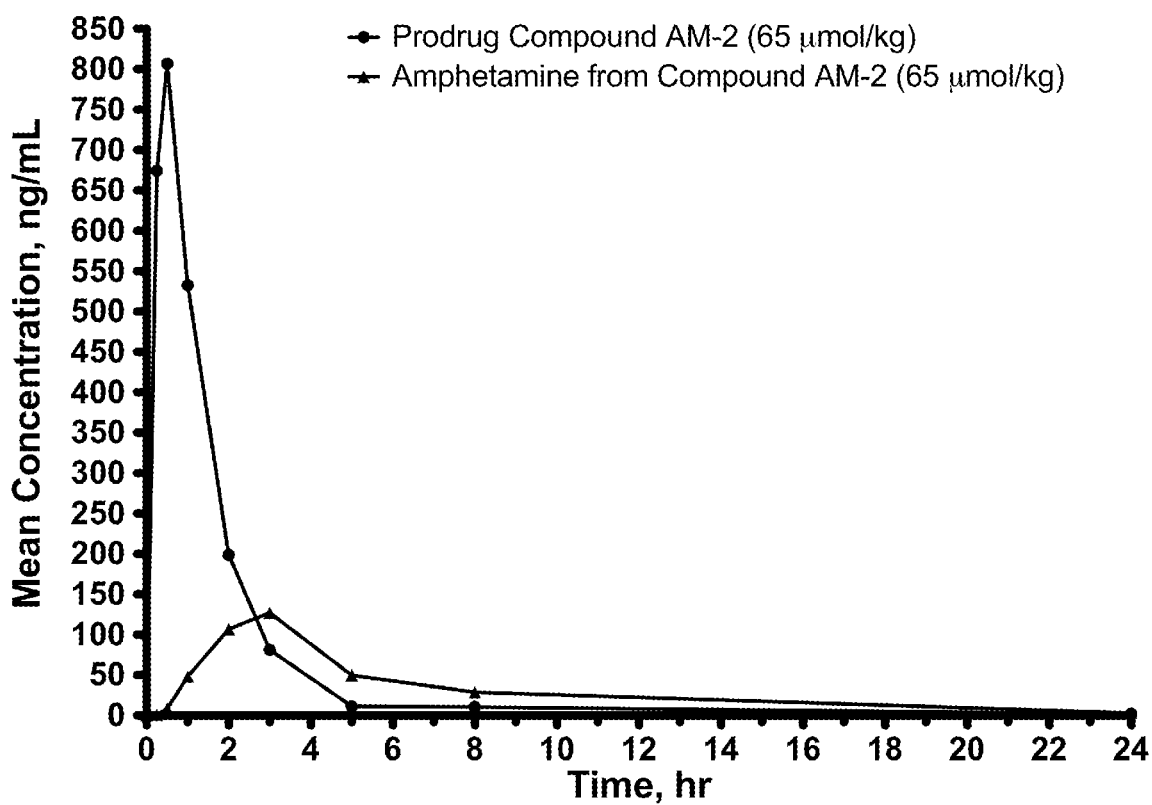

Table 6, FIG. 7(a) and FIG. 7(b) provide amphetamine exposure results for rats administered with different doses of Compound AM-2. Table 6 and FIG. 7(b) also provide prodrug exposure results for rats administered the higher dose of Compound AM-2. Results in Table 6 are reported, for each group of 4 rats, as (a) maximum plasma concentration (Cmax) of prodrug Compound AM-2 (average±standard deviation), (b) time after administration of Compound AM-2 to reach maximum prodrug Compound AM-2 concentration (Tmax) (average±standard deviation), (c) maximum plasma concentration (Cmax) of amphetamine (AMP) (average±standard deviation) and (d) time after administration of Compound AM-2 to reach maximum amphetamine concentration (Tmax) (average±standard deviation).

TABLE 6

Cmax and Tmax values of prodrug Compound AM-2 and amphetamine in rat plasma

| Compound | Dose mg/kg | Dose µmol/kg | Prodrug AM-2 Cmax ± sd ng/mL | Prodrug AM-2 Tmax ± sd, hr | AMP Cmax ± sd, ng/mL | AMP Tmax ± sd, hr |
|---|---|---|---|---|---|---|
| AM-2 | 6 | 14.5 | na | na | 50.6 ± 6.3 | 2.0 ± 0.0 |
| AM-2 | 27 | 65 | 811 ± 850 | 0.625 ± 0.25 | 127 ± 31 | 3.0 ± 0.0 |

Lower limit of quantitation for AMP for the 6-mg/kg dose was 1.000 ng/mL.
Lower limits of quantitation for prodrug and AMP for the 27-mg/kg dose were 0.100 and 0.500 ng/ml, respectively.
na = not analyzed FIG. 7(a) compares mean plasma concentrations over time of amphetamine release following PO administration of increasing doses of Compound AM-2. FIG. 7(b) compares mean plasma concentrations over time of prodrug disappearance and of amphetamine release following PO administration of Compound AM-2.

The results in Table 6, FIG. 7(a) and FIG. 7(b) indicate that plasma concentrations of amphetamine increase proportionally with Compound AM-2 dose. The results further indicate that, when both compounds were administered orally at 65 µmol/kg, the mean concentration of prodrug Compound AM-2 in plasma was significantly higher than that of Compound AM-1 (see Example 6).

Example 11

Oral Administration of Compound AM-2 and Trypsin Inhibitor Compound 109 to Rats

This Example demonstrates the ability of a trypsin inhibitor of the embodiments to affect drug release into plasma from Compound AM-2 administered orally.

Saline solutions of Compound AM-2 (which can be prepared as described in Examples herein) were dosed at 16 µmol/kg (6 mg/kg) with or without a co-dose of 55 µmol/kg (30 mg/kg) Compound 109 (Catalog No. 3081, Tocris Bioscience or Catalog No. WS38665, Waterstone Technology) as indicated in Table 7 via oral gavage into jugular vein-cannulated male Sprague Dawley rats (4 per group) that had been fasted for 16-18 hr prior to oral dosing. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in a −80° C. freezer until analysis by HPLC/MS.

Figure 8:
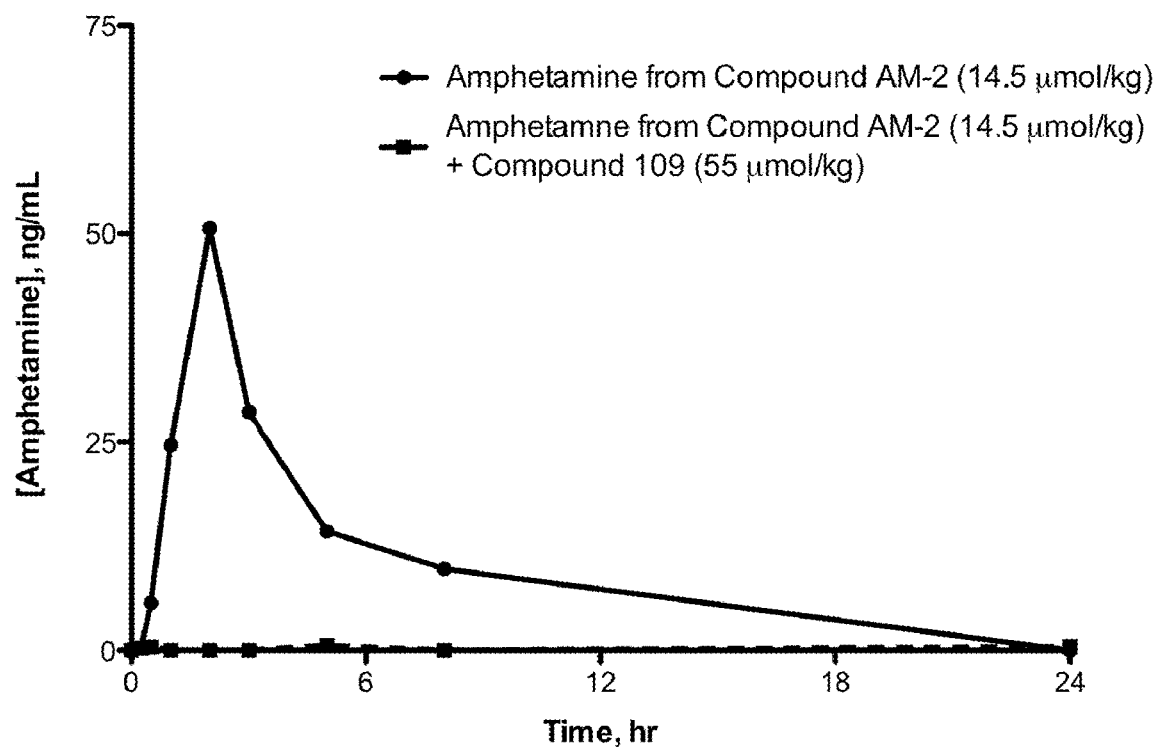
FIG. 8 shows a graph of mean plasma concentrations over time of amphetamine release following PO administration of Compound AM-2 with or without a co-dose of trypsin inhibitor according to embodiments of the present disclosure.

Table 7 and FIG. 8 provide amphetamine exposure results for rats administered with Compound AM-2 and with or without a co-dose of trypsin inhibitor. Results in Table 7 are reported, for each group of 4 rats, as (a) maximum plasma concentration (Cmax) of amphetamine (AMP) (average±standard deviation) and (b) time after administration of Compound AM-2, to reach maximum amphetamine concentration (Tmax) (average±standard deviation).

TABLE 7

Cmax and Tmax values of amphetamine in rat plasma

| AM-2 Dose, mg/kg | AM-2 Dose, µmol/kg | Compound 109 Dose, mg/kg | Compound 109 Dose, µmol/kg | AMP Cmax ± sd, ng/mL | Tmax ± sd, hr |
|---|---|---|---|---|---|
| 6 | 14.5 | 0 | 0 | 50.6 ± 6.3 | 2.0 ± 0.0 |
| 6 | 14.5 | 30 | 55 | 0.91 ± 1.1 | 12.3 ± 17 |

Lower limit of quantitation was 1.000 ng/mL.

FIG. 8 compares mean plasma concentrations over time of amphetamine release following PO administration of Compound AM-2 with or without a co-dose of trypsin inhibitor.

The results in Table 7 and FIG. 8 indicated Compound 109's ability to attenuate Compound AM-2's ability to release amphetamine both by suppressing Cmax and by delaying Tmax.

Example 12

Pharmacokinetics of Compound AM-2 Following IV Administration to Rats

This Example compares the plasma concentrations of prodrug and amphetamine in rats following intravenous (IV) administration of Compound AM-2.

Compound AM-2 (which can be prepared as described in Examples herein) was dissolved in saline and injected into the tail vein of 4 jugular vein-cannulated male Sprague Dawley rats at a dose of 6 mg/kg. At specified time points, blood samples were drawn, harvested for plasma via centrifugation at 5,400 rpm at 4° C. for 5 min, and 100 µl plasma transferred from each sample into a fresh tube containing 2 µl of 50% formic acid. The tubes were vortexed for 5-10 seconds, immediately placed in dry ice and then stored in a −80° C. freezer until analysis by high performance liquid chromatography/mass spectrometry (HPLC/MS).

Figure 9:
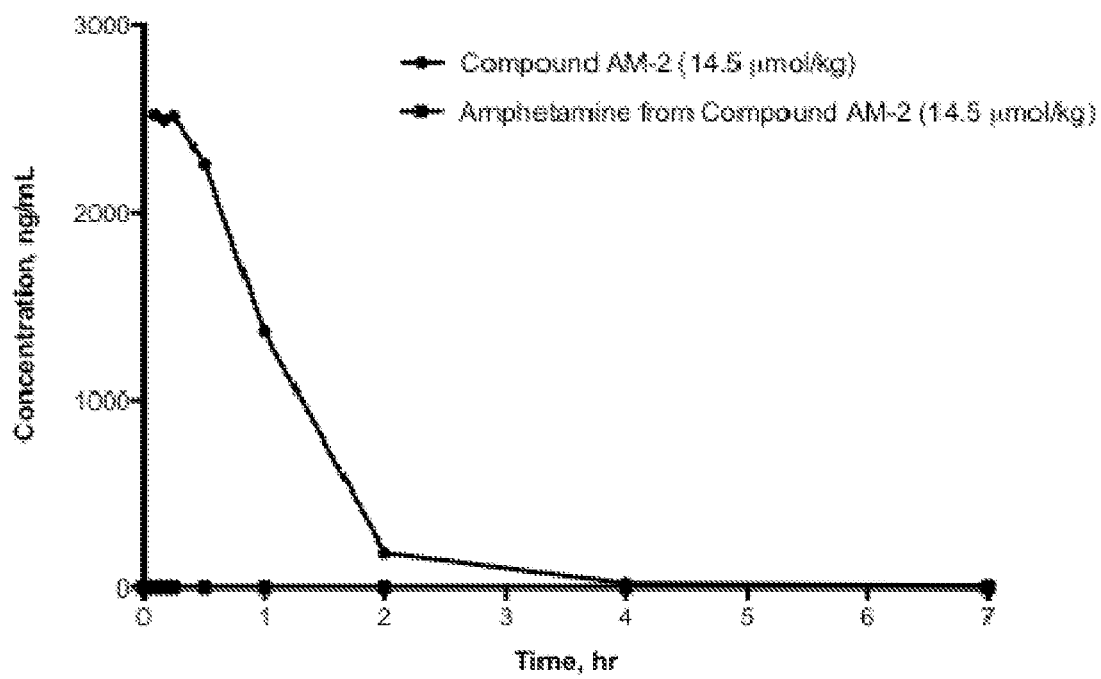
FIG. 9 shows a graph of mean plasma concentrations over time of Compound AM-2 and amphetamine following IV administration of Compound AM-2 to rats according to embodiments of the present disclosure.

Table 8 and FIG. 9 provide Compound AM-2 and amphetamine exposure results for the group of rats administered Compound AM-2 intravenously. Results in Table 8 are reported as maximum plasma concentration (Cmax) values (average±standard deviation) of Compound AM-2 and amphetamine, respectively.

TABLE 8

Cmax values of Compound AM-2 and amphetamine in rat plasma

| Compound | AM-2 Dose, mg/kg | AM-2 Dose, µmol/kg | AM-2 Cmax ± sd, ng/mL* | AMP Cmax ± sd, ng/mL^ |
|---|---|---|---|---|
| AM-2 | 6 | 14.5 | 2600 ± 260 | 1.41 ± 0.4 |

*Lower limit of quantitation was 0.100 ng/mL
^Lower limit of quantitation was 0.500 ng/mL FIG. 9 compares mean plasma concentrations over time of Compound AM-2 and amphetamine following IV administration of Compound AM-2 to rats.

Table 8 and FIG. 9 demonstrate that the plasma concentration of amphetamine in rats administered Compound AM-2 intravenously was only 0.05% of the plasma concentration of Compound AM-2, indicating that IV administration of Compound AM-2 did not lead to significant release of amphetamine.

Example 13

In Vivo Tolerability of Compound AM-2 in Rats

This Example demonstrates that Compound AM-2 was tolerated when administered intravenously to rats.

Male naïve Sprague-Dawley rats, 4 per dose, were used in the study. Rats were weighed, and then placed under a heat lamp for 15-20 minutes to dilate the lateral tail veins. Dose volumes are based on the body weights (1 mL/kg); dosing of Compound AM-2 (which can be prepared as described in Examples herein) was as indicated in Table 9. Before dosing, rats were placed in Broome restrainers and the drug was introduced into one of the tail veins using a syringe and needle. After dosing, the timer was set and rats were observed for clinical signs. Blood samples were collected 5 minutes post-dose via the saphenous vein. The rats were observed up to 24 hours. Results are shown in Table 9.

TABLE 9

In vivo tolerability of Compound AM-2 in rats

| Compound | Dose, mg/kg | Dose, µmol/kg | Number of Rats dosed | Clinical observations |
| --- | --- | --- | --- | --- |
| AM-2 | 64 | 155 | 4 | Appeared normal immediately post dose, followed by hyperactivity at 20 min. Recovered after 10 min. |

The results in Table 9 indicated that rats tolerated a dose of 155 µmol/kg of Compound AM-2 and recovered to normal activity within 30 minutes.

Example 14

Pharmacokinetics of Compound AM-3 Following PO Administration to Rats

This Example compares the oral (PO) pharmacokinetics (PK) of lisdexamphetamine to PO PK of Compound AM-1 and Compound AM-2, which are embodiments of compounds disclosed and claimed herein.

Saline solutions of Compound AM-3 (lisdexamphetamine) were dosed as indicated in Table 10 using methods as described in Examples 6 and 10 above. Samples were collected and stored as described in Examples 6 and 10 above.

Figure 10:
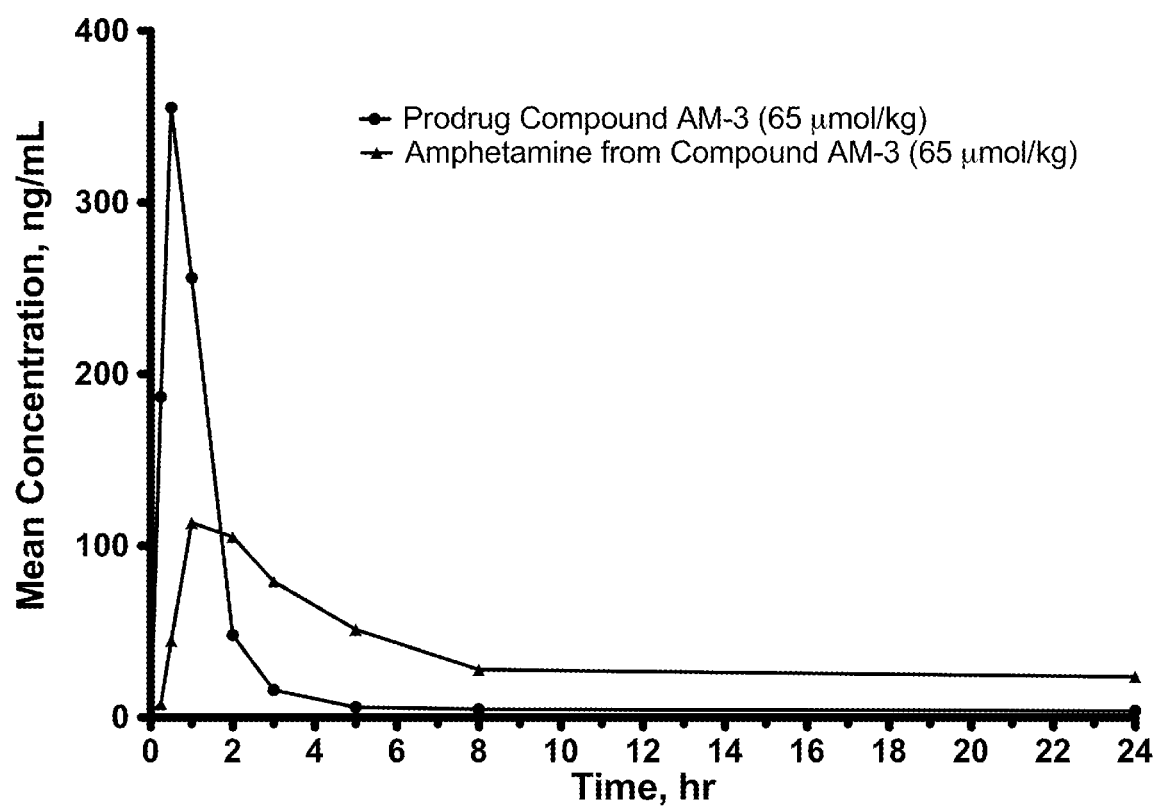
FIG. 10 shows a graph of mean plasma concentrations over time of prodrug disappearance and of amphetamine release following PO administration of Compound AM-3 according to embodiments of the present disclosure.

Table 10 and FIG. 10 provide prodrug and amphetamine exposure results for rats administered Compound AM-3. Results in Table 10 are reported, for each group of 4 rats, as (a) maximum plasma concentration (Cmax) of prodrug Compound AM-3 (average±standard deviation), (b) time after administration of Compound AM-3 to reach maximum prodrug Compound AM-3 concentration (Tmax) (average±standard deviation), (c) maximum plasma concentration (Cmax) of amphetamine (AMP) (average±standard deviation) and (d) time after administration of Compound AM-3 to reach maximum amphetamine concentration (Tmax) (average±standard deviation).

TABLE 10

Cmax and Tmax values of prodrug Compound AM-3 and amphetamine in rat plasma

| Compound | Dose, mg/kg | Dose, µmol/kg | Prodrug AM-3 Cmax ± sd, ng/mL | Prodrug AM-3 Tmax ± sd, hr | AMP Cmax ± sd, ng/mL | AMP Tmax ± sd, hr |
| --- | --- | --- | --- | --- | --- | --- |
| AM-3 | 22 | 65 | 357^ ± 133 | 0.625 ± 0.25 | 117 ± 45* | 1.25 ± 0.5 |

*Lower limit of quantitation was 0.0500 ng/mL
^Lower limit of quantitation was 0.500 ng/mL FIG. 10 compares mean plasma concentrations over time of prodrug disappearance and of amphetamine release following PO administration of Compound AM-3.

The results in Table 10 and FIG. 10 indicated that, when both compounds were administered orally at 65 mol/kg, the mean concentration of prodrug Compound AM-3 in plasma was significantly higher than that of Compound AM-1 (see Example 6).

Example 15

Pharmacokinetics of Compound AM-3 Following IV Administration to Rats

This Example compares the intravenous (IV) pharmacokinetics (PK) of lisdexamphetamine to IV PK of Compound AM-1 and Compound AM-2, which are embodiments of compounds disclosed and claimed herein.

Saline solutions of Compound AM-3 (lisdexamphetamine) were dosed as indicated in Table 11 using methods as described in Examples 8 and 12 above. Samples were collected and stored as described in Examples 8 and 12 above.

Figure 11:
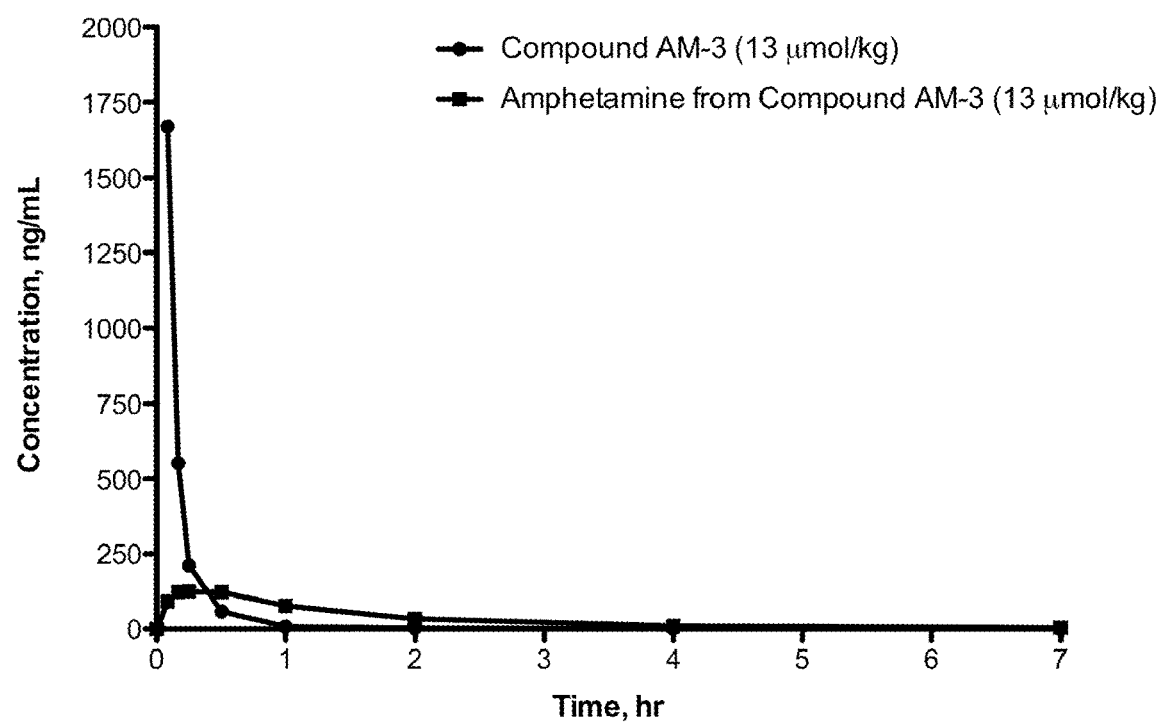
FIG. 11 shows a graph of mean plasma concentrations over time of Compound AM-3 and amphetamine following IV administration of Compound AM-3 to rats according to embodiments of the present disclosure.

Table 11 and FIG. 11 provide Compound AM-3 and amphetamine exposure results for the group of rats administered Compound AM-3 intravenously. Results in Table 11 are reported as maximum plasma concentration (Cmax) values (average±standard deviation) of Compound AM-1 and amphetamine, respectively.

TABLE 11

Cmax values of Compound AM-3 and amphetamine in rat plasma

| Compound | AM-3 Dose, mg/kg | AM-3 Dose, µmol/kg | AM-3 Cmax ± sd, ng/mL* | AMP Cmax ± sd, ng/mL^ |
| --- | --- | --- | --- | --- |
| AM-3 | 4.5 | 13 | 1670 ± 580 | 128 ± 4.3 |

*Lower limit of quantitation was 0.0500 ng/mL
^Lower limit of quantitation was 0.500 ng/mL FIG. 11 compares mean plasma concentrations over time of Compound AM-3 and amphetamine following IV administration of Compound AM-3 to rats.

Table 11 and FIG. 11 demonstrate that the plasma concentration of amphetamine in rats administered Compound AM-3 intravenously was 7.66% of the plasma concentration of Compound AM-3, indicating that IV administration of Compound AM-3 led to significantly more amphetamine release in the plasma than did IV administration of similar doses of compounds of the disclosure (see, for example, Examples 8 and 12).

Example 16

In Vivo Tolerability of Compound AM-3 in Rats

This Example compares the intravenous (IV) tolerability of lisdexamphetamine to the IV tolerability of Compound AM-1 and of Compound AM-2, which are embodiments of compounds disclosed and claimed herein.

The protocol to assess the IV tolerability of Compound AM-3 (lisdexamphetamine) was as described in Examples 9 and 13 above. Results are shown in Table 12.

TABLE 12

In vivo tolerability of Compound AM-3 in rats

| Compound | Dose, mg/kg | Dose, µmol/kg | Number of Rats dosed | Clinical observations |
|---|---|---|---|---|
| AM-3 | 64 | 190 | 1 | Died 10 sec post dose |
| AM-3 | 32 | 95 | 2 | Tremors, cyanotic up to 2 min, piloerection at 6 min; 2nd rat: tremors, apnea, died at 40 sec |
| AM-3 | 16 | 48 | 4 | intermittent tremors at 30 sec. hyperactive at 6 min, repetitive sniffing at 15-30 min, normal at 2 h |

The results in Table 12 indicated that rats tolerated a dose of 48 µmol/kg Compound AM-3 and recovered to normal activity by 2 hours. Higher doses of 95 µmol/kg and 190 µmol/kg Compound AM-3 caused death in 50% or 100%, respectively, of the rats within less than 1 min. In comparison, rats were more tolerant to compounds of the disclosure. For example, rats tolerated 87 µmol/kg of Compound AM-1 and recovered to normal activity within 2 minutes (see Example 9), and rats tolerated a dose of 155 µmol/kg of Compound AM-2 and recovered to normal activity within 30 minutes (see Example 13).

Example 17

Oral Administration of Compound AM-1 Co-Dosed with a Trypsin Inhibitor to Rats This Example demonstrates the ability of a trypsin inhibitor to affect the ability of an amphetamine prodrug of the embodiments to release amphetamine into plasma when such amphetamine prodrug was co-administered with increasing amounts of trypsin inhibitor orally to rats.

Saline solutions of prodrug Compound AM-1 (which can be prepared as described in the example herein) was co-dosed orally to rats with increasing concentrations of trypsin inhibitor Compound 109 (Catalog No. 3081, Tocris Bioscience, or Catalog No. WS38665, Waterstone Technology) as indicated in Table 13, using a method similar to that described in Example 6. Sampling and analysis procedures were also similar to those described in Example 6.

Figure 12:
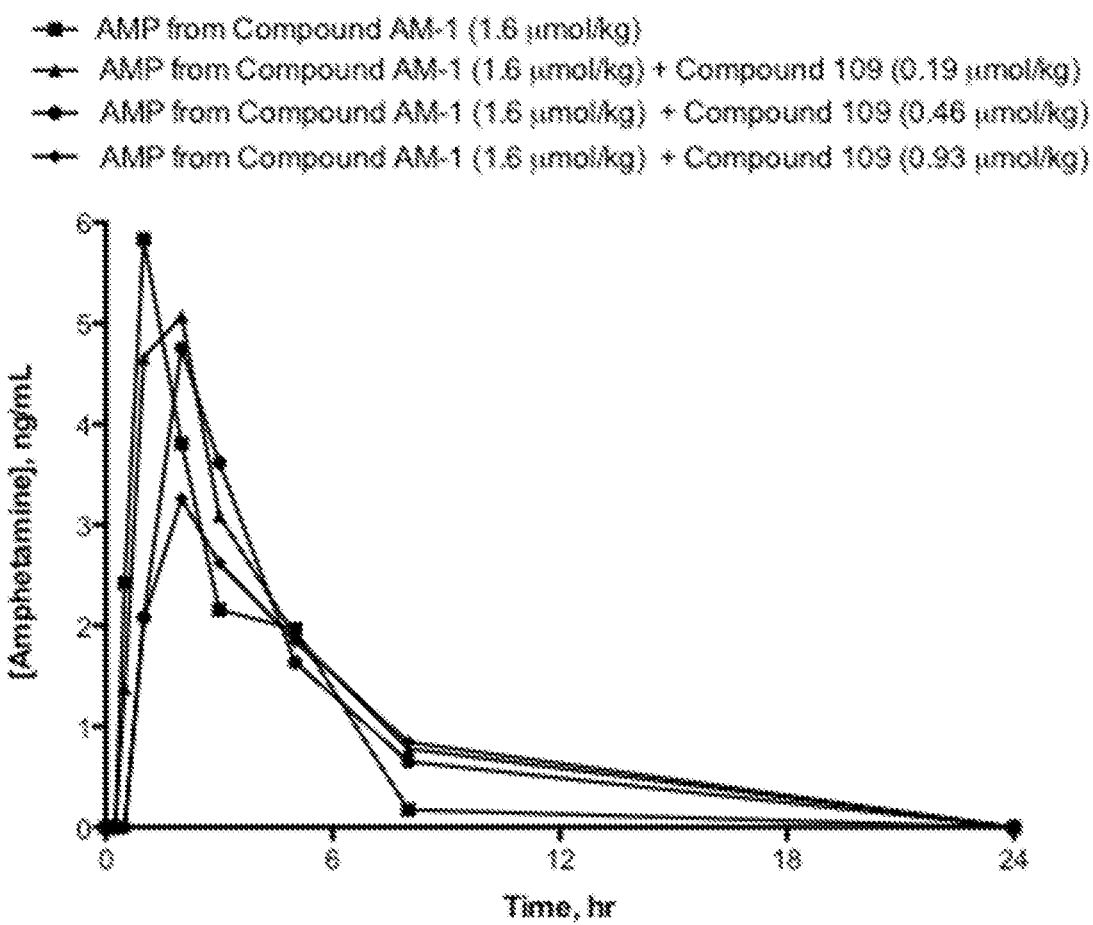
FIG. 12 provides a graph that compares mean plasma concentrations over time of amphetamine release following PO administration to rats of prodrug Compound AM-1 co-dosed with increasing amounts of trypsin inhibitor Compound 109.

Table 13 and FIG. 12 provide amphetamine exposure results for rats administered 0.6 mg/kg (1.6 µmol/kg) of Compound AM-1 co-dosed with increasing amounts of trypsin inhibitor Compound 109. Amphetamine Cmax and Tmax values in Table 13 are reported, for each group of four rats, as described in Example 6.

TABLE 13

Cmax and Tmax values of amphetamine in rat plasma

| AM-1 Dose, mg/kg | AM-1 Dose, µmol/kg | Compound 109 Dose, mg/kg | Compound 109 Dose, µmol/kg | AMP Cmax ± sd, ng/mL | Tmax ± sd, h |
|---|---|---|---|---|---|
| 0.6 | 1.6 | 0 | 0 | 5.83 ± 0.42 | 1.00 ± 0.0 |
| 0.6 | 1.6 | 0.1 | 0.19 | 5.46 ± 1.6 | 1.75 ± 0.50 |
| 0.6 | 1.6 | 0.25 | 0.46 | 4.75 ± 0.36 | 2.00 ± 0.0 |
| 0.6 | 1.6 | 0.5 | 0.93 | 3.26 ± 0.56 | 2.00 ± 0.0 |

Lower limit of quantitation was 0.500 ng/mL

FIG. 12 compares mean plasma concentrations over time of amphetamine release following PO administration of 0.6 mg/kg (1.6 µmol/kg) of prodrug Compound AM-1 with increasing amounts of co-dosed trypsin inhibitor Compound 109 to rats.

The results in Table 13 and FIG. 12 indicate Compound 109's ability to attenuate release of amphetamine by prodrugs of the embodiments, as indicated by suppressed Cmax and/or delayed Tmax values.

Example 18

Oral Administration of a Single Dose Unit and of Multiple Dose Units of a Composition Comprising Prodrug Compound AM-1 and Trypsin Inhibitor Compound 109 to Rats This Example demonstrates the effect of oral administration of single and multiple dose units comprising prodrug Compound AM-1 and trypsin inhibitor Compound 109 to rats.

Saline solutions of Compound AM-1 (which can be prepared as described in the examples herein) were dosed orally to rats (4 rats per group) at increasing concentrations ranging from 0.6 to 6 mg/kg (from 1.6 to 16 mol/kg), wherein a single dose was represented as 0.6 mg/kg (1.6 mol/kg) Compound AM-1 in the absence of trypsin inhibitor.

A second set of rats (4 rats per group) were co-dosed with prodrug Compound AM-1 and trypsin inhibitor Compound 109 (Catalog No. 3081, Tocris Bioscience, or Catalog No. WS38665, Waterstone Technology) as described below and indicated in Table 14. Specifically, a saline solution of a composition comprising 0.6 mg/kg (1.6 µmol/kg) Compound AM-1 and 0.1 mg/kg (0.2 mol/kg) Compound 109, representative of a single dose unit, was administered via oral gavage to each of 4 rats. It is to be noted that the mole-to-mole ratio of trypsin inhibitor-to-prodrug (109-to-AM-1) is 0.12-to-1 as such this dose unit is referred to herein as a 109-to-AM-1 (0.12-to-1) dose unit. Saline solutions representative of 2 dose units, 3 dose units, 4 dose units, 6 dose units, 8 dose units, and 10 dose units (i.e., as indicated in Table 14) of the 109-to-AM-1 (0.12-to-1) dose unit were similarly administered to additional groups of 4 rats.

All rats were jugular vein-cannulated male Sprague Dawley rats that had been fasted for 16-18 h prior to oral dosing. Dosing, sampling and analysis procedures were similar to those described in Example 6.

Figure 13A:
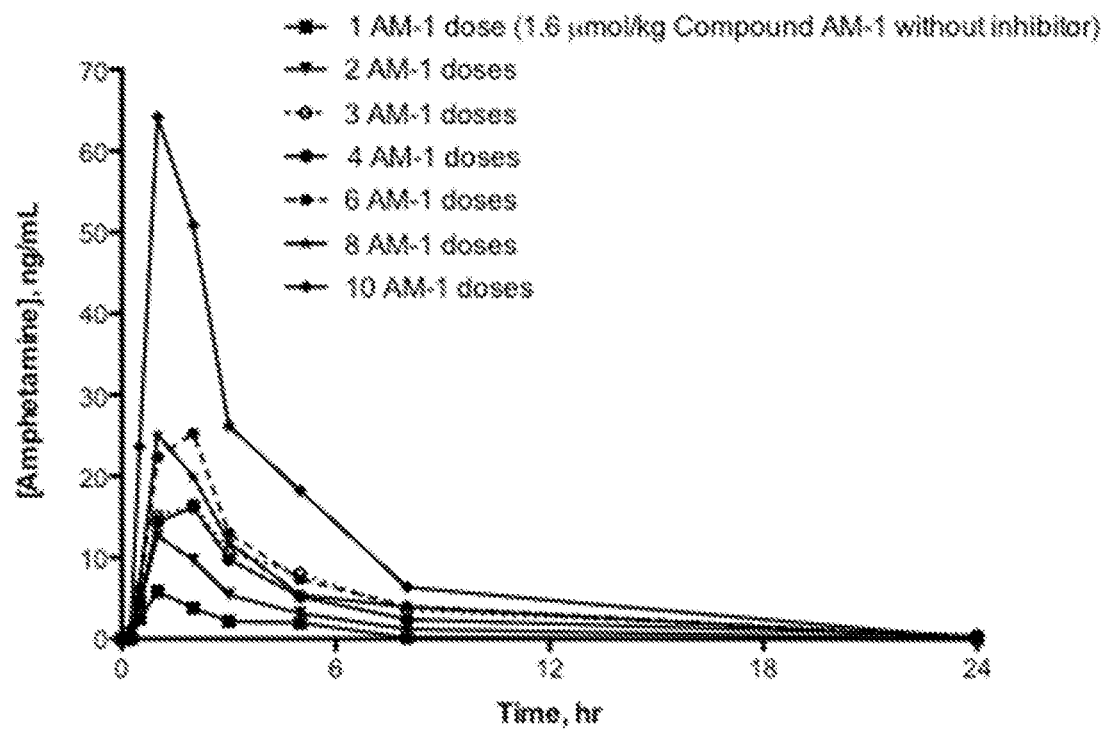
FIG. 13A provides a graph that compares mean plasma concentrations over time of amphetamine release following PO administration to rats of single and multiple doses of prodrug Compound AM-1 in the absence of trypsin inhibitor.
Figure 13B:
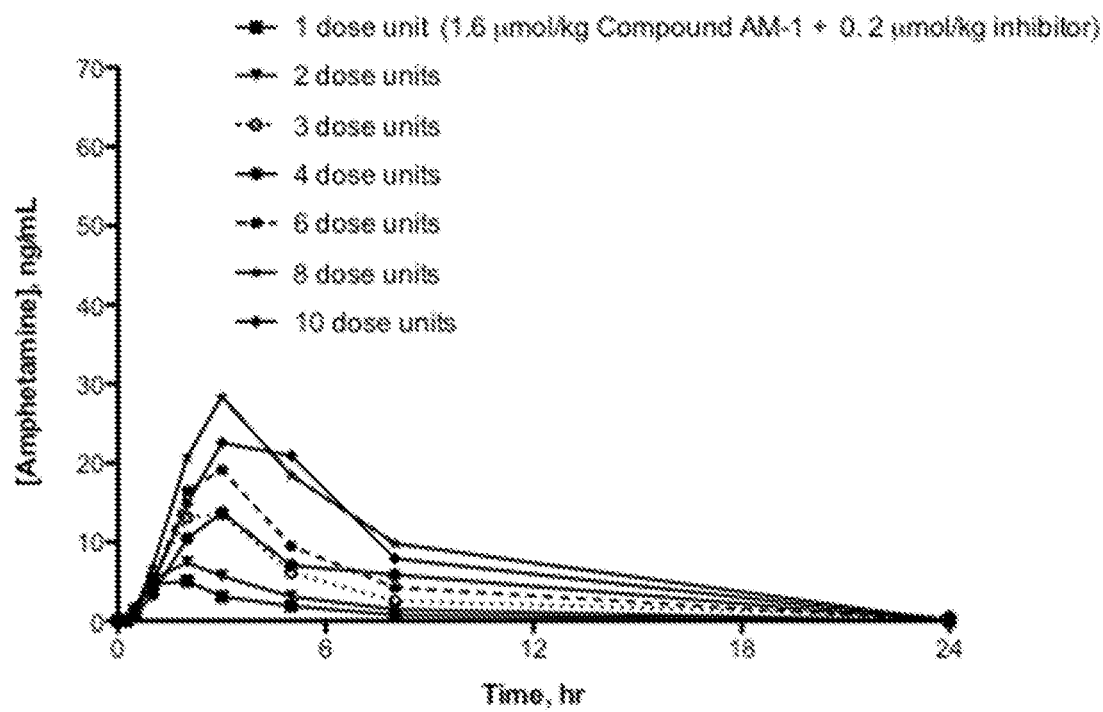
FIG. 13B provides a graph that compares mean plasma concentrations over time of amphetamine release following PO administration to rats of single and multiple dose units comprising prodrug Compound AM-1 and trypsin inhibitor Compound 109.

Table 14 (top half) and FIG. 13A provide amphetamine exposure results in plasma for rats administered 1, 2, 3, 4, 6, 8 and 10 doses of Compound AM-1 in the absence of trypsin inhibitor. Table 14 (bottom half) and FIG. 13B provide amphetamine exposure results in plasma for rats administered 1, 2, 3, 4, 6, 8 and 10 dose units of the 109-to-AM-1

(0.12-to-1) dose unit. Amphetamine Cmax and Tmax values are reported as described in Example 6.

TABLE 14

Cmax and Tmax values of amphetamine in rat plasma

| Amount (Multiple) | AM-1 Dose, mg/kg | AM-1 Dose, μmol/kg | 109 Dose, mg/kg | 109 Dose, μmol/kg | AMP Cmax ± sd, ng/mL | Tmax ± sd, h |
|---|---|---|---|---|---|---|
| 1 AM-1 dose | 0.6 | 1.6 | 0 | 0# | 5.83 ± 0.42 | 1.00 ± 0.00 |
| 2 AM-1 doses | 1.2 | 3.2 | 0 | 0* | 13.2 ± 3.3 | 1.25 ± 0.50 |
| 3 AM-1 doses | 1.8 | 4.9 | 0 | 0* | 17.2 ± 3.9 | 1.50 ± 0.58 |
| 4 AM-1 doses | 2.4 | 6.5 | 0 | 0* | 17.6 ± 4.1 | 1.50 ± 0.58 |
| 6 AM-1 doses | 3.6 | 9.7 | 0 | 0* | 26.0 ± 5.5 | 1.75 ± 0.50 |
| 8 AM-1 doses | 4.8 | 13 | 0 | 0* | 25.2 ± 2.3 | 1.00 ± 0.00 |
| 10 AM-1 doses | 6 | 16 | 0 | 0^ | 64.2 ± 10 | 1.00 ± 0.00 |
| 1 dose unit | 0.6 | 1.6 | 0.1 | 0.2# | 5.46 ± 1.6 | 1.75 ± 0.50 |
| 2 dose units | 1.2 | 3.2 | 0.2 | 0.4* | 7.45 ± 1.4 | 2.25 ± 0.50 |
| 3 dose units | 1.8 | 4.9 | 0.3 | 0.6* | 15.4 ± 2.1 | 2.50 ± 0.58 |
| 4 dose units | 2.4 | 6.5 | 0.4 | 0.7* | 13.7 ± 3.3 | 3.00 ± 0.00 |
| 6 dose units | 3.6 | 9.7 | 0.6 | 1.1* | 20.0 ± 6.7 | 2.75 ± 0.50 |
| 8 dose units | 4.8 | 13 | 0.8 | 1.5* | 28.8 ± 6.4 | 2.75 ± 0.50 |
| 10 dose units | 6 | 16 | 1 | 1.9# | 24.3 ± 9.3 | 4.00 ± 1.2 |

*Lower limit of quantitation was 0.100 ng/mL
^Lower limit of quantitation was 1.00 ng/mL
Lower limit of quantitation was 0.500 ng/mL FIG. 13A compares mean plasma concentrations over time of amphetamine release following PO administration to rats of a single dose and of multiple doses of Compound AM-1 dosed in the absence of trypsin inhibitor.

FIG. 13B compares mean plasma concentrations over time of amphetamine release following PO administration to rats of a single dose unit and of multiple dose units of a composition comprising prodrug Compound AM-1 and trypsin inhibitor Compound 109.

The results in Table 14, FIG. 13A and FIG. 13B indicate that administration of multiple dose units (as exemplified by 1, 2, 3, 4, 6, 8 and 10 dose units of the 109-to-AM-1 (0.12-to-1) dose unit) results in a plasma amphetamine concentration-time PK profile that is not dose proportional to the plasma amphetamine concentration-time PK profile of the single dose unit. In addition, the PK profile of the multiple dose units was modified compared to the PK profile of the equivalent dosage of prodrug in the absence of trypsin inhibitor.

Example 19

Pharmacokinetics of Compound AM-5 Following PO Administration to Rats

This Example indicates the release of amphetamine into plasma when an amphetamine prodrug of the embodiments was administered orally (PO) to rats.

Compound AM-5 (which can be prepared as described herein) was dissolved in water and administered to rats as indicated in Table 15 using methods as described in Example 6. Samples were collected and stored as described in Example 6.

Figure 14:
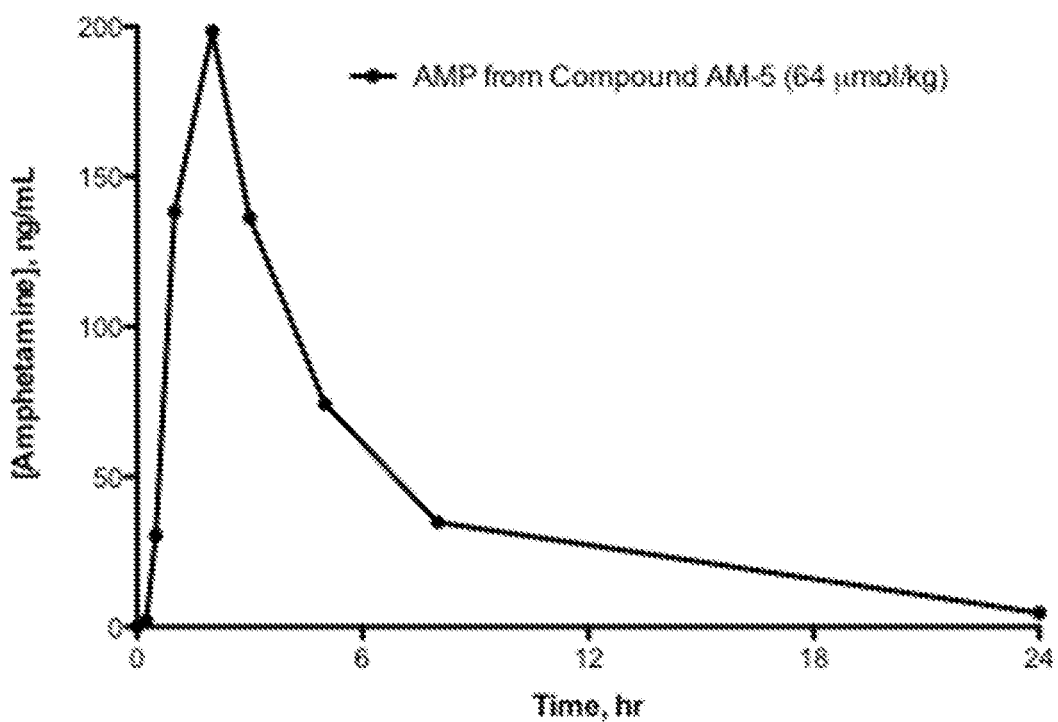
FIG. 14 provides a graph of mean plasma concentrations over time of amphetamine release following PO administration to rats of prodrug Compound AM-5.

Table 15 and FIG. 14 provide amphetamine exposure results for rats administered Compound AM-5. Amphetamine Cmax, and Tmax values in Table 15 are reported for the group of four rats as described in Example 6.

TABLE 15

Cmax and Tmax values amphetamine in rat plasma

| Compound | Dose, mg/kg | Dose μmol/kg | AMP Cmax ± sd, ng/mL | AMP Tmax ± sd, hr |
|---|---|---|---|---|
| AM-5 | 22 | 64 | 198^ ± 78 | 2.00 ± 0.0 |

^Lower limit of quantitation was 1.00 ng/mL

FIG. 14 demonstrates the mean plasma concentration over time of amphetamine release following PO administration to rats of Compound AM-5.

The results in Table 15 and FIG. 14 indicate that oral administration of Compound AM-5 leads to release of amphetamine by an amphetamine prodrug of the embodiments.

Example 20

Pharmacokinetics of Compound AM-4 Following PO Administration to Rats

This Example indicates the release of amphetamine into plasma when Compound AM-4 was administered orally (PO) to rats.

Compound AM-4 (which can be prepared as described herein) was dissolved in water and administered to rats as indicated in Table 16 using methods as described in Example 6. Samples were collected and stored as described in Example 6.

Figure 15:
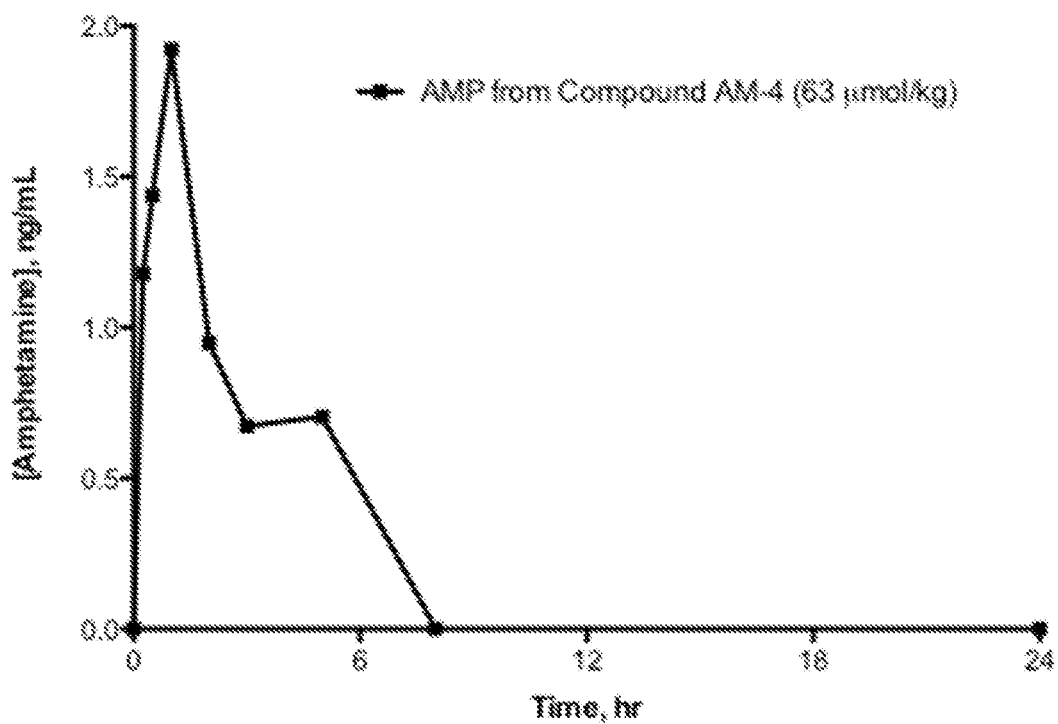
FIG. 15 provides a graph of mean plasma concentrations over time of amphetamine release following PO administration to rats of Compound AM-4.

Table 16 and FIG. 15 provide amphetamine exposure results for rats administered Compound AM-4. Amphetamine Cmax, and Tmax values in Table 16 are reported for the group of four rats as described in Example 6.

TABLE 16

Cmax and Tmax values of amphetamine in rat plasma

| Compound | Dose, mg/kg | Dose μmol/kg | AMP Cmax ± sd, ng/mL | AMP Tmax ± sd, hr |
|---|---|---|---|---|
| AM-4 | 24 | 63 | 1.92 ± 0.20* | 1.00 ± 0.0 |

*Lower limit of quantitation was 0.0500 ng/mL

FIG. 15 demonstrates the mean plasma concentration over time of amphetamine release following PO administration to rats of Compound AM-4.

The results in Table 16 and FIG. 15 indicate that oral administration of Compound AM-4 leads to only minimal release of amphetamine compared to the release of amphetamine upon oral administration of amphetamine prodrugs of the embodiments.

Example 21

Pharmacokinetics of Compound AM-5 Following IV Administration to Rats

This Example compares the plasma concentrations of prodrug and amphetamine in rats following intravenous (IV) administration of an amphetamine prodrug of the embodiments.

Compound AM-5 (which can be prepared as described in the examples herein) was dissolved in water and injected into the tail vein of 4 jugular vein-cannulated male Sprague Dawley rats at a dose of 4.5 mg/kg. At specified time points, blood samples were collected, treated, and analyzed in a manner similar to that described in Example 8.

Figure 16:
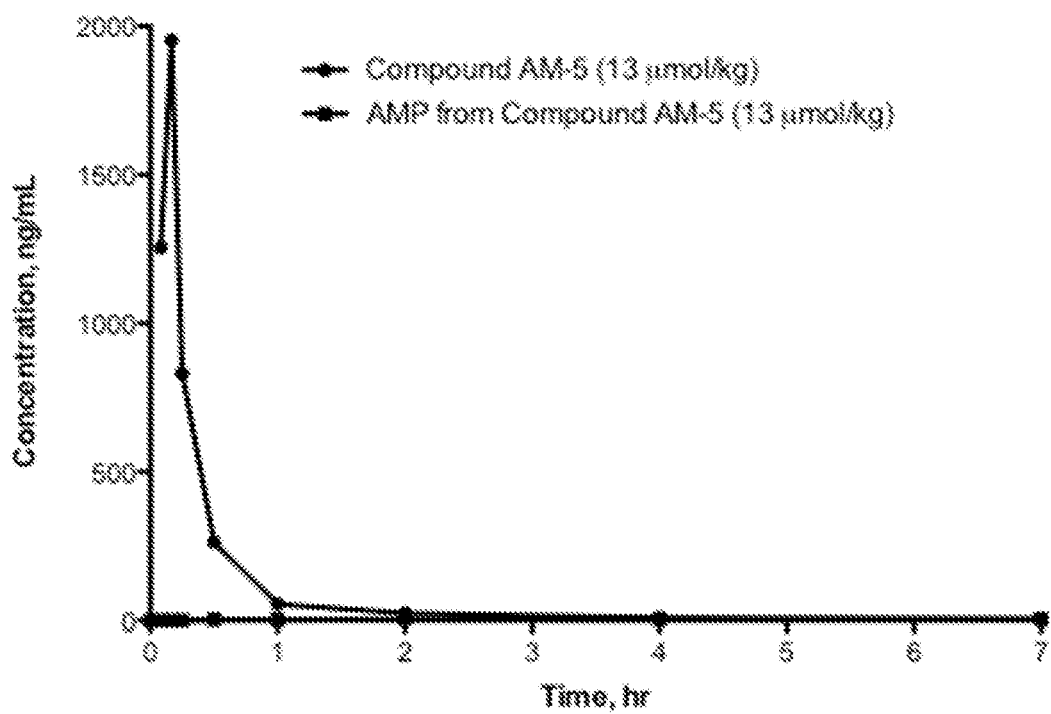
FIG. 16 provides a graph of mean plasma concentrations over time of prodrug Compound AM-5 and amphetamine following IV administration to rats of prodrug Compound AM-5.

Table 17 and FIG. 16 provide Compound AM-5 and amphetamine exposure results for the group of rats administered Compound AM-5 intravenously. Results in Table 17 are reported as maximum plasma concentration (Cmax) values (average±standard deviation) of Compound AM-5 and amphetamine, respectively.

TABLE 17

Cmax values of Compound AM-5 and amphetamine in rat plasma

| Compound | AM-5 Dose, mg/kg | AM-5 Dose, μmol/kg | AM-5 Cmax ± sd, ng/mL^ | AMP Cmax ± sd, ng/mL* |
|---|---|---|---|---|
| AM-5 | 4.5 | 13 | 2150 ± 1700 | 6.83 ± 2.0 |

*Lower limit of quantitation was 1.00 ng/mL
^Lower limit of quantitation was 0.0500 ng/mL FIG. 16 compares mean plasma concentrations over time of Compound AM-5 and amphetamine following IV administration of Compound AM-5 to rats.

Table 17 and FIG. 16 demonstrate that the plasma concentration of amphetamine in rats administered Compound AM-5 intravenously is only 0.32% of the plasma concentration of Compound AM-5, indicating that IV administration of Compound AM-5, an amphetamine prodrug of the embodiments, does not lead to significant release of amphetamine.

Example 22

Pharmacokinetics of Compounds AM-4 and Compound AM-6 Following IV Administration to Rats This Example demonstrates the plasma concentration of amphetamine in rats following intravenous (IV) administration of Compound AM-4 or Compound AM-6.

Compound AM-4 and Compound AM-6 (each of which can be prepared as described in the examples herein) were each dissolved in saline and injected into the tail vein of a group of 4 jugular vein-cannulated male Sprague Dawley rats at the respective doses indicated in Table 18. At specified time points, blood samples were collected, treated, and analyzed in a manner similar to that described in Example 8.

Table 18 provides amphetamine exposure results for the group of rats administered Compound AM-4 and Compound AM-6 intravenously. Results in Table 18 are reported as maximum plasma concentration (Cmax) values (average±standard deviation) of amphetamine.

TABLE 18

Cmax values of amphetamine in rat plasma

| Compound | AM-6 Dose, mg/kg | AM-6 Dose, μmol/kg | AMP Cmax ± sd, ng/mL* |
|---|---|---|---|
| AM-4 | 4.5 | 12 | 17.9 ± 3.5 |
| AM-6 | 4.8 | 13 | 134 ± 36 |

*Lower limit of quantitation was 1.00 ng/mL

Table 18 demonstrates the release of amphetamine into the plasma of rats administered Compound AM-4 or Compound AM-6 intravenously.

Synthesis of Small Molecule Trypsin Inhibitors

Example 23

Synthesis of (S)-ethyl 4-(5-guanidino-2-(naphthalene-2-sulfonamido)pentanoyl)piperazine-1-carboxylate (Compound 101)

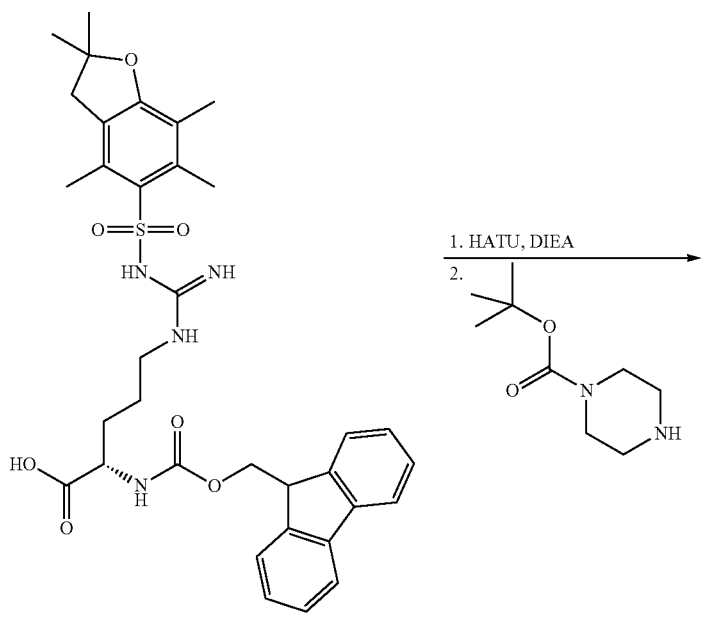

-continued
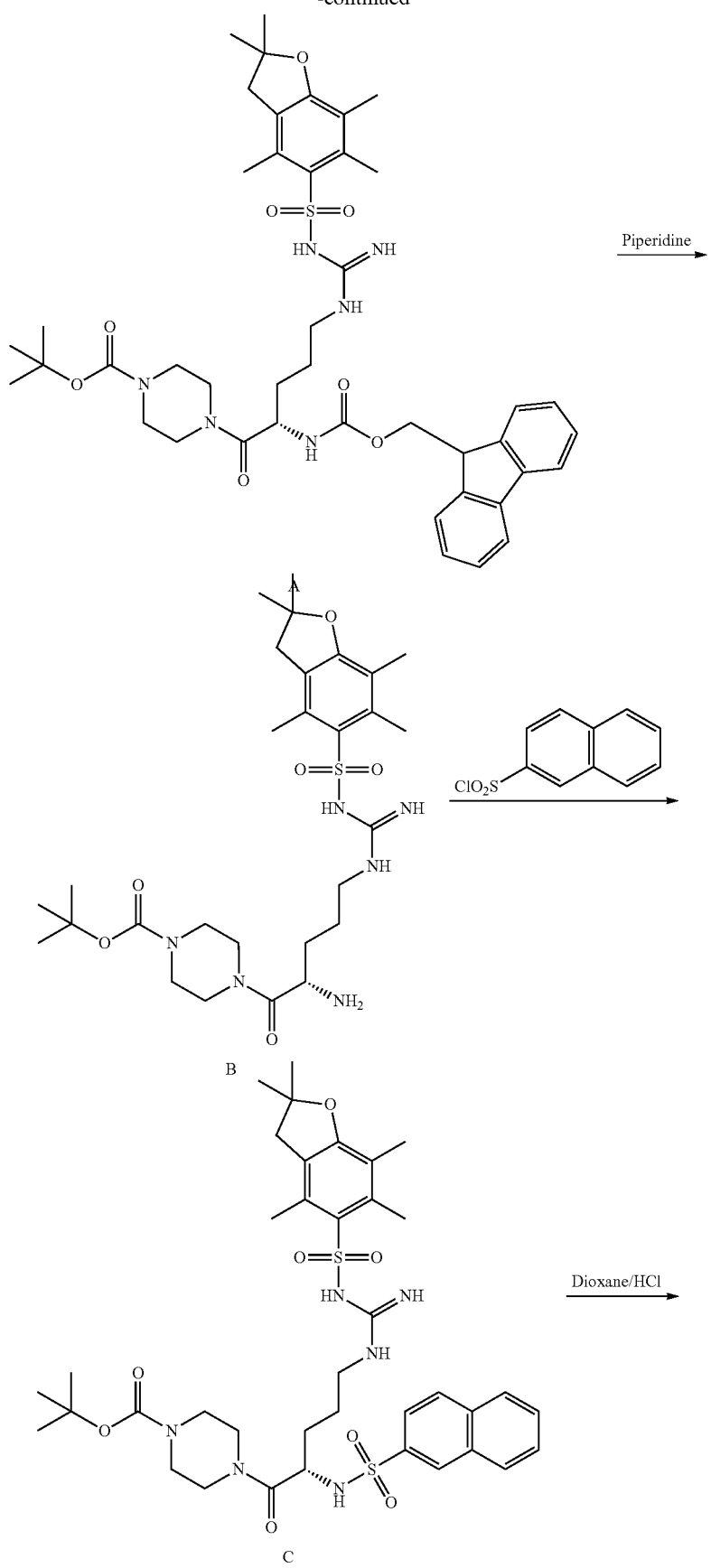

-continued
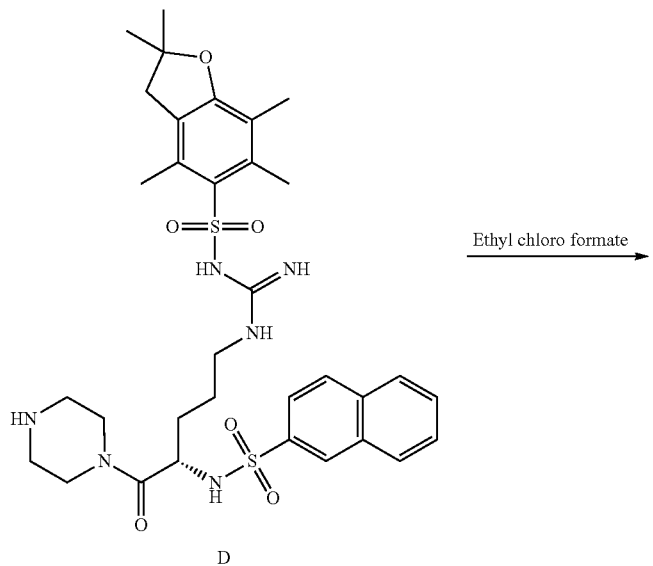
D
Ethyl chloro formate →
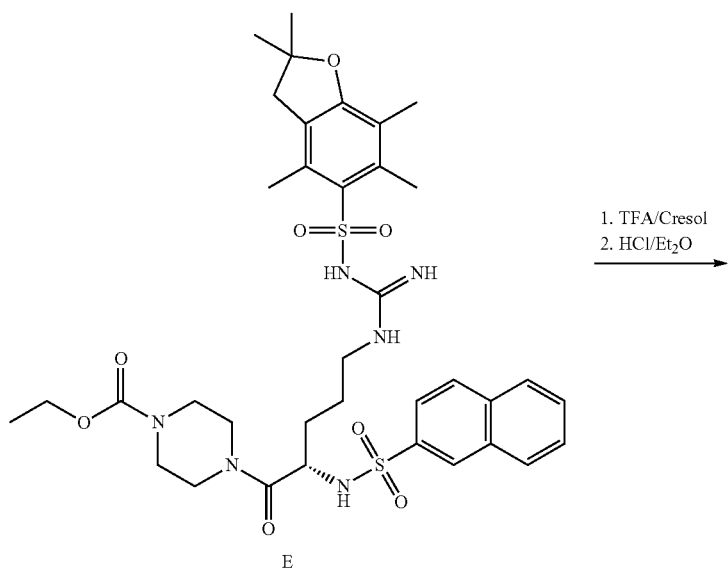
E
1. TFA/Cresol
2. HCl/Et₂O →
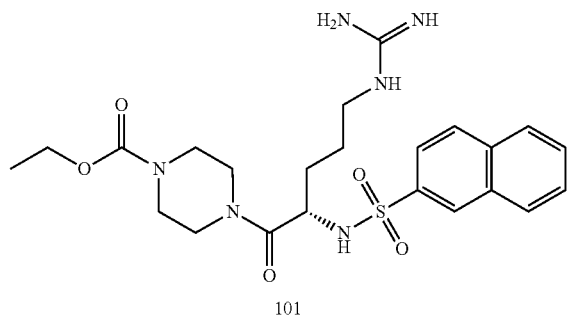
101

Synthesis of 4-[(S)-5-([Amino-[(E)-2,2,4,6,7-pentamethyl-2,3-dihydro-benzofuran-5-sulfonylimino]-methyl]-amino)-2-(9H-fluoren-9-ylmethoxycarbonylamino)-pentanoyl]-piperazine-1-carboxylic acid tert-butyl ester (A)

To a solution of Fmoc-Arg(Pbf)-OH 1 (25.0 g, 38.5 mmol) in DMF (200 mL) at room temperature was added DIEA (13.41 mL, 77.1 mmol). After stirring at room temperature for 10 min, the reaction mixture was cooled to ~5° C. To the reaction mixture was added HATU (16.11 g, 42.4 mmol) in portions and stirred for 20 min and a solution of tert-butyl-1-piperazine carboxylate (7.18 g, 38.5 mmol) in DMF (50 mL) was added dropwise. The reaction mixture was stirred at ~5° C. for 5 min. The mixture reaction was then allowed to warm to room temperature and stirred for 2 h. Solvent was removed in vacuo and the residue was dissolved in EtOAc (500 mL), washed with water (2×750 mL), 1% $H_2SO_4$ (300 mL) and brine (750 mL). The organic layer was separated, dried over $Na_2SO_4$ and solvent removed in vacuo to a total volume of 100 mL Compound A was taken to the next step as EtOAc solution (100 mL). LC-MS [M+H] 817.5 ($C_{43}H_{56}N_6O_8S$+H, calc: 817.4).

Synthesis of 4-[(S)-2-Amino-5-({amino-[(E)-2,2,4,6,7-pentamethyl-2,3-dihydro-benzofuran-5-sulfonylimino]-methyl}-amino)-pentanoyl]-piperazine-1-carboxylic acid tert-butyl ester (B)

To a solution of compound A (46.2 mmol) in EtOAc (175 mL) at room temperature was added piperidine (4.57 mL, 46.2 mmol) and the reaction mixture was stirred for 18 h at room temperature. Next the solvent was removed in vacuo and the resulting residue dissolved in minimum amount of EtOAc (~50 mL) and hexane (~1 L) was added. The precipitated crude product was filtered off and recrystallised again with EtOAc (~30 mL) and hexane (~750 mL). The precipitate was filtered off, washed with hexane and dried in vacuo to afford compound B (28.0 g, 46.2 mmol). LC-MS [M+H] 595.4 ($C_{28}H_{46}N_6O_6S$+H, calc: 595.3). Compound B was used without further purification.

Synthesis of 4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazine-1-carboxylic acid tert-butyl ester (C)

To a solution of compound B (28.0 g, 46.2 mmol) in THF (250 mL) was added aqueous 1N NaOH (171 mL). The reaction mixture was cooled to ~5° C., a solution of 2-naphthalene sulfonylchloride (26.19 g, 115.6 mmol) in THF (125 mL) was added dropwise. The reaction mixture was stirred at ~5° C. for 10 min, with stirring continued at room temperature for 2 h. The reaction mixture was diluted with EtOAc (1 L), washed with aqueous 1N NaOH (1 L), water (1 L) and brine (1 L). The organic layer was separated, dried over $Na_2SO_4$ and removal of the solvent in vacuo to afford compound C (36.6 g, 46.2 mmol). LC-MS [M+H] 785.5 ($C_{38}H_{52}N_6O_8S_2$+H, calc: 785.9). Compound C was used without further purification.

Synthesis of 2,2,4,6,7-Pentamethyl-2,3-dihydro-benzofuran-5-sulfonic acid 1-amino-1-[(S)-4-(naphthalene-2-sulfonylamino)-5-oxo-5-piperazin-1-yl-pentylamino]-meth-(E)-ylideneamide (D)

To a solution of compound C (36.6 g, 46.2 mmol) in dioxane (60 mL) was added 4M HCl in dioxane (58 mL) dropwise. The reaction mixture was stirred at room temperature for 1.5 h. $Et_2O$ (600 mL) was added to the reaction mixture, the precipitated product was filtered off, washed with $Et_2O$ and finally dried in vacuo to afford compound D (34.5 g, 46.2 mmol). LC-MS [M+H] 685.4 ($C_{33}H_{44}N_6O_6S_2$+H, calc: 685.9). Compound D was used without further purification.

Synthesis of 4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazine-1-carboxylic acid ethyl ester (E)

To a solution of compound D (8.0 g, 11.1 mmol) in $CHCl_3$ (50 mL) was added DIEA (4.1 mL, 23.3 mmol) at room temperature and stirred for 15 min. The mixture was cooled to ~5° C., ethyl chloroformate (1.06 mL, 11.1 mmol) was added dropwise. After stirring at room temperature overnight (~18 h), solvent removed in vacuo. The residue was dissolved in MeOH (~25 mL) and $Et_2O$ (~500 mL) was added. The precipitated crude product was filtered off, washed with $Et_2O$ and dried in vacuo to afford compound E (8.5 g, 11.1 mmol). LC-MS [M+H] 757.6 ($C_{36}H_{48}N_6O_8S_2$+H, calc: 757.9). Compound E was used without further purification.

Synthesis of (S)-ethyl 4-(5-guanidino-2-(naphthalene-2-sulfonamido)pentanoyl)piperazine-1-carboxylate (Compound 101)

A solution of 5% m-cresol/TFA (50 mL) was added to compound E (8.5 g, 11.1 mmol) at room temperature. After stirring for 1 h, the reaction mixture was precipitated with $Et_2O$ (~500 mL). The precipitate was filtered and washed with $Et_2O$ and dried in vacuo to afford the crude product. The crude product was purified by preparative reverse phase HPLC. [Column: VARIAN, LOAD & LOCK, L&L 4002-2, Packing: Microsorb 100-10 C18, Injection, Volume: ~15 mL×2, Injection flow rate: 20 mL/min, 100% A, (water/0.1% TFA), Flow rate: 100 mL/min, Fraction: 30 Sec (50 mL), Method: 0% B (MeCN/0.1% TFA)-60% B/60 min/100 mL/min/254 nm]. Solvents were removed from pure fractions in vacuo. Trace of water was removed by co-evaporation with 2× i-PrOH (50 mL). The residue was dissolved in a minimum amount of i-PrOH and product was precipitated with 2 M HCl in $Et_2O$. Product was filtered off and washed with $Et_2O$ and dried in vacuo to afford Compound 101 as HCl salt 7 (3.78 g, 63% yield, 99.4% purity). LC-MS [M+H] 505.4 ($C_{38}H_{52}N_6O_8S_2$+H, calc: 505.6).

Example 24
Synthesis of (S)-ethyl 4-(5-guanidino-2-(2,4,6-tri-isopropylphenylsulfonamido)pentanoyl)piperazine-1-carboxylate (Compound 102)
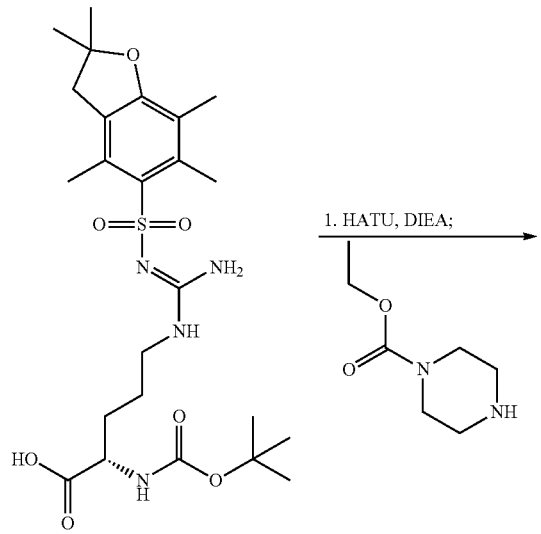
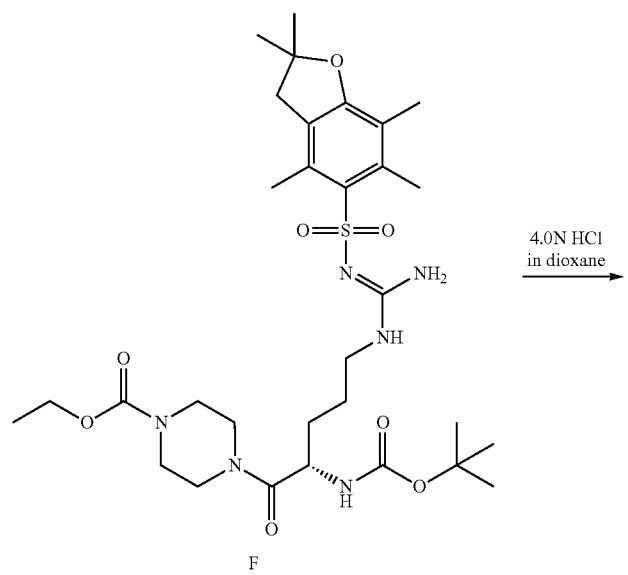

-continued
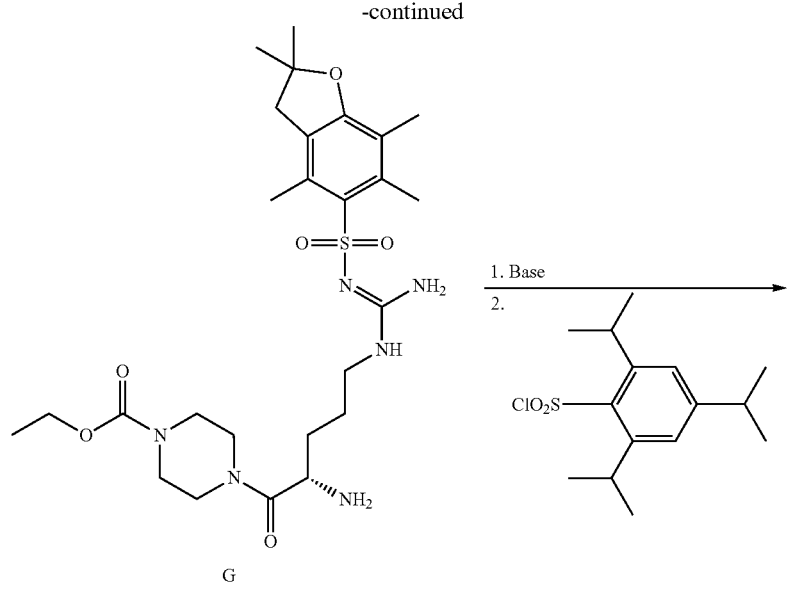
G
1. Base
2.
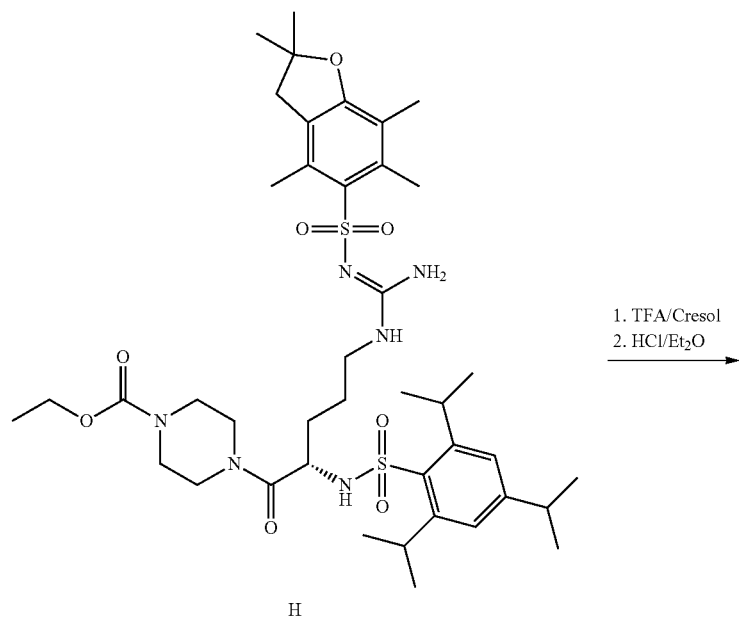
H
1. TFA/Cresol
2. HCl/Et₂O
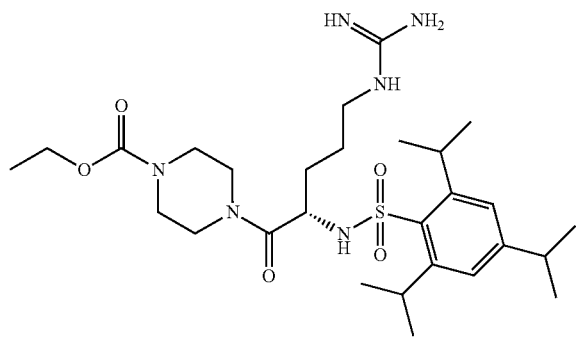
102

Synthesis of 4-[(S)-5-({Amino-[(E)-2,2,4,6,7-pentamethyl-2,3-dihydro-benzofuran-5-sulfonylimino]-methyl}-amino)-2-tert-butoxycarbonylamino-pentanoyl]-piperazine-1-carboxylic acid ethyl ester (F)

To a solution of Boc-Arg(Pbf)-OH (13.3 g, 25.3 mmol) in DMF (10 mL) was added DIEA (22.0 mL, 126.5 mmol) at room temperature and stirred for 15 min. The reaction mixture was then cooled to ~5° C. and HATU (11.5 g, 30.3 mmol) was added in portions and stirred for 30 min, followed by the dropwise addition of ethyl-1-piperazine carboxylate (4.0 g, 25.3 mmol) in DMF (30 mL). After 40 min, the reaction mixture was diluted with EtOAc (400 mL) and poured into $H_2O$ (1 L). Extracted with EtOAc (2×400 mL) and washed with $H_2O$ (800 mL), 2% $H_2SO_4$ (500 mL), $H_2O$ (2×800 mL) and brine (800 mL). Organic layer was separated, dried over $MgSO_4$ and solvent removed in vacuo. The resultant oily residue was dried in vacuo to afford compound F (16.4 g, 24.5 mmol) as foamy solid. LC-MS [M+H] 667.2 ($C_{31}H_{50}N_6O_8S$+H, calc: 667.8). Compound F was used without further purification.

Synthesis of 4-[(S)-2-Amino-5-({amino-[(E)-2,2,4,6,7-pentamethyl-2,3-dihydro-benzofuran-5 sulfonylimino]-methyl}-amino)-pentanoyl]-piperazine-1-carboxylic acid ethyl ester (G)

A solution of compound F (20.2 g, 30.2 mmol) in dichloromethane (90 mL) was treated with 4.0 N HCl in 1,4-dioxane (90 mL, 363.3 mmol) and stirred at room temperature for 2 h. Next most of the dichloromethane (~90%) was removed in vacuo and $Et_2O$ (~1 L) was added. The resultant precipitate was filtered off and washed with $Et_2O$ and dried in vacuo to afford compound G (17.8 g, 30.2 mmol). LC-MS [M+H] 567.8 ($C_{26}H_{42}N_6O_6S$+H, calc: 567.8). Compound G was used without further purification.

Synthesis of 4-[(S)-5-({Amino-[(E)-2,2,4,6,7-pentamethyl-2,3-dihydro-benzofuran-5-sulfonylimino]-methyl}-amino)-2-(2,4,6-triisopropyl-benzenesulfonylamino)-pentanoyl]-piperazine-1-carboxylic acid ethyl ester (H)

To a solution of compound G (1.0 g, 1.8 mmol) in THF (7 mL) was added 3.1N aqueous NaOH (4.0 mL) and stirred for 5 min. The reaction mixture was cooled to ~5° C., and then a solution of tripsyl chloride added dropwise (2.2 g, 7.3 mmol) in THF (5 mL) and stirred at room temperature overnight (~18 h). The reaction mixture was diluted with $H_2O$ (130 mL), acidified with 2% $H_2SO_4$ (15 mL) and extracted with EtOAc (3×80 mL). Organic layer were combined and washed with $H_2O$ (2×400 mL), saturated $NaHCO_3$ (100 mL), $H_2O$ (200 mL) and brine (200 mL) The organic layer was separated, dried over $MgSO_4$ and solvent removed in vacuo to afford (2.9 g) of crude product. This was purified by normal phase flash chromatography (5-10% MeOH/DCM) to afford compound H (0.52 g, 1.0 mmol). LC-MS [M+H] 833.8 ($C_{41}H_{64}N_6O_8S_2$+H, calc: 834.1).

Synthesis of (S)-ethyl 4-(5-guanidino-2-(2,4,6-triisopropylphenylsulfonamido)pentanoyl)piperazine-1-carboxylate (Compound 102)

A solution of 5% m-cresol/TFA (40 mL) was added to compound H (3.73 g, 3.32 mmol) at room temperature. After stirring for 45 min, solvents were removed in vacuo. Residue was dissolved in dichloromethane (100 mL), washed with $H_2O$ (3×200 mL) and brine (200 mL). The organic layer was separated, dried over $MgSO_4$ and then the solvent removed in vacuo. The residue was dissolved in dichloromethane (~5 mL) and then hexane (~250 mL) was added and a precipitate was formed. This was washed with hexane and dried in vacuo to afford the crude product (1.95 g). The crude product was purified by reverse phase HPLC [Column: VARIAN, LOAD & LOCK, L&L 4002-2, Packing: Microsorb 100-10 C18, Injection Volume: ~15 mL, Injection flow rate: 20 mL/min, 100% A, (water/0.1% TFA), Flow rate: 100 mL/min, Fraction: 30 Sec (50 mL), Method: 25% B (MeCN/0.1% TFA)/70% B/98 min/100 mL/min/254 nm]. Solvents were removed from pure fractions in vacuo. Trace of water was removed by co-evaporation with 2× i-PrOH (50 mL). The residue was dissolved in a minimum amount of i-PrOH and product was precipitated with 2 M HCl in $Et_2O$. Product was filtered off and washed with $Et_2O$ and dried in vacuo to afford the product as HCl salt of Compound 102 (0.72 g, 35% yield, 99.8% purity). LC-MS [M+H] 581.6 ($C_{28}H_{48}N_6O_5S$+H, calc: 581.7).

Example 25

Synthesis of (S)-ethyl 1-(5-guanidino-2-(naphthalene-2-sulfonamido)pentanoyl)piperidine-4-carboxylate HCl salt (Compound 103)

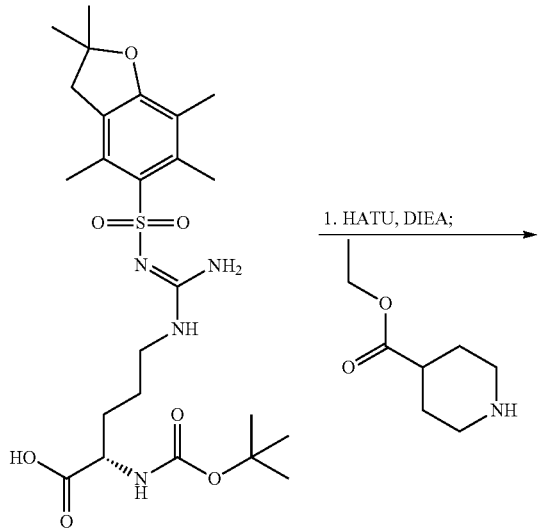

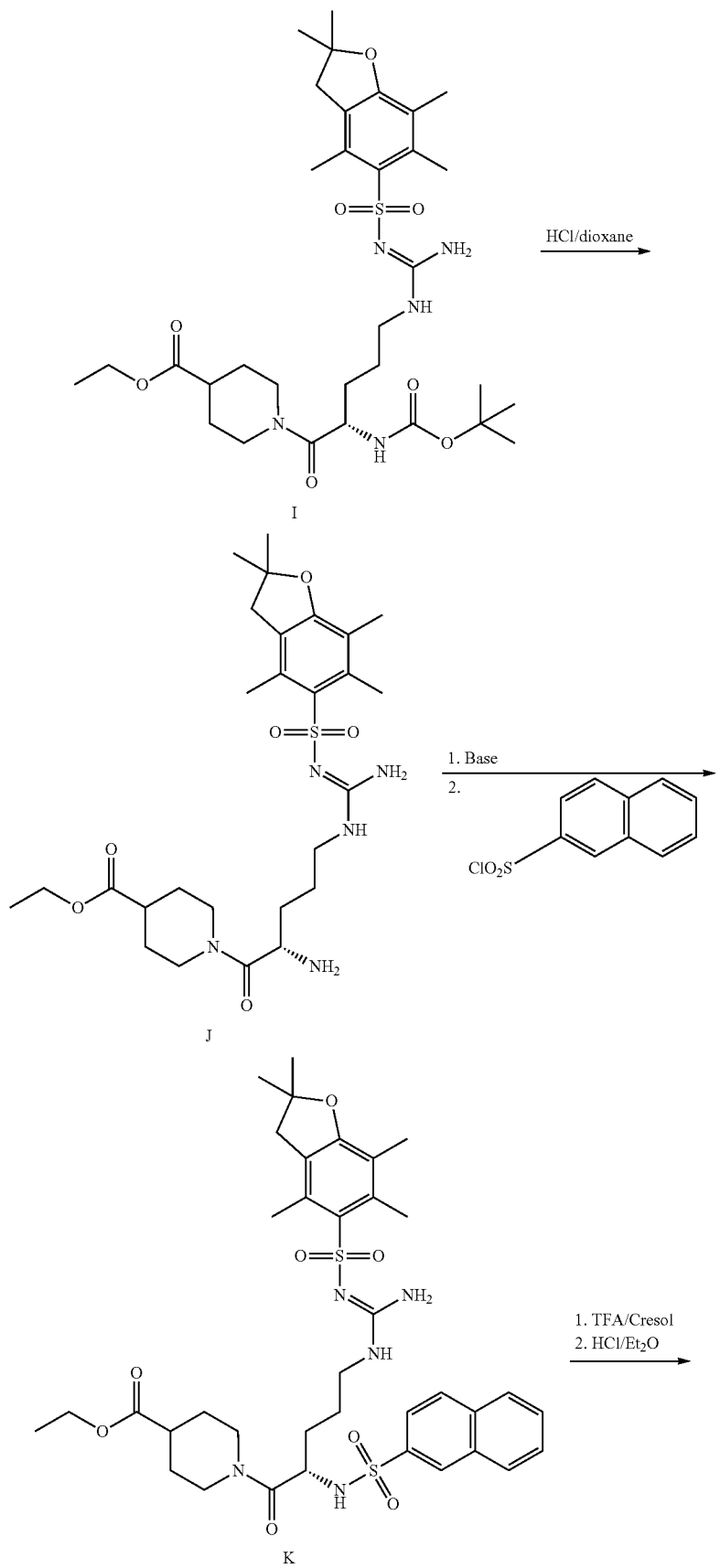

-continued

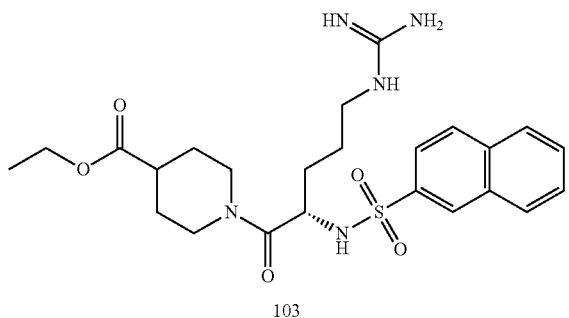

103

Synthesis of 1-[boc-Arg(Pbf)]-piperidine-4-carboxylic acid ethyl ester (I)

To a solution of Boc-Arg(Pbf)-OH (3.4 g, 6.36 mmol) and HATU (2.9 g, 7.63 mmol) in DMF (15 mL) was added DIEA (7.4 mL, 42.4 mmol) and the reaction mixture was stirred for 10 min at room temperature. A solution of ethyl isonipecotate (1.0 g, 6.36 mmol) in DMF (6 mL) was added to the reaction mixture dropwise. The reaction mixture was stirred at room temperature for 1 h, then diluted with EtOAc (150 mL) and poured into water (500 mL). The product was extracted with EtOAc (2×100 mL). The organic layer was washed with aqueous 0.1 N HCl (200 mL), 2% aqueous sodium bicarbonate (200 mL), water (200 mL) and brine (200 mL) The organic layer was then dried over sodium sulfate, filtered, and then evaporated in vacuo. The resultant oily product was dried in vacuo overnight to give compound I (3.7 g, 5.57 mmol) as a viscous solid. LC-MS [M+H] 666.5 ($C_{32}H_{51}N_5O_8$ S+H, calc: 666.7). Compound I was used without further purification.

Synthesis of 1-[Arg(Pbf)]-piperidine-4-carboxylic acid ethyl ester HCl salt (J)

To a solution of compound I (4.7 g, 7.07 mmol) in dichloromethane (25 mL) was added 4N HCl in dioxane (25.0 mL, 84.84 mmol), and the reaction mixture was stirred at room temperature for 2 h. The reaction mixture was concentrated in vacuo to ~20 mL of solvent, and then diluted with diethyl ether (250 mL) to produce a white fine precipitate. The reaction mixture was stirred for 1 h and the solid was washed with ether (50 mL) and dried in vacuo overnight to give compound J (4.3 g, 7.07 mmol) as a fine powder. LC-MS [M+H] 566.5 ($C_{27}H_{43}N_5O_6$ S+H, calc: 566.7). Compound J was used without further purification.

Synthesis of 1-[5(S)—(N'-Pbf-guanidino-2-(naphthalene-2-sulfonylamino)-pentanoyl]-piperidine-4-carboxylic acid ethyl ester (K)

To a solution of compound J (1.1 g. 1.6 mmol) and NaOH (260 mg, 5.9 mmol) in a mixture of THF (5 mL) and water (3 mL) was added a solution of 2-naphthalosulfonyl chloride (0.91 g, 2.5 mmol) in THF (10 mL) dropwise with stirring at ~5° C. The reaction mixture was stirred at room temperature for 1 h, then diluted with water (5 mL). Aqueous 1N HCl (5 mL) was added to obtain pH ~3. Additional water was added (20 mL), and the product was extracted with ethyl acetate (3×50 mL). The organic layer was removed and then washed with 2% aqueous sodium bicarbonate (50 mL), water (50 mL) and brine (50 mL). The extract was dried over anhydrous sodium sulfate, filtered, and was evaporated in vacuo. The formed oily product was dried in vacuo overnight to give compound K (1.3 g, 1.6 mmol) as an oily foaming solid. LC-MS [M+H] 756.5 ($C_{37}H_{49}N_5O_8S_2$+H, calc: 756.7). Compound K was used without further purification.

Synthesis of (S)-ethyl 1-(5-guanidino-2-(naphthalene-2-sulfonamido)pentanoyl)piperidine-4-carboxylate HCl salt (Compound 103)

To a flask, was added compound K (1.3 g, 1.6 mmol) and then treated with 5% m-cresol/TFA (10 mL). The reaction mixture was stirred at room temperature for 1 h. Next, the reaction mixture was concentrated in vacuo to a volume ~5 mL. Diethyl ether (200 mL) was then added to the residue, and formed fine white precipitate. The precipitate was filtered off and washed with ether (2×25 mL). The resultant solid was dried in vacuo overnight to give a crude material, which was purified by preparative reverse phase HPLC. [Nanosyn-Pack Microsorb (100-10) C-18 column (50×300 mm); flow rate: 100 mL/min; injection volume 12 mL (DMSO-water, 1:1, v/v); mobile phase A: 100% water, 0.1% TFA; mobile phase B: 100% ACN, 0.1% TFA; gradient elution from 25% B to 55% B in 90 min, detection at 254 nm]. Fractions containing desired compound were combined and concentrated in vacuo. The residue was dissolved in i-PrOH (50 mL) and evaporated in vacuo (repeated twice). The residue was next dissolved in i-PrOH (5 mL) and treated with 2 N HCl/ether (100 mL, 200 mmol) to give a white precipitate. It was dried in vacuo overnight to give Compound 103 (306 mg, 31% yield, 95.7% purity) as a white solid. LC-MS [M+H] 504.5 ($C_{24}H_{33}N_5O_5$S+H, calc: 504.6).

Example 26
Synthesis of (S)-ethyl 1-(5-guanidino-2-(2,4,6-tri-isopropylphenylsulfonamido)pentanoyl)piperidine-4-carboxylate HCl salt (Compound 104)
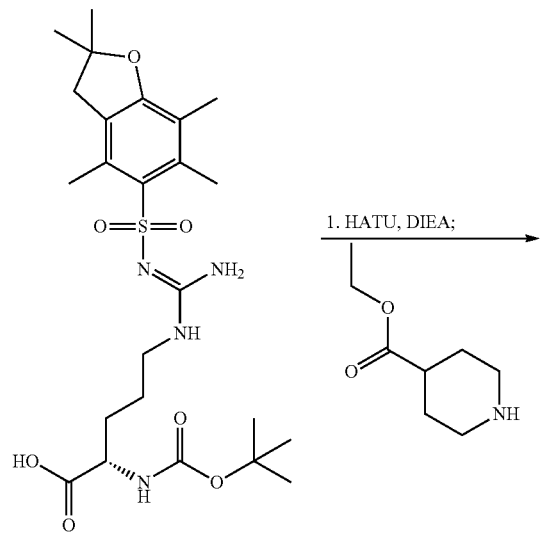
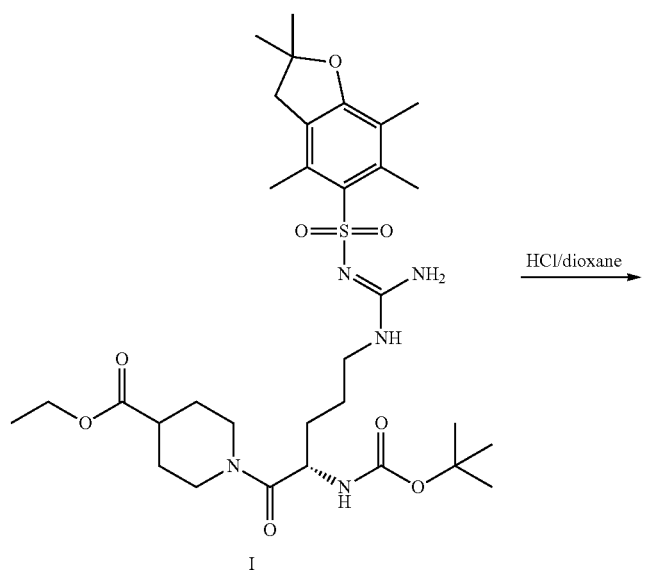

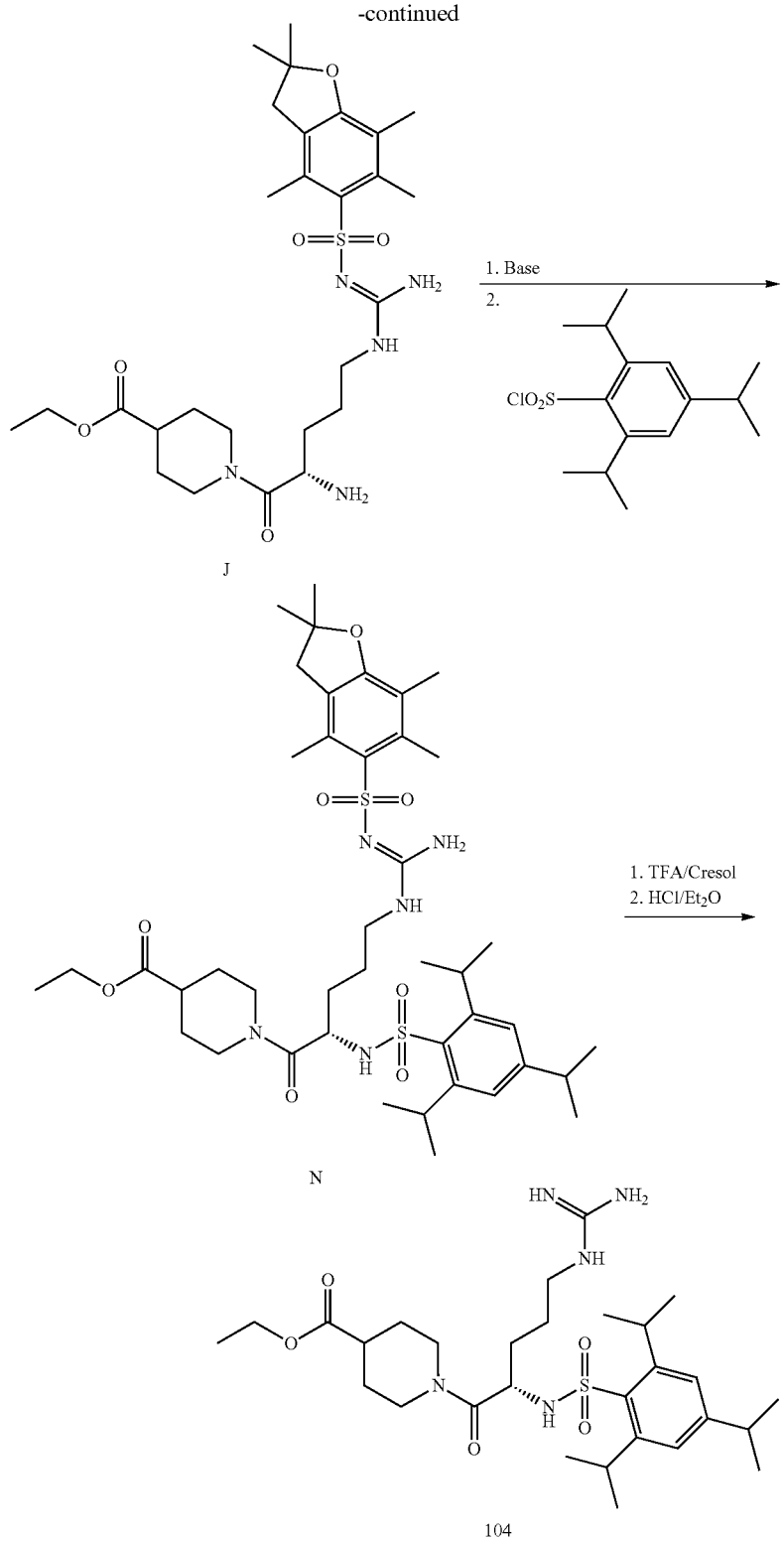

Synthesis of 1-[5(S)-(N'-Pbf-guanidino)-2-(2,4,6-triisopropyl-benzenesulfonylamino)-pentanoyl]-piperidine-4-carboxylic acid ethyl ester (N)

To a solution of compound J (1.0 g, 1.6 mmol) and NaOH (420.0 mg, 10.4 mmol) in a mixture of THF (5 mL) and water (4 mL) was added a solution of 2,4,6-triisopropyl-benzenesulfonyl chloride (2.4 g, 8.0 mmol) dropwise with stirring and maintained at ~5° C. The reaction mixture was then stirred at room temperature for 1 h, monitoring the reaction progress, then diluted with water (20 mL), and acidified with aqueous 1 N HCl (5 mL) to pH ~3. Additional water was added (30 mL), and the product was extracted with EtOAc (3×50 mL). The organic layer was washed with 2% aqueous sodium bicarbonate (50 mL), water (50 mL) and brine (50 mL). The organic layer was dried over anhydrous sodium sulfate, filtered, and was evaporated in vacuo. Formed oily residue was dried in a vacuo overnight to give compound N (1.0 g, 1.2 mmol) as an oily material. LC-MS [M+H] 832.8 ($C_{42}H_{65}N_5O_8S_2$+H, calc: 832.7). Compound N was used without further purification.

Synthesis of (S)-ethyl 1-(5-guanidino-2-(2,4,6-tri-isopropylphenylsulfonamido)pentanoyl)piperidine-4-carboxylate HCl salt (Compound 104)

To a flask was added compound N (2.3 g, 2.8 mmol) and then treated with 5% m-cresol/TFA (16 mL). The reaction mixture was stirred at room temperature for 1 h. The reaction mixture was then concentrated in vacuo to a volume of 5 mL. Hexane (200 mL) was added to the residue and decanted off to give an oily precipitate. The product was purified by preparative reverse phase HPLC. [Nanosyn-Pack Microsorb (100-10) C-18 column (50×300 mm); flow rate: 100 mL/min; injection volume 15 mL (DMSO-water, 1:1, v/v); mobile phase A: 100% water, 0.1% TFA; mobile phase B: 100% ACN, 0.1% TFA; gradient elution from 35% B to 70% B in 90 min, detection at 254 nm]. Fractions containing desired compound were combined and concentrated in vacuo. The residue was dissolved in i-PrOH (100 mL) and evaporated in vacuo (repeated twice). The residue was dissolved in i-PrOH (5 mL) and treated with 2 N HCl/ether (100 mL, 200 mmol) to give an oily residue. It was dried in vacuo overnight to give Compound 104 (1.08 g, 62.8%) as a viscous solid. LC-MS [M+H] 580.6 ($C_{29}H_{49}N_5O_5S$+H, calc: 580.8).

Example 27

Synthesis of (S)-6-(4-(5-guanidino-2-(naphthalene-2-sulfonamido)pentanoyl)piperazin-1-yl)-6-oxo-hexanoic acid (Compound 105)

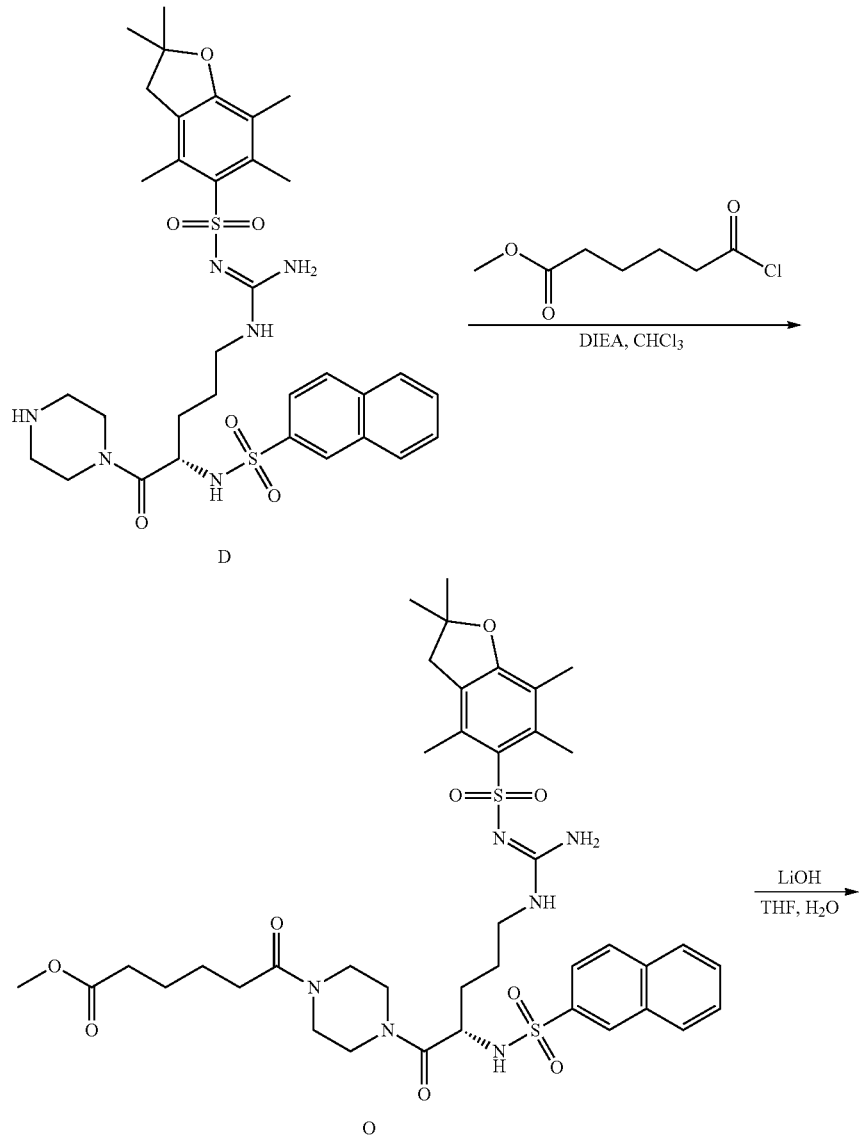

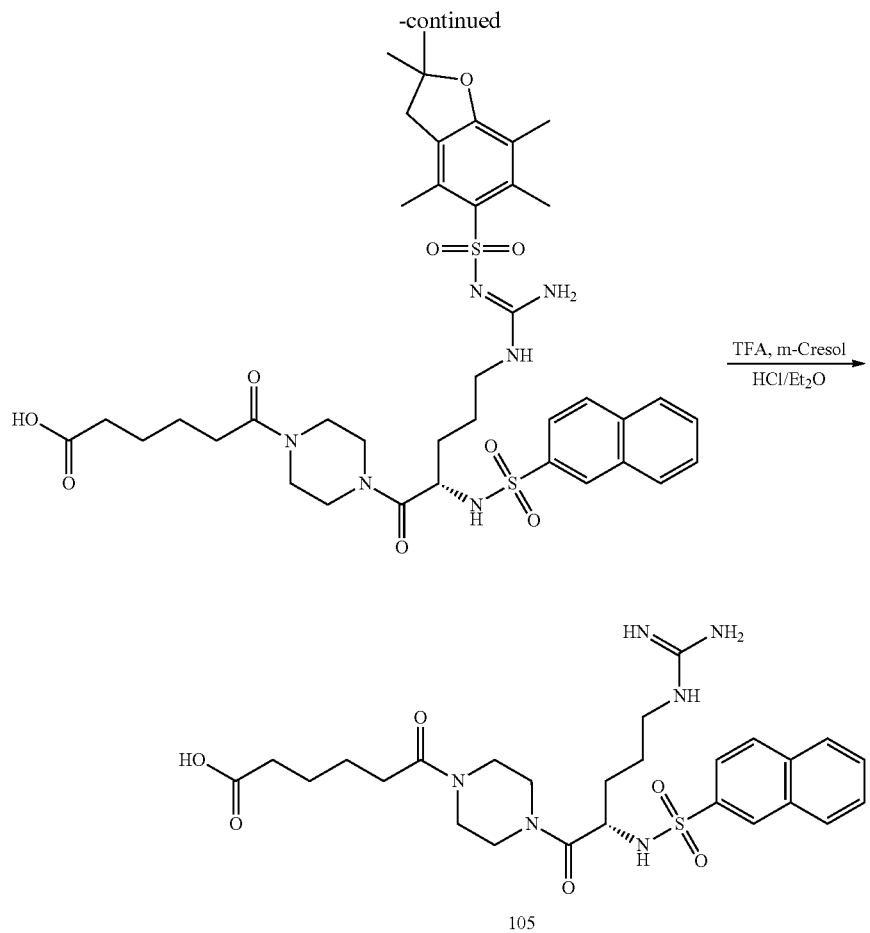

Synthesis of 6-{4-[(S)-5-({Amino-[(E)-2,2,4,6,7-pentamethyl-2,3-dihydro-benzofuran-5-sulfonylimino]-methyl}-amino)-2-(naphthalene-2-sulfonylamino)-pentanoyl]-piperazin-1-yl}-6-oxo-hexanoic acid methyl ester (O)

To a solution of compound D (1.5 g, 2.08 mmol) in CHCl$_3$ (50 mL) was added DIEA (1.21 mL, 4.16 mmol) followed by adipoyl chloride (0.83 mL, 6.93 mmol) dropwise. The reaction mixture was stirred at room temperature overnight (~18 h). Solvents were removed in vacuo and the residue was dried in vacuo to afford the compound O (2.1 g, amount exceeded quantative). LC-MS [M+H] 827.5 (C$_{40}$H$_{54}$N$_6$O$_9$S$_2$+H, calc: 827.3). Compound O was used without further purification.

Synthesis of 6-{4-[(S)-5-({Amino-[(E)-2,2,4,6,7-pentamethyl-2,3-dihydro-benzofuran-5-sulfonylimino]-methyl}amino)-2-(naphthalene-2-sulfonylamino)-pentanoyl]-piperazin-1-yl}-6-oxohexanoic acid (P)

To a solution of compound O (2.1 g, 2.08 mmol) in THF (5 mL), H$_2$O (5 mL) was added 2 M aq LiOH (6 mL). The reaction mixture was stirred at room temperature for 2 h. Solvents were removed in vacuo, then the residue was dissolved in water (~50 mL), acidified with saturated aqueous NaHSO$_4$ (~100 mL) and extracted with EtOAc (2×100 mL). The organic layer was dried over Na$_2$SO$_4$ and removal of the solvent gave compound P (1.72 g, 2.08 mmol). LC-MS [M+H] 813.5 (C$_{39}$H$_{52}$N$_6$O$_9$S$_2$+H, calc: 813.3). Compound P was used without further purification.

Synthesis of (S)-6-(4-(5-guanidino-2-(naphthalene-2-sulfonamido)pentanoyl)piperazin-1-yl)-6-oxohexanoic acid (Compound 105)

A solution of 5% m-cresol/TFA (25 mL) was added to compound P (1.72 g, 2.08 mmol) at room temperature. After stirring for 30 min, the reaction mixture was precipitated with addition of Et$_2$O (~200 mL). The precipitate was filtered and washed with Et$_2$O and dried in vacuo to afford the crude product. The crude product was purified by preparative reverse phase HPLC [Column: VARIAN, LOAD & LOCK, L&L 4002-2, Packing: Microsorb 100-10 C18, Injection Volume: ~25 mL, Injection flow rate: 20 mL/min, 95% A, (water/0.1% TFA), Flow rate: 100 mL/min, Fraction: 30 Sec (50 mL), Method: 5% B (MeCN/0.1% TFA)/5 min/25% B/20 min/25% B/15 min/50% B/25 min/100 mL/min/254 nm]. Solvents were removed from pure fractions in vacuo. Trace amounts of water was removed by co-evaporation with i-PrOH (25 mL) (repeated twice). The residue was dissolved in a minimum amount of i-PrOH, then 2 M HCl in Et$_2$O (~50 mL) was added and diluted with Et$_2$O (~250 mL). Precipitate formed was filtered off and washed with Et$_2$O and dried in vacuo to afford the product as HCl salt Compound 105 (0.74 g, 59% yield, 98.9% purity). LC-MS [M+H] 561.4 (C$_{26}$H$_{36}$N$_6$O$_6$S+H, calc: 561.2).

Example 28

Synthesis of 3-(4-carbamimidoylphenyl)-2-oxopropanoic acid (Compound 107)

Compound 107, i.e., 3-(4-carbamimidoylphenyl)-2-oxopropanoic acid can be produced using methods known to those skilled in the art, such as that described by Richter P et al, Pharmazie, 1977, 32, 216-220 and references contained within. The purity of Compound 107 used herein was estimated to be 76%, an estimate due low UV absorbance of this compound via HPLC. Mass spec data: LC-MS [M+H] 207.0 (C10H10N2O3+H, calc: 207.1).

Example 29

Synthesis of (S)-5-(4-carbamimidoylbenzylamino)-5-oxo-4-((R)-4-phenyl-2-(phenylmethylsulfonamido)butanamido)pentanoic acid (Compound 108)

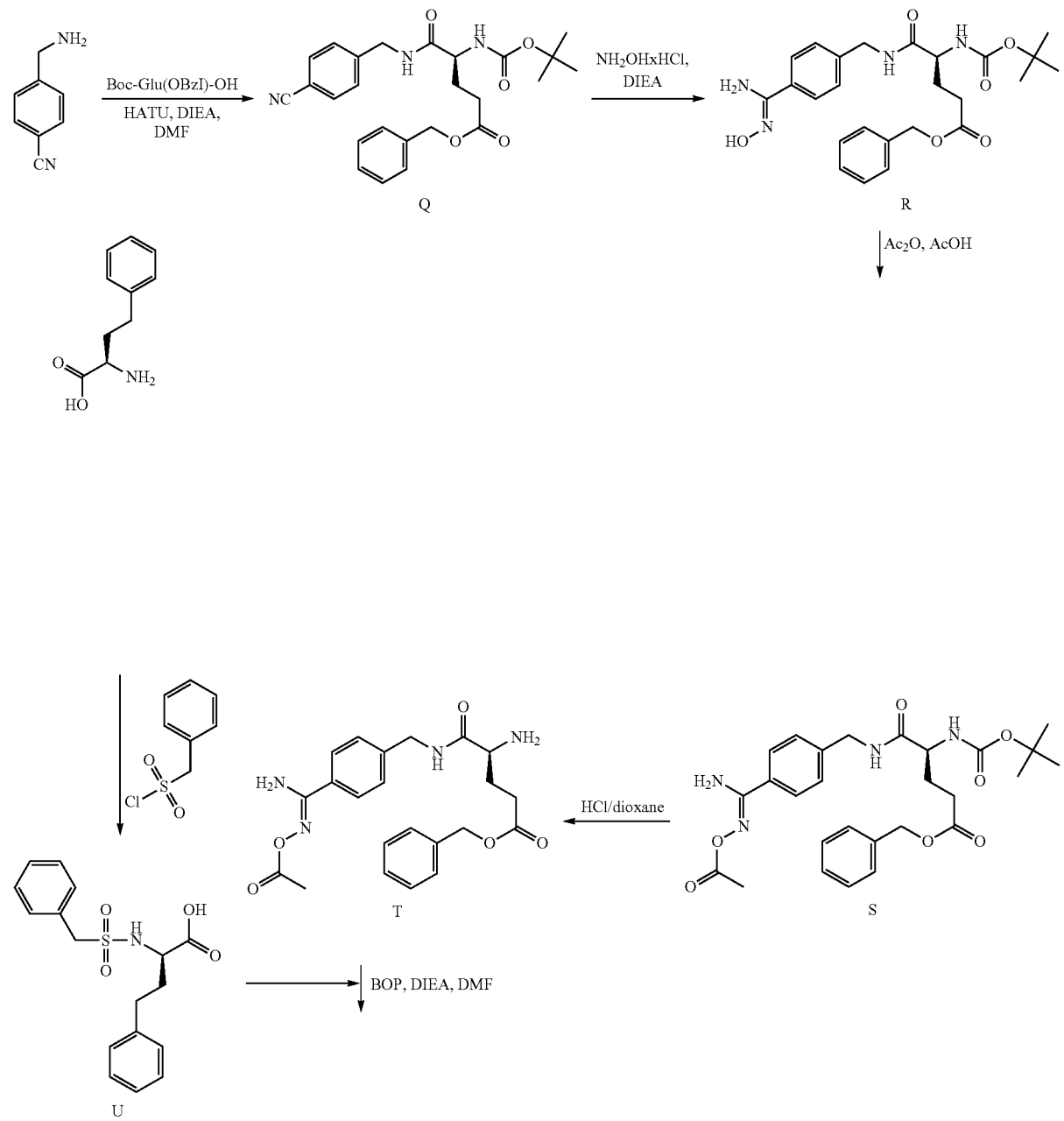

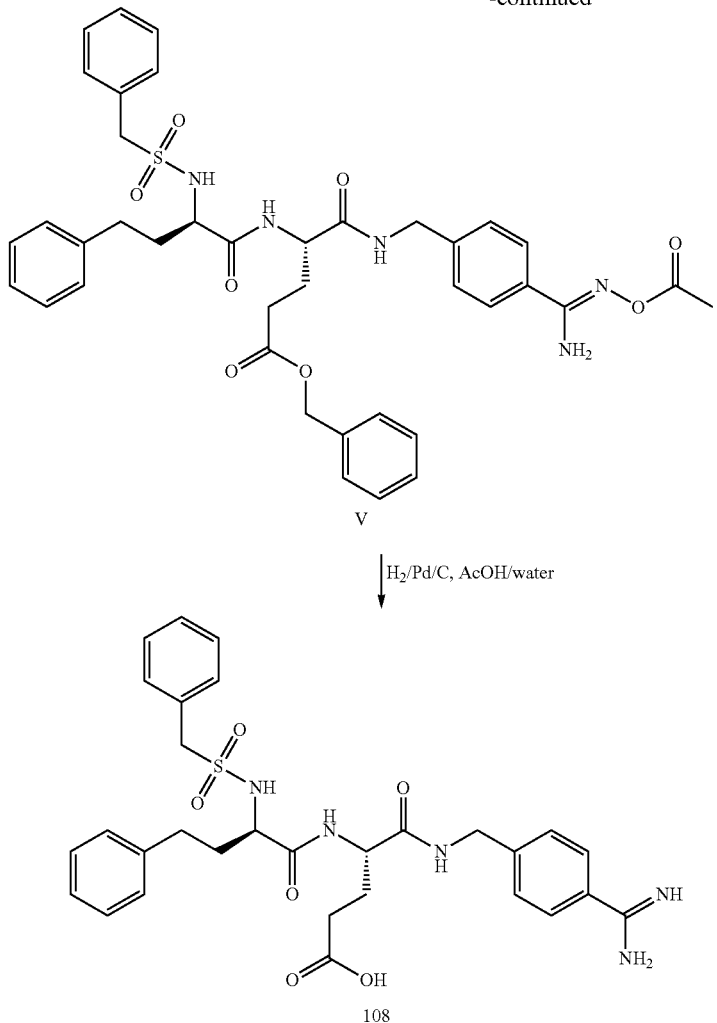

V

H₂/Pd/C, AcOH/water

108

Preparation 30

Synthesis of (S)-4-tert-butoxycarbonylamino-4-(4-cyano-benzylcarbamoyl)-butyric acid benzyl ester (Q)

A solution of Boc-Glu(OBzl)-OH (7.08 g, 21.0 mmol), BOP (9.72 g, 22.0 mmol) and DIEA (12.18 mL, 70.0 mmol) in DMF (50 mL) was maintained at room temperature for 20 min, followed by the addition of 4-(aminomethyl)benzonitrile hydrochloride (3.38 g, 20.0 mmol). The reaction mixture was stirred at room temperature for an additional 1 h and diluted with EtOAc (500 mL) The obtained solution was extracted with water (100 mL), 5% aq. NaHCO₃ (100 mL) and water (2×100 mL). The organic layer was dried over MgSO₄, evaporated and dried in vacuo to provide compound Q (9.65 g, yield exceeded quantitative) as yellowish oil. LC-MS [M+H] 452.0 ($C_{25}H_{29}N_3O_5$+H, calc: 452.4). Compound Q was used without further purification.

Synthesis of (S)-4-tert-butoxycarbonylamino-4-[4-(N-hydroxycarbamimidoyl)-benzyl carbamoyl]-butyric acid benzyl ester (R)

A solution of compound Q (9.65 g, 20.0 mmol), hydroxylamine hydrochloride (2.10 g, 30.0 mmol) and DIEA (5.22 mL, 30.0 mmol) in ethanol (abs., 150 mL) was refluxed for 6 h. The reaction mixture was allowed to cool to room temperature and stirred for additional 16 h. The solvents were evaporated in vacuo. The resultant residue was dried in vacuo to provide compound R (14.8 g, yield exceeded quantitative) as yellowish oil. LC-MS [M+H] 485.5 ($C_{25}H_{32}N_4O_6$+H, calc: 485.8). Compound R was used without further purification.

Synthesis of (S)-4-tert-butoxycarbonylamino-4-[4-(N-acetylhydroxycarbamimidoyl)-benzyl carbamoyl]-butyric acid benzyl ester (S)

A solution of compound R (14.8 g, 20.0 mmol) and acetic anhydride (5.7 mL, 60.0 mmol) in acetic acid (100 mL) was stirred at room temperature for 45 min, and then solvent was evaporated in vacuo. The resultant residue was dissolved in EtOAc (300 mL) and extracted with water (2×75 mL) and brine (75 mL). The organic layer was then dried over MgSO₄, evaporated and dried in vacuo to provide compound S (9.58 g, 18.2 mmol) as yellowish solid. LC-MS [M+H] 527.6 ($C_{27}H_{34}N_4O_7$+H, calc: 527.9). Compound S was used without further purification.

Synthesis of (S)-4-[4-(N-acetylhydroxycarbamimidoyl)-benzyl carbamoyl]-butyric acid benzyl ester (T)

Compound S (9.58 g, 18.2 mmol) was dissolved in 1,4-dioxane (50 mL) and treated with 4 N HCl/dioxane (50 mL, 200 mmol) at room temperature for 1 h. Next, the solvent was evaporated in vacuo. The resultant residue was triturated with ether (200 mL). The obtained precipitate was filtrated, washed with ether (100 mL) and hexane (50 mL) and dried in vacuo to provide compound T (9.64 g, yield exceeded quantitative) as off-white solid. LC-MS [M+H] 426.9 ($C_{22}H_{26}N_4O_5$+H, calc: 427.3). Compound T was used without further purification.

Synthesis of (R)-4-phenyl-2-phenylmethanesulfonylamino-butyric acid (U)

A solution of D-homo-phenylalanine (10.0 g, 55.9 mmol) and NaOH (3.35 g, 83.8 mmol) in a mixture of 1,4-dioxane (80 mL) and water (50 mL) was cooled to ~5° C., followed by alternate addition of α-toluenesulfonyl chloride (16.0 g, 83.8 mmol; 5 portions by 3.2 g) and 1.12 M NaOH (50 mL, 55.9 mmol; 5 portions by 10 mL) maintaining pH >10. The reaction mixture was then acidified with 2% aq. $H_2SO_4$ to a pH of about pH 2. The obtained solution was extracted with EtOAc (2×200 mL). The obtained organic layer was washed with water (3×75 mL), dried over $MgSO_4$ and then the solvent was evaporated in vacuo. The resultant residue was dried in vacuo to provide compound U (12.6 g, 37.5 mmol) as white solid. LC-MS [M+H] 334.2 ($C_{17}H_{19}NO_4S$+H, calc: 333.4). Compound U was used without further purification.

Synthesis of (S)-4-[4-(N-acetylhydroxycarbamimidoyl)-benzylcarbamoyl]-4-((R)-4-phenyl-2-phenylmethanesulfonylamino-butyrylamino)-butyric acid benzyl ester (V)

A solution of compound U (5.9 g, 17.8 mmol), compound T di-hydrochloride (18.0 mmol), BOP (8.65 g, 19.6 mmol) and DIEA (10.96 mL, 19.6 mmol) in DMF (250 mL) was stirred at room temperature for 2 h. The reaction mixture was then diluted with EtOAc (750 mL) and extracted with water (200 mL). The formed precipitate was filtrated, washed with EtOAc (200 mL) and water (200 mL) and dried at room temperature overnight (~18 h) to provide compound V (8.2 g, 11.0 mmol) as off-white solid. LC-MS [M+H] 743.6 ($C_{39}H_{43}N_5O_8S$+H, calc: 743.9). Compound V was used without further purification.

Synthesis of (S)-5-(4-carbamimidoylbenzylamino)-5-oxo-4-((R)-4-phenyl-2-(phenylmethylsulfonamido)butanamido)pentanoic acid (Compound 108)

Compound V (8.0 g, 10.77 mmol) was dissolved in acetic acid (700 mL) followed by the addition of Pd/C (5% wt, 3.0 g) as a suspension in water (50 mL). Reaction mixture was subjected to hydrogenation (Parr apparatus, 50 psi $H_2$) at room temperature for 3 h. The catalyst was filtered over a pad of Celite on sintered glass filter and washed with methanol. Filtrate was evaporated in vacuo to provide Compound 108 as colorless oil. LC-MS [M+H] 594.2 ($C_{30}H_{35}N_5O_6S$+H, calc: 594). Obtained oil was dissolved in water (150 mL) and subjected to HPLC purification. [Nanosyn-Pack YMC-ODS-A (100-10) C-18 column (75×300 mm); flow rate: 250 mL/min; injection volume 150 mL; mobile phase A: 100% water, 0.1% TFA; mobile phase B: 100% acetonitrile, 0.1% TFA; isocratic elution at 10% B in 4 min., gradient elution to 24% B in 18 min, isocratic elution at 24% B in 20 min, gradient elution from 24% B to 58% B in 68 min; detection at 254 nm]. Fractions containing desired compound were combined and concentrated in vacuo. Residue was dissolved in i-PrOH (75 mL) and evaporated in vacuo (procedure was repeated twice) to provide Compound 108 (4.5 g, 70% yield, 98.0% purity) as white solid. LC-MS [M+H] 594.2 ($C_{30}H_{35}N_5O_6S$+H, calc: 594). Retention time*: 3.55 min. *—[Chromolith SpeedRod RP-18e C18 column (4.6×50 mm); flow rate 1.5 mL/min; mobile phase A: 0.1% TFA/water; mobile phase B 0.1% TFA/acetonitrile; gradient elution from 5% B to 100% B over 9.6 min, detection 254 nm].

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for controlled release of amphetamine to a patient comprising orally administering a pharmaceutical composition to the patient in need thereof, the composition comprising:
   a pharmaceutically acceptable carrier; and
   a compound of formula AM-1; AM-2; or AM-5:

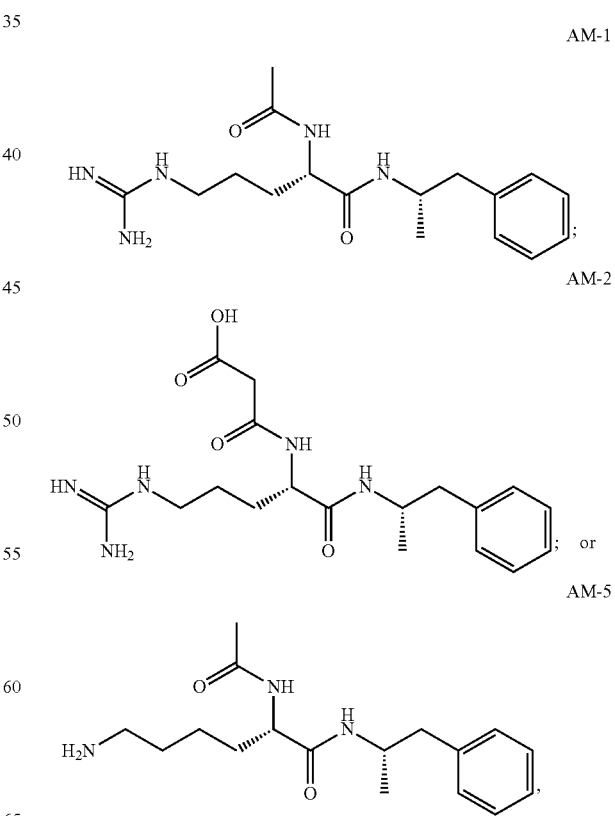

or a salt, hydrate or solvate thereof.

2. The method of claim 1, further comprising a GI enzyme inhibitor.

3. The method of claim 2, wherein the GI enzyme inhibitor is a trypsin inhibitor.

4. The method of claim 1, wherein the composition comprises a dosage of the compound of from 0.6 mg/kg to 65 mg/kg.

5. The method of claim 1, wherein the composition comprises a compound of formula AM-1 in a dosage amount of from 4 mg/kg to 32 mg/kg.

6. The method of claim 5, wherein the composition comprises a compound of formula AM-1 in a dosage amount of about 5 mg/kg.

7. The method of claim 5, wherein the composition comprises a compound of formula AM-1 in a dosage amount of about 6 mg/kg.

8. The method of claim 5, wherein the composition comprises a compound of formulate AM-1 in a dosage amount of about 24 mg/kg.

9. The method of claim 5, wherein the composition comprises a compound of formulate AM-1 in a dosage amount of about 32 mg/kg.

10. The method of claim 1, wherein the composition comprises a compound of formula AM-2 in a dosage amount of from 4 mg/kg to 64 mg/kg.

11. The method of claim 10, wherein the composition comprises a compound of formula AM-2 in a dosage amount of about 6 mg/kg.

12. The method of claim 10, wherein the composition comprises a compound of formulate AM-2 in a dosage amount of about 27 mg/kg.

13. The method of claim 10, wherein the composition comprises a compound of formula AM-2 in a dosage amount of about 64 mg/kg.

14. The method of claim 1, wherein the composition comprises a compound of formula AM-5 in a dosage amount of from 4 mg/kg to 27 mg/kg.

15. The method of claim 14, wherein the composition comprises a compound of formulate AM-5 in a dosage amount of about 4.5 mg/kg.

16. The method of claim 14, wherein the composition comprises a compound of formulate AM-5 in a dosage amount of about 22 mg/kg.

17. A method for reducing amphetamine abuse, the method comprising:

orally administering a pharmaceutical composition to a patient, the composition comprising:

a pharmaceutically acceptable carrier; and a compound of formula AM-1; AM-2; or AM-5:

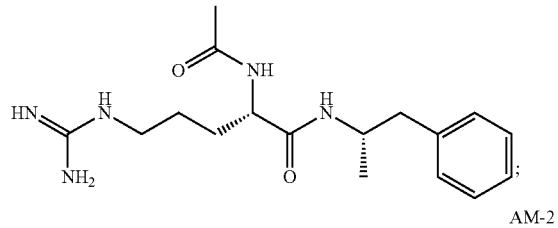

AM-1

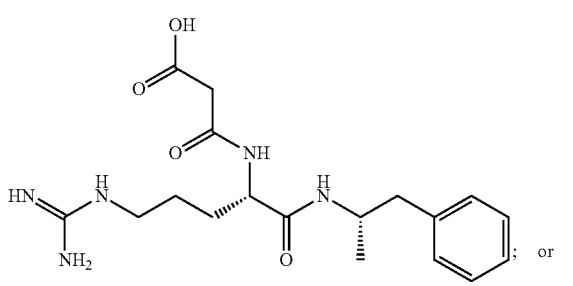

AM-2

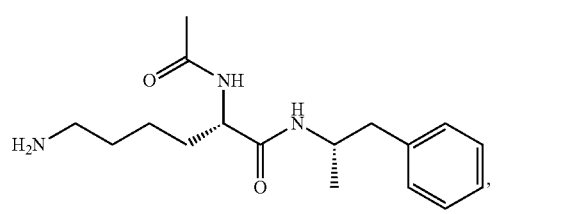

AM-5 or a salt, hydrate or solvate thereof.

* * * * *